(12) United States Patent
Yu et al.

(10) Patent No.: US 12,220,148 B2
(45) Date of Patent: *Feb. 11, 2025

(54) PREPUCE EXTRUDING, CUTTING, HEMOSTASIS, AND HEALING ASSEMBLY USING ULTRASONIC WAVE

(71) Applicant: WUHU SHANGRING TECHNOLOGY CO., LTD, Wuhu (CN)

(72) Inventors: Huarong Yu, Beijing (CN); Shujie Xia, Shanghai (CN); Jianzhong Shang, Wuhu (CN); Jingjing Shang, Wuhu (CN); Yifeng Peng, Wuhu (CN)

(73) Assignee: WUHU SHANGRING TECHNOLOGY CO., LTD, Wuhu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/727,750

(22) Filed: Apr. 24, 2022

(65) Prior Publication Data
US 2022/0354525 A1   Nov. 10, 2022

Related U.S. Application Data

(63) Continuation of application No. 16/478,143, filed as application No. PCT/CN2018/072184 on Jan. 11, 2018, now Pat. No. 11,357,537.

(30) Foreign Application Priority Data

Jan. 16, 2017   (CN) .......................... 201720048313.3

(51) Int. Cl.
*A61B 17/326* (2006.01)
*A61B 17/12* (2006.01)
(Continued)

(52) U.S. Cl.
CPC ............ *A61B 17/326* (2013.01); *A61B 17/12* (2013.01); *A61B 17/320068* (2013.01); *A61B 2017/12004* (2013.01); *A61M 11/00* (2013.01)

(58) Field of Classification Search
CPC ........ A61B 17/326; A61B 17/12–2017/12018; A61B 2017/12004; A61B 17/122–1285;
(Continued)

(56) References Cited

U.S. PATENT DOCUMENTS

| 4,016,882 A | * | 4/1977 | Broadwin | ........ A61B 17/22012 606/169 |
| 5,188,102 A | * | 2/1993 | Idemoto | .............. A61M 3/0279 606/45 |

(Continued)

*Primary Examiner* — Brigid K Byrd

(57) ABSTRACT

A prepuce extruding, cutting, hemostasis, and healing assembly using ultrasonic wave. Ultrasonic wave is applied in extruding, cutting, hemostasis, and healing of prepuce at a conjunction of internal and external tissues of a distal part of a human body. The assembly includes an ultrasonic generating device, a transmission device and a circumcision device. The ultrasonic generating device is used for generating ultrasonic waves, is connected to the transmission device and can send the ultrasonic waves to the transmission device. The transmission device is connected to the circumcision device and can send the ultrasonic waves to the circumcision device. The circumcision device is used for extruding and cutting a prepuce and/or performing hemostasis and/or healing of wounds. In this way, circumcision can be completed within just several seconds, and immediate healing can be achieved, preventing bleeding during and after a surgery.

19 Claims, 53 Drawing Sheets

(51) Int. Cl.
*A61B 17/32* (2006.01)
*A61M 11/00* (2006.01)

(58) Field of Classification Search
CPC .......................................... A61B 17/32; A61B 17/320068–2017/320098; A61B 17/3201; A61B 17/3205–32056; A61B 17/3209–3217; A61B 17/0684; A61M 11/00; A61M 2210/167
See application file for complete search history.

(56) References Cited

U.S. PATENT DOCUMENTS

| | | | | |
|---|---|---|---|---|
| 5,649,937 | A * | 7/1997 | Bito | A61B 17/1285 606/151 |
| 6,036,698 | A * | 3/2000 | Fawzi | A61B 10/0266 600/562 |
| 2010/0185220 | A1* | 7/2010 | Naghavi | A61B 5/14546 600/301 |
| 2015/0313624 | A1* | 11/2015 | Altokhais | A61B 18/1815 606/118 |
| 2016/0367279 | A1* | 12/2016 | Orphanos | A61B 17/3417 |
| 2017/0035487 | A1* | 2/2017 | Kadykowski | A61B 18/04 |
| 2018/0055528 | A1* | 3/2018 | Weng | A61B 17/1155 |

* cited by examiner $\dfrac{I}{2:1}$ 11-1     11-2     11-3     11-4

I

F-F

PREPUCE EXTRUDING, CUTTING, HEMOSTASIS, AND HEALING ASSEMBLY USING ULTRASONIC WAVE

CROSS REFERENCE TO THE RELATED APPLICATIONS

This application a continuation application of U.S. Ser. No. 16/478,143, filed on Jul. 16, 2019. U.S. Ser. No. 16/478,143 is the national phase entry of International Application No. PCT/CN2018/072184, filed on Jan. 11, 2018, which is based upon and claims priority to Chinese Patent Application No. 201720048313.3, filed on Jan. 16, 2017, the entire contents of which are incorporated herein by reference.

TECHNICAL FIELD

The present invention relates to the field of ultrasonic surgical instruments, in particular to an ultrasound subassembly for foreskin compressing, cutting, hemostasis and healing.

BACKGROUND

Redundant prepuce or phimosis is one of the causes of male urinary tract infections and sexually transmitted diseases. Redundant prepuce or phimosis can cause urinary tract infections that may lead to chronic prostatitis, which may result in a series of symptoms including backache, impotence and prospermia, etc. Therefore, removing redundant foreskin or phimosis is a good measure to prevent these diseases. The method to remove the redundant foreskin is a long-term evolution, includes:

(a) Before the 1990s, surgeries are used to remove the phimosis or redundant foreskin. The techniques include removal of the redundant foreskin, hemostasis, and apposition suture on the cut edge of the skin. Patients cannot ambulate after the operation, and it is painful for the patients at each dressing change. Patients further may suffer great pain when stitches are removed. Further, incomplete hemostasis of ligation will cause the foreskin hematoma which need a re-operation. In addition, as the excision of the foreskin acrobystia and hemostasis are performed separately, the operation time is prolonged, which will fear the patient more.

(b) In the 1990s, although surgeries including dorsal slit method of circumcision, sleeve circumcision, etc. generate successively, there are still many inconveniences. These surgeries are likely to cause the asymmetry of the retained foreskin, knotting reaction of the ligature thread, and need of taking out the suture after surgery, etc., which will cause bleeding and infection easily.

(c) Subsequently, the countries, mainly the South Korea, developed a circumcision using elastic thread in combination with a circumcision ring. However, pain, bleeding, and the risk of infection were unavoidable during the surgery, and oral administration of analgesic and anti-infective drugs are required. Further, wounds should be cleaned daily, and the circumcision should be performed 2-4 days after surgery. A series of operations including decycling and suture removal are performed after a certain interval of time. The operation time is extremely long and the operation is cumbersome, resulting in more risk and uncertainty.

(d) To solve the existing problems, a method of applying laser and high frequency electric knife technology are used in circumcision is developed. Although the method replaces the method of scissors cutting and coagulates the bleeding spot, it will burn the tissue of the patient and cause infection easily.

(e) Later, a circumcision assembly is developed in the art, suturing nails are used to suture the incision of the foreskin at one time. The strategy provided in Chinese patent application CN201210497584.9 titled "circumcision device" requires a plurality of U-shaped nails hammered into the body tissue, which will cause hemorrhage and infection easily and lead to great pain psychologically and physically for patients. Patients need to carry the nails for a long time after surgery, which will lead to mobility difficulties and risks including de-nail.

(f) The most advanced technology in the art is a circumcision device using an inner and an outer ring to cooperate for circumcision. However, in some variant embodiments, for example, the Chinese patent application CN201310024391.6 titled "circumcision stapler", the "lacing protective unit" disposed therein leads to the non-tightly match of the inner ring and the outer ring when clamping. Namely, it cannot block the blood vessel corresponding to the foreskin completely so that the redundant foreskin cannot necrosis and fall off successfully.

It can be seen from the technical routes in the decades in the art that, there are still the following technical problems to be solved in the circumcision field:

(1) The incision cannot heal in a short time after the circumcision;

(2) The annular section is unaesthetic due to the limitation of the structure of the circumcision device, which will lead to a lifelong regret;

(3) The section may not form a complete ring in a certain probability;

(4) The blade and scissors cut in the body tissue lead to psychological fear and physical pain of the patients;

(5) Patients need to carry the nails or the rings after surgery, which will lead to psychological fear and physical pain.

(6) The use of suturing nails will puncture the blood vessels easily due to uncertainty of the location of the suturing nail, therefore the blood vessels are difficult to heal and will lead to postoperative bleeding;

(7) Patients need to carry the nails for several days to more than ten days after surgery, which will lead to many inconvenience. And the patients will take the risk of de-nail if taking strenuous exercise or suffering from an external force, which will lead to a dangerous;

(8) Carrying the nails after surgery will lead to the risk of bleeding or de-nail when physiologically erects;

(9) The scab or slowly healing of the section of the traditional surgery will lead to the lose of original elasticity of the foreskin;

(10) The traditional surgery will last several minutes or even a half day, the long time of operation will lead to various risks;

(11) The traditional surgery will cause bleeding easily, which leading to the risk of infectious disease;

(12) Laser cutting of the foreskin produces eschar and irritating odors.

SUMMARY

In view of the above problems, an objective of the present invention is to provide an ultrasound subassembly for foreskin compressing, cutting, hemostasis and healing capable of completing a circumcision in only a few seconds and the cutting site will heal immediately. The hemorrhage during and after the surgery, and transmitted diseases are avoided. The risks of bleeding, de-nail and decycling when the patient physiologically erects after the surgery are avoided. The specific technical method is as follows:

An ultrasound subassembly for foreskin compressing, cutting, hemostasis and healing, wherein the ultrasound is applied to the foreskin compressing, cutting, hemostasis and healing at a junction of an internal and an external tissue of a tip of human. The ultrasound subassembly includes an ultrasonic generating device, a transmission device and a circumcision device. The ultrasonic generating device is used to generate a plurality of ultrasonic waves, and the ultrasonic generating device is connected to the transmission device and capable of transmitting the plurality of ultrasonic waves to the transmission device. The transmission device is connected to the circumcision device and capable of transmitting the plurality of ultrasonic waves to the circumcision device. The circumcision device is used to compress and/or cut the foreskin, and/or, for hemostasis and/or healing of a wound.

Further, the circumcision device includes a first end and a second end, wherein the first end is a foreskin fixing end, the second end is a compressing, cutting, hemostasis or healing end; wherein the foreskin fixing end cooperates with the compressing, cutting, hemostasis or healing end to compress and/or cut the foreskin, and/or, for hemostasis and/or healing of the wound.

Further, a conjunctive mode of the foreskin fixing end and the compressing, cutting, hemostasis or healing end is that the foreskin fixing end is placed on an inner plate or an outer plate of foreskin, and the compressing, cutting, hemostasis or healing end is used to place on a position of the inner plate or the outer plate of the foreskin corresponding to the foreskin fixing end.

Further, the foreskin fixing end and the compressing, cutting, hemostasis or healing end are positioned on the inner plate and the outer plate of the foreskin respectively to cooperate to clamp the foreskin, and used to compress and/or cut the foreskin, and/or, for hemostasis and/or healing of the wound.

Further, the foreskin fixing end includes a first annular contact surface, the compressing, cutting, hemostasis or healing end includes a second annular contact surface; wherein the first annular contact surface cooperates with the second annular contact surface to make the foreskin placed between the two contact surfaces.

Further, both the first annular contact surface and the second annular contact surface are closed circular contact surfaces.

Further, the foreskin fixing end is a first ring and the compressing, cutting, hemostasis or healing end is a second ring.

Further, the first ring and the second ring are disposed corresponding to an inside and an outside of the foreskin, or the second ring and the first ring are disposed corresponding to the inside and the outside of the foreskin.

Further, the first ring is an inner ring used for being disposed in an inner part of the foreskin, the second ring is an outer ring used for being disposed in an outside part of the foreskin, wherein the inner ring and the outer ring cooperate to fasten the foreskin.

Further, the inner ring is a closed circular ring, the outer ring includes an opening, wherein the opening is capable of being closed by a locking device.

Further, the foreskin fixing end is configured to be a positioning cylinder allowing a glans penis to be partially inserted, wherein a distal end of the positioning cylinder bulges outwards radially to form a flange, wherein the first annular contact surface is formed on a proximal-facing surface of the flange, the foreskin wraps around the flange and being supported on the first annular contact surface; wherein the compressing, cutting, hemostasis or healing end is a cutting device configured on a same frame with the positioning cylinder and capable of being actuated toward the foreskin fixing end, wherein the cutting device includes the second annular contact surface.

Further, the foreskin fixing end is configured to be a positioning cylinder capable of being sleeved on the glans penis, wherein the first annular contact surface is formed on a near end of the positioning cylinder, wherein the foreskin is supported on a first surface; wherein the compressing, cutting, hemostasis or healing end is a cutting device configured on a same frame with the positioning cylinder and capable of being actuated toward the foreskin fixing end, wherein the cutting device includes the second annular contact surface.

Further, an angle between the first annular contact surface and an axis of the positioning cylinder is an acute angle.

Further, the foreskin fixing end is connected to the transmission device, and/or, the compressing, cutting, hemostasis or healing end is connected to the transmission device, receives the plurality of ultrasonic waves transmitted by the transmission device and compresses and/or cuts the foreskin, and/or, for applying a hemostasis and/or healing for the wound.

Further, the transmission device and the foreskin fixing end and/or the compressing, cutting, hemostasis or healing end are fixedly connected through an internal and external thread or a buckle.

Further, the foreskin fixing end and the compressing, cutting, hemostasis or healing end are positioned on the inner plate and the outer plate of foreskin respectively to cooperate to clamp the foreskin, wherein a clamping degree thereof is 9%-87% of a thickness of the foreskin in natural state.

Further, the foreskin fixing end and the compressing, cutting, hemostasis or healing end are positioned on the inner plate and the outer plate of the foreskin respectively to cooperate to clamp the foreskin, wherein a clamping force thereof is 0.02-3.5 N/mm.

Further, ultrasound subassembly for foreskin compressing, cutting, hemostasis and healing further includes a water mist generator used for applying powder, water and/or water mist onto the circumcision device and/or a circumcision area prior to the circumcision, during the circumcision and/or after the circumcision.

Further, the water mist generator is disposed separately with respect to the ultrasonic generating device, the transmission device and the circumcision device; and/or, the water mist generator is partly or entirely integrated on the ultrasonic generating device, the transmission device or the circumcision device.

More preferably, the following features may be employed: the inner ring is used for being disposed in an inner part of the foreskin, the outer ring is used for being disposed in an outside part of the foreskin, wherein the inner ring and the outer ring cooperate to fasten the foreskin; or, the inner ring is used to sleeve on a penis and the outside part of the foreskin and used for being disposed in an inverted foreskin when the foreskin inverts, the outer ring is used for being disposed in the outside part of the inverted foreskin, the inner ring and the outer ring cooperate to fasten the foreskin.

The circumcision device has a vibrational frequency of 55.5 kHz to 166.5 kHz, preferably 135 kHz.

The ultrasonic generating device includes an ultrasonic generator and an ultrasonic transducer, the ultrasonic generator is drivingly connected to the ultrasonic transducer, the ultrasonic transducer is connected to the transmission device.

The transmission device is an ultrasonic transmitting rod.

The ultrasonic generating device is connected to a control unit, the ultrasonic generating device includes a longitudinal ultrasound driver and a transverse ultrasound driver.

Compared with the prior art, the present invention is a revolutionary innovation in the field of circumcision. The improvements are as follows:

(1) The ultrasonic generating device generates a plurality of ultrasonic waves and transmit the plurality of ultrasonic waves to a foreskin cutting end; the frictional heat caused by the mechanical vibration can coagulate the foreskin from blooding while cutting the foreskin. The hemorrhage can be completely stopped in a few minutes and the foreskin is almost healed.

(2) The ultrasonic generating device generates a plurality of ultrasonic waves and transmit the plurality of ultrasonic waves to a foreskin cutting end to make the annular section of the circumcision aesthetic.

(3) The plurality of ultrasonic waves makes the water in the foreskin contact with the circumcision device vaporized instantaneous to form a complete ring;

(4) The elimination of blade and scissors cut greatly alleviate the fear and physical pain of the patient.

(5) Patients don't need to nail or ring the penis after the circumcision.

(6) The blood vessels of the foreskin will heal in a few minutes after the surgery, the risk of blooding during or after the circumcision is avoided.

(7) Nailing and ringing the penis in the following seven days or more than ten days of surgery is avoided. The inconvenience in daily life of the patient is solved and the risk of de-nail or decycling when taking strenuous exercise or suffering from an external force is avoided.

(8) The hemostasis, de-nail and decycling caused by the physiologically erection are avoided.

(9) The circumcision using the circumcision device of the present invention will make the healing surface of the circumcision smooth and natural, the original elasticity of the foreskin is maintained.

(10) It will take just several seconds for circumcision using the circumcision device of the present invention.

(11) The foreskin will heal immediately after surgery using the circumcision device of the present invention. The hemorrhage during and after the surgery, and transmitted diseases are avoided.

(12) The scars and smoke occur in the laser surgery are avoided. The annular section will heal smoothly.

Figure 1:
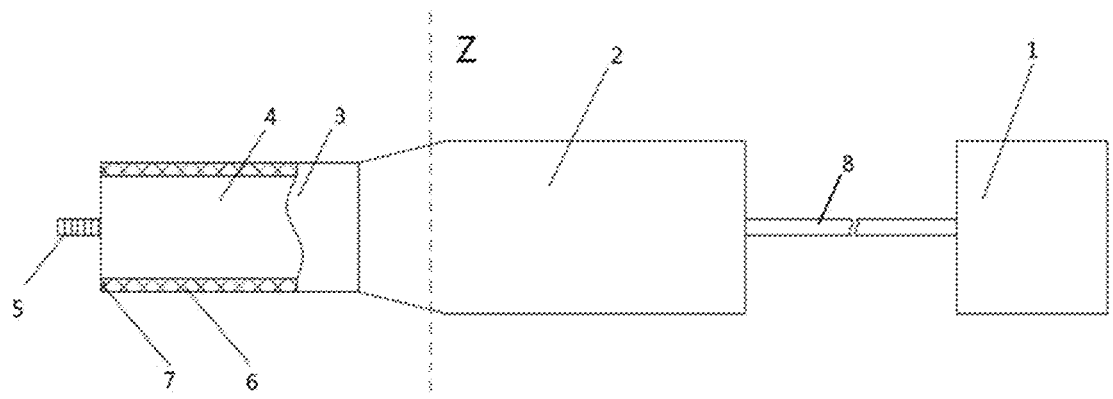
FIG. 1 is a schematic diagram of the ultrasonic generating device and the transmission device.

In the drawings: Z. ultrasonic generating device, 1. ultrasonic generator, 2. transducer, 3. transmission device (main body), 4. transmission device (forepart), 5 fixedly-connected device, (external thread) 6. annular storage device, 7. Lockable opening, 8. connecting device/connecting cable, 9. fixedly-connected device, 10. internal thread, 11. outer ring, 12. locking device/locking bolt, 13. locking device/locking screw hole, 14. inner ring, 15. outer ring locking device/locking buckle, 16. anti-sticking coating, 17. rubber band/anti-sticking coating, 18. protection structure, 19. positioning cylinder, 20. flange, 21. first annular contact surface, 22. ventilation channel, 23. main frame, 24. cutting device, 25. second annular contact surface, 26. driving device, 27. upper housing 28. lower housing, 29. locking ring, a. Spring, b. Pin, c. fixed annular knife holder, d. Inner ring bracket, e. Inner ring pad, f. Adjustable annular knife holder, g. adjustable annular knife, h. Ultrasonic vibration device, i. mist generator, j. vibration annular knife, k. first scissor annular knife supportor, l. second scissor annular knife supportor, m. inner ring bracket, n. inner ring pad, o. The first annular knife, p. The second annular knife, q. the first ultrasonic vibrator, r. the second ultrasonic vibrator, s. Adjustable scissors annular knife, (semi-annular knife, quarter-annular knife), t. Ultrasonic vibrated scissor annular knife (semi-annular knife, quarter-annular knife), u. Inner ring bracket, v. Inner ring pad, A. the first outer ring (fixed outer annular knife), B. the second outer ring (adjustable outer annular knife), C. inner ring frame, D. inner ring wall, E. ultrasonic vibrated generating device-annular knife buckle thread compound fixedly connector, F. ultrasonic vibration device, G. mist generator, H. restraint protection strap, I. first part of outer ring, J. second part of outer ring, K. inner ring bracket, L (L-1/L-2). Inner ring pad (first inner ring pad/second inner ring pad), M. ultrasonic vibration device, N. mist generator, 102-1. positioning cylinder, 102-2. flange, 102-3. first annular contact surface 102-4. first protection film, 102-5. Ventilation channel, 102-6. front support sleeve, 102-7. rear support sleeve, 102-8. annular knife, 102-9. annular knife holder, 102-10. second annular contact surface, 102-11. compression rod, 102-12. connecting rod, 102-13. Spring, 102-14. transducer, 102-15. annular storing device, 102-16. annular compression device, 102-17. export, 102-18. transition sleeve, 102-19. protection sleeve, 102-20. connecting sleeve, 102-21. Tightening piece.

DETAILED DESCRIPTION OF THE EMBODIMENTS

The present invention will be further description in details according to the accompanying drawings, which is one preferably embodiment of the various kinds embodiments of the present invention.

Referring to FIG. 1, FIG. 1 shows a preferred embodiment of the invention, an ultrasonic generating device Z includes an ultrasonic generator 1 and a transducer 2. The ultrasonic generator 1 is connected to the transducer 2 by a connecting device or connecting cable 8. The ultrasonic generating device Z is connected to a circumcision device through a transmission device. The transmission device includes a main body 3 of transmission device and a forepart 4. The end of the forepart 4 of the transmission device is provided with an external thread 5 of a fixedly-connected device. One side, two sides, or circumferential area of the forepart 4 o is provided with an annular storage device 6. A lockable opening 7 that can be closed is provided on the end of the annular storage device 6, wherein the end of the annular storage device 6 is close to the circumcision device.

The ultrasound subassembly for foreskin compressing, cutting, hemostasis and healing, which applies the ultrasound to the junction of an internal and an external tissue of a tip of humans for compressing, cutting, hemostasis and healing of foreskin, including the ultrasonic generating device Z, the transmission device 3, 4 and a circumcision device. The ultrasonic generating device Z is configured to generate ultrasound waves, which is connected to the transmission device 3, 4 and can transmit the ultrasound waves to the transmission device 3, 4. The transmission device 3, 4 is connected to the circumcision device and can transmit the ultrasound waves to the circumcision device, and the circumcision device is used to compress and/or cut the foreskin, and/or hemostasis and/or heal the wound.

A foreskin fixing end is connected to the transmission device 3, 4, and/or, an end of compressing or cutting or hemostasis or healing is connected to the transmission device 3, 4. The ultrasound transmitted by the transmission device 3, 4, is received and the foreskin is performed compressing and/or cutting, and/or, the wound is performed hemostasis and/or healed by the foreskin fixing end and/or the end of compressing or cutting or hemostasis or healing. The transmission device 3, 4 is fixedly connected to the foreskin fixing end and/or the end of compressing or cutting or hemostasis or healing thought the internal and external thread 5, 10, or a buckle.

The foreskin fixing end and the end of compressing or cutting or hemostasis or healing are fitted with an inner plate and an outer plate of the foreskin to clamp the foreskin, the clamping degree is the 9%-87% of the thickness of the foreskin in the natural state.

The foreskin fixing end and the end of compressing or cutting or hemostasis or healing are fitted with the inner plate and outer plate of the foreskin to hold the foreskin, wherein the holding force is 0.02-3.5 N/mm.

The present invention further includes a water mist generator 6, 7, which is used for adding water and/or water mist to the circumcision and/or circumcision position before the circumcision is performed, and/or during the circumcision is performing, and/or after circumcision is performed. The water mist generator 6, 7 is provided separately with respect to the ultrasonic generating device Z, the transmission device 3, 4 and the circumcision device; and/or, the water mist generator 6, 7 is partially or wholly integrated with the ultrasonic generating device Z, the transmission device 3, 4 and the circumcision device.

The present invention further includes a protection device, which is used for protecting the penis, glans, and/or the foreskin needed to be retained before the circumcision is performed, during the circumcision is performing, and/or after the circumcision is performed. The protection device is a protection structure 18 provided on the position of the circumcision device where contacting with the penis, glans, and/or the foreskin needed to be retained.

The ultrasonic generating device includes the ultrasonic generator 1 and the ultrasonic transducer 2. The ultrasonic generator 1 is driven connected to the ultrasound transducer 2, and the ultrasound transducer 2 is connected to the transmitting apparatus 3, 4.

Figure 2:
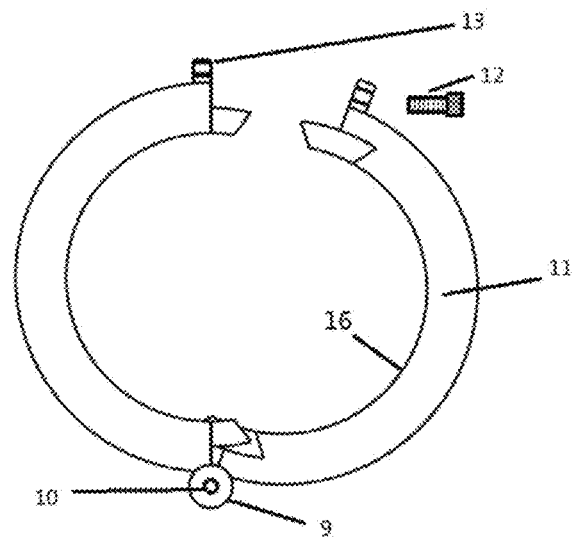
FIG. 2 is schematic diagram of the first form of the outer ring.

Referring to FIG. 2, in the preferred embodiment, an outer ring 11 of the circumcision device is provided with an opening, the opening can be closed by matching a locking bolt 12 with a locking screw hole 13. The outer ring 11 is provided with a fixedly-connected device 9. The fixedly-connected device 9 is provided with the internal thread 10, and the internal thread 10 and the external thread 5 can perform thread matching and fixedly connection. The inner side of the outer ring 11 is provided with an anti-adhesion coating 16.

The circumcision device comprises a first end and a second end. The first end is a foreskin fixing end, the second end is the end of compressing or cutting or hemostasis or healing. The foreskin fixing end and the end of compressing or cutting or hemostasis or healing are matched with each other to compress and/or cut the foreskin, and/or, to hemostasis or healing the wound. The matching way of the foreskin fixing end and the end of compressing or cutting or hemostasis or healing is that the foreskin fixing end is placed on the inner plate and the outer plate of the foreskin, the end of compressing or cutting or hemostasis or healing is placed on position corresponding to the position that the inner plate and the outer plate of the foreskin and the foreskin fixing end matched with. The foreskin fixing end and the end of compressing or cutting or hemostasis or healing respectively cooperate to clamp the foreskin on the inner and outer plates of the foreskin and used to compress and/or cut the foreskin, and/or, to hemostasis or healing the wound. The foreskin fixing end has a first annular contact surface, and the end of compressing or cutting or hemostasis or healing has a second annular contact surface. The first annular contact surface cooperates with the second annular contact surface so that the foreskin is placed between the first annular contact surface and the second annular contact surface. The first annular contact surface and the second annular contact surface are both closed circular contact surfaces.

The foreskin fixing end is the first ring, the end of compressing or cutting or hemostasis or healing is the second ring. The first ring and the second ring are arranged c to the inside and outside of the foreskin, or the second ring and the first ring are arranged the second annular contact surface to the inside and outside of the foreskin. The first ring is the inner ring 14, which is placed on the inside the foreskin, and the second ring is the outer ring 11, which is placed on the outside the foreskin, and the inner ring 14 and the outer ring 11 cooperate with each other to tightly clamp the foreskin. The inner ring 14 is a closed circular ring, and the outer ring 11 has opening, and the opening can be closed by the locking device 12, 13.

Figure 3:
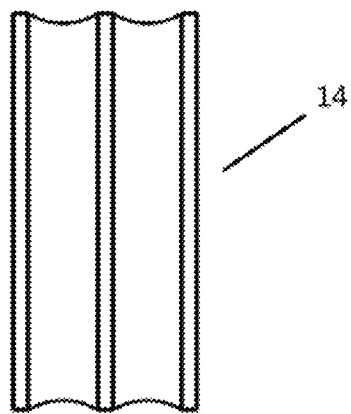
FIG. 3 is schematic diagram of the first form of the inner ring.
Figure 4:
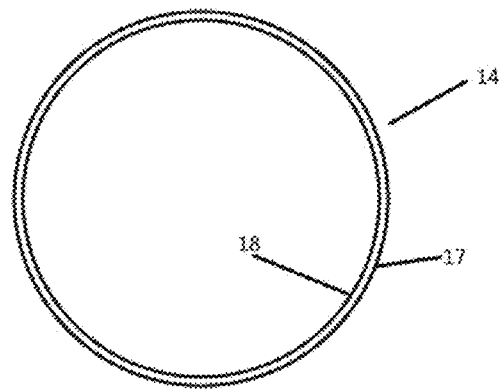
FIG. 4 is schematic diagram of the top view of the inner ring.
Figure 6:
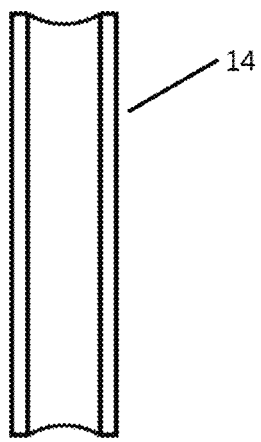
FIG. 6 is schematic diagram of the second form of the inner ring.

Referring to FIG. 3, in the preferred embodiment, FIG. 3 shows a form of the inner ring 14. The width of which is larger than that of the outer ring 11, and is provided with two parallel grooves, both of which can be engaged with the outer ring. Referring to FIG. 6, in this preferred embodiment, it is a form of the inner ring 14, the width of which is substantially the same as that of the outer ring 11 and can be engaged with the outer ring. Referring to FIG. 4, the outer loop of the inner ring 14 is provided with a rubber ring/ anti-adhesion coating 17, and the inner ring is provided with a protection structure 18.

Figure 7:
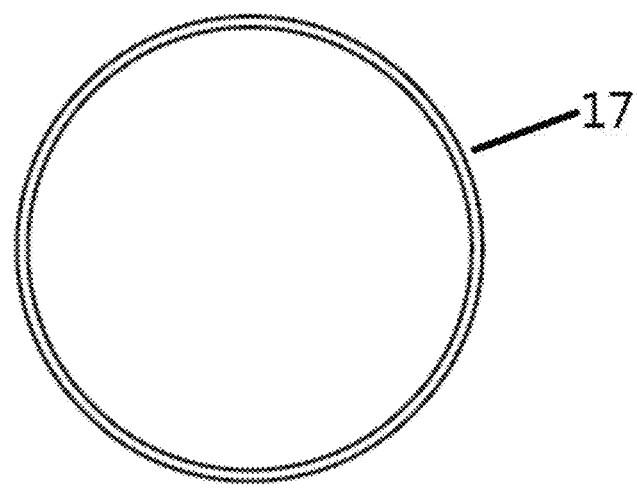
FIG. 7 is schematic diagram of the rubber band covering the outside the inner ring.

Referring to FIG. 7, the outer loop of the inner ring with the rubber ring or the anti-adhesion coating 17 is shown.

Figure 5:
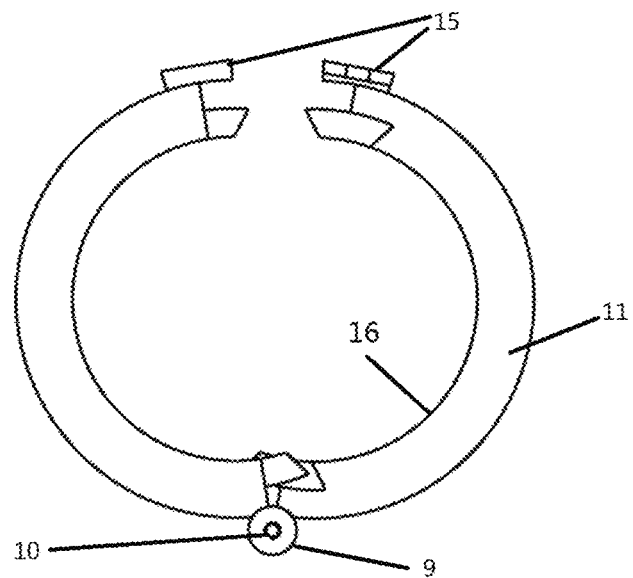
FIG. 5 is schematic diagram of the second form of the outer ring.

Referring to FIG. 5, in the preferred embodiment, the outer ring 11 of the circumcision device is provided with opening, the opening can be closed by locking buckle 15. The outer ring 11 is provided with a fixedly-connected device 9. The fixedly-connected device 9 is provided with the internal thread 10, and the internal thread 10 and the external thread 5 can perform thread matching and fixed connection. The inner side of the outer ring 11 is provided with an anti-adhesion coating 16.

In circumcision surgery, following steps are adopted:
1, measuring the circumference of the penis at 1 cm below the glans when the penis is not erected to determine the size and type of circumcision by a soft tape; fully wiping the inner and outer skin of the penis with sterilized cotton ball, spreading the surgical drapes, choosing the appropriate type of circumcision;
2, Annularly injecting the lidocaine anesthetic into the position of one third (⅓) from the glans to the root of the penis, with 3-5 ml of 2% lidocaine anesthesia for adult each time; with 2-3 ml of 2% lidocaine anesthesia for children each time;
3, using the rubber band to ligate the penis root, temporarily block the blood circulation after the anesthesia;
4, placing the inner ring in the foreskin of the glans, adjusting the position of the inner ring;
5, clamping of the edge of foreskin by using vascular forceps, inverting the foreskin to caught the inner ring, leaving frenulum for 1 cm;
6, checking whether the inner plate and outer plate are flat;
7. tightening the external thread end of the ultrasonic transmission device and the internal thread on the fixedly-connected device of the outer ring, starting the ultrasonic generator and performing the detection of each gear position of the ultrasonic generator in the water tank before surgery begins, turning off the ultrasonic generator after the detection is completed;
8, pressing the outer ring into the inner ring where the redundant foreskin located, checking the lateral surface of the inner and outer rings to keep the lateral surface of the inner and outer rings to horizontal, and closing the outer ring: closing the outer ring leaded by the junction of the outer ring the outer ring is closed by closing the junction of the outer ring?, and preliminary lock—the outer ring with a locking device; adjusting the foreskin to a suitable position, then the outer ring is completely buckled by the locking device;
9, starting the ultrasonic generating device and using high-frequency cutting gear to cut the foreskin, and at the same time, starting the water mist generator to spry the water mist to the circumcision site;
10, according to the actual situation of the foreskin, continuously cutting the foreskin (usually 3-9s), when the cutting is completed, the wound surface is contacted with the side surface (blunt surface) of the circumcision device; using low-frequency clotting gear to stop bleeding and achieve the primary healing;
11, remove the outer ring;
12, retreating the inner ring slowly to the root of the penis;
13, cutting the inner ring in two pieces with a sharp cut, and removing the inner ring to complete the operation.

Alternatively, the following optional steps are preferably used:
1, putting the inner ring in the position between the glans and inner plate of foreskin and locating the approximate position according to the length of circumcision;
4, tightening the external thread end of the ultrasonic transmission device and the internal thread on the fixedly-connected device of the outer ring, starting the ultrasonic generating device and performing the detection of each gear position of the ultrasonic generating device in the water tank before surgery begins, turning off the ultrasonic transmission device after the detection is completed;
5, closing the outer ring after matching the outer plate of the foreskin with the inner ring: closing the outer ring by closing the junction of the outer ring, and preliminary lock the outer ring with a locking device; after adjusting the foreskin to satisfaction position, buckling completely by the locking device;
9, start the ultrasonic generating device and using high-frequency cutting gear to cut the foreskin;
10. according to the actual situation of the foreskin, continuously cutting the foreskin (usually 3-9s); when the cutting is completed; the wound surface is contacted with the side surface (blunt surface) of the circumcision device, using low-frequency clotting gear to stop bleeding and achieve the primary healing;
11, remove the outer ring;
12, removing the inner ring, completing the operation.

According to one embodiment of the present invention, there is provided an ultrasound subassembly for compressing, cutting, hemostasis and healing of foreskin, includes an ultrasonic generating device, a transmission device and a circumcision device. The ultrasonic generating device is configured to generate ultrasonic waves. The ultrasonic generating is connected to the transmission device and can transmits the ultrasonic waves to the transmission device. The transmission device is connected to the circumcision device and can transmits the ultrasonic waves to the circumcision device, and the circumcision device is used to compress and/or cut the foreskin, and/or to stop bleeding and/or heal the wound.

The circumcision device in the present embodiment includes: a positioning cylinder configured to partially insert a glans into the positioning cylinder. At least one ventilation channel can be provided on the positioning cylinder. A distal end of the positioning cylinder is radially outwardly protruded to form a flange. A first annular contact surface is formed on the proximal end surface of the flange, the redundant foreskin is supported on the first annular contact surface after crossing the flange. In the positioning cylinder, the angle between the first annular contact surface and the axis of the positioning cylinder can be a right angle or an acute angle. The range of the acute angle can be from 30 to 60 degrees. In the positioning cylinder, the ventilation channel includes a groove extending in the axial direction outside the positioning cylinder. The groove keeps the interior space in communication with the outside. So that the pressure in the interior space is maintained substantially in balance with the outside pressure. In an alternative embodiment, the ventilation channel can also be a plurality of through-holes formed in the positioning cylinder through the wall thickness of the positioning cylinder. The through-hole can be various shape, for example, a circle, an oval, a triangle, a quadrangle, and other geometric structures.

The circumcision device in the present embodiment further includes a body frame, and the positioning cylinder is mounted in the body frame. A cutting device mounted on the body frame and further includes a second annular contact surface. The cutting device can be configured to be moved toward the positioning cylinder till the second annular contact surface is in contact with the first annular contact surface to compress, cut, stop bleeding, and heal the foreskin intervening therein.

According to another one embodiment of the present invention, there is provided an ultrasound subassembly for compressing, cutting, hemostasis and healing of foreskin, includes an ultrasonic generating device, a transmission device and a circumcision device. The ultrasonic generating device is configured to generate ultrasonic waves, which is connected to the transmission device and can transmits the ultrasonic waves to the transmission device. The transmission device is connected to the circumcision device and can transmits the ultrasonic waves to the circumcision device, and the circumcision device is used to compress and/or cut the foreskin, and/or to stop bleeding and/or heal the wound.

The circumcision device in the present embodiment includes: a positioning cylinder configured to be sleeved on the glans, and the first annular contact surface disposed at a proximal end of the positioning cylinder for supporting an redundant foreskin on the positioning cylinder. In the positioning cylinder, the angle between the first annular contact surface and the axis of the positioning cylinder can be a right angle or an acute angle. The range of the acute angle can be from 30 to 60 degrees. The positioning cylinder further includes a clamping band, wherein the clamping band is disposed on the periphery of the positioning cylinder for clamping the foreskin over the first annular contact surface to the outside of the positioning cylinder. The clamping band is provided with a plurality of ratchets that allow the clamping band to be clamped in one-way clamping.

The circumcision device in the present embodiment further includes a body frame, wherein the positioning cylinder is mounted in the body frame, and a cutting device mounted on the body frame. The circumcision device further includes a second annular contact surface. The cutting device can be configured to be driven to move toward the positioning cylinder till the second annular contact surface is in contact with the first annular contact surface to compress, cut, stop bleeding, and heal the foreskin intervening therein.

More preferably, according to one embodiment of the present invention, there is provided an ultrasound subassembly for compressing, cutting, hemostasis and healing of foreskin, comprises an ultrasonic generating device, a transmission device and a circumcision device. The ultrasonic generating device is configured to generate ultrasonic waves, which is connected to the transmission device and can transmits the ultrasonic waves to the transmission device. The transmission device is connected to the circumcision device and can transmits the ultrasonic waves to the circumcision device, and the circumcision device is used to compress and/or cut the foreskin, and/or to stop bleeding and/or heal the wound.

Figure 8:
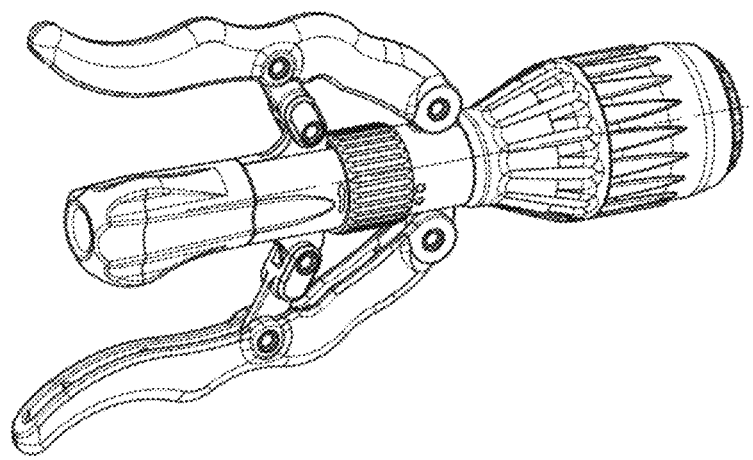
FIG. 8 is a front view of the introverted ultrasound subassembly for compressing, cutting, hemostasis and healing of foreskin of an embodiment of the present invention.

For better understanding, in the present embodiment, one end of the circumcision device and each component near the human body during the circumcision operation (for example, the right end as shown in FIG. 8) is referred to as a distal end, and one end of the circumcision device and each component away from the human body or near the operator (for example, the left end as shown in FIG. 8) is referred to as a proximal end.

Figure 10:
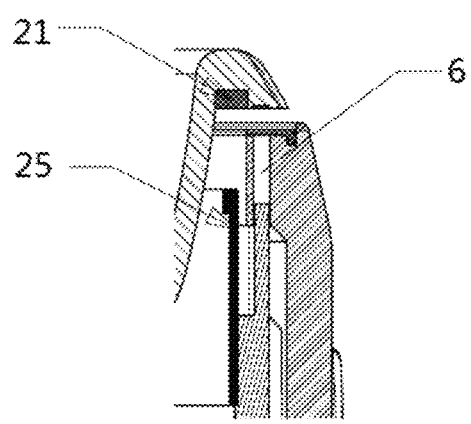
FIG. 10 is a partial enlarged view of the FIG. 9.
Figure 11:
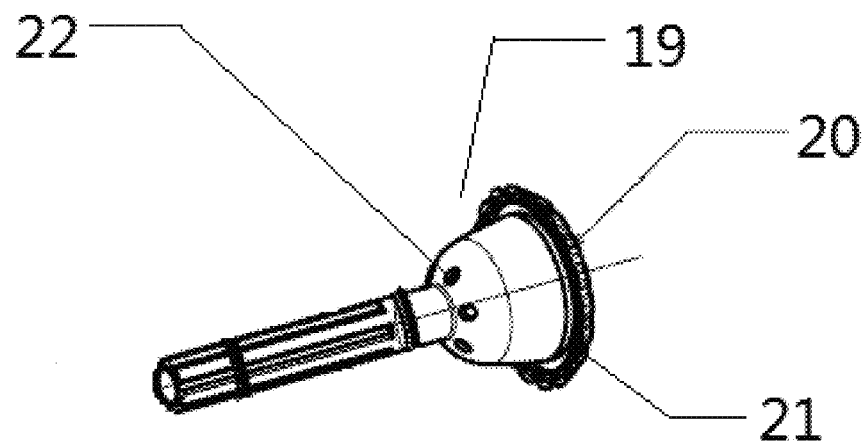
FIG. 11 is a front view of the positioning cylinder of the circumcision device shown in FIG. 8.
Figure 12:
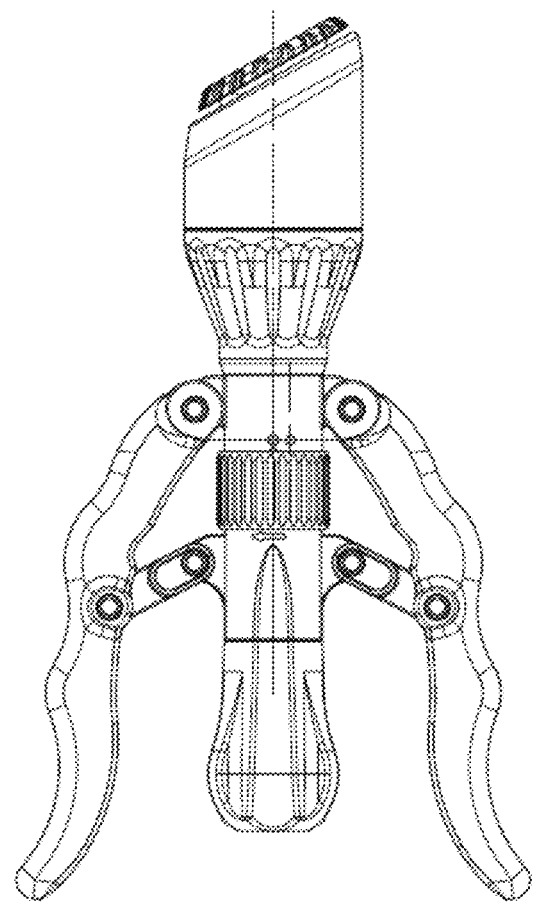
FIG. 12 is front view of the introverted ultrasound subassembly for compressing, cutting, hemostasis and healing of foreskin of another embodiment of the present invention.
Figure 13:
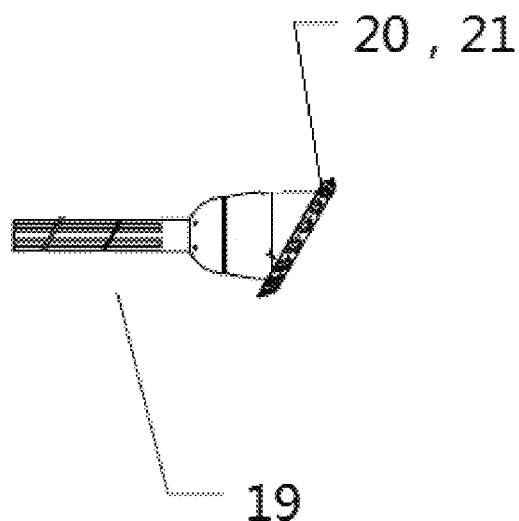
FIG. 13 is a front view of the circumcision device shown in FIG. 12.

Referring to FIG. 8 to FIG. 13, the circumcision device in the present embodiment includes: a positioning cylinder 19, configured to partially insert a glans into the positioning cylinder. A distal end of the positioning cylinder 19 is radially outwardly protruded to form a flange 20. A first annular contact surface 21 is formed on the proximal end surface of the flange, the redundant foreskin is supported on the first annular contact surface after crossing the flange 20 to form a structure that the distal end of the positioning cylinder disposed between the foreskin inner plate and the penis, which is called anintroverted structure. In the positioning cylinder, the angle between the first annular contact surface 21 and the axis of the positioning cylinder 19 can be a right angle or an acute angle. Referring to FIGS. 12-13, the range of the acute angle can be from 30 to 60 degrees, so as to matching the shape of the coronary sulcus of the glans, which is convenient to precise positioning. At least one ventilation channel 22 is provided in the positioning cylinder 19, and the ventilation channel 22 includes a groove extending in the axial direction outside the positioning cylinder 19. The groove keeps the interior space in communication with the outside, so that the pressure in the interior space is maintained substantially in balance with the outside pressure. In an alternative embodiment, the ventilation channel 22 can also be a plurality of through-holes formed in the positioning cylinder through the wall thickness of the positioning cylinder. For example, the through-holes can be, a circle, an oval, a triangle, a quadrangle, and other geometric structures.

The circumcision device in the present embodiment further includes a body frame 23, wherein the positioning cylinder 19 is mounted in the body frame 23. A cutting device 24 is mounted on the body frame 23 and further includes a second annular contact surface 25. The cutting device 24 can be configured to be moved toward the positioning cylinder 19 driven by a driving device 26 until the second annular contact surface 25 is in contact with the first annular contact surface 21 to compress, cut, stop bleeding, and heal the foreskin therebetween. The driving device can be a handle which is provided on the body frame and can be pressed, and the handle can be pressed to push the cutting device moving inside the body frame by external force, and to be reset by the rebound force of the spring after the surgery is completed.

Figure 9:
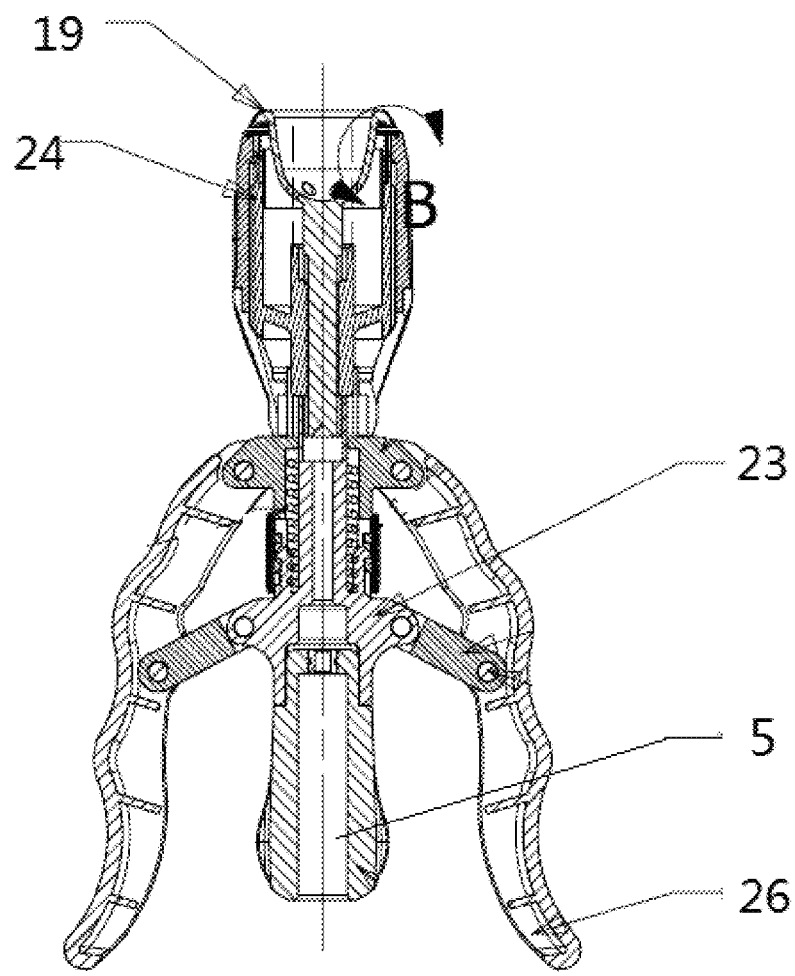
FIG. 9 is a sectional view of the FIG. 8.

Referring to FIG. 9 and FIG. 11, in the present embodiment, a positioning connecting rod can be extend from the proximal end of the positioning cylinder 19, and the positioning cylinder 19 is connected to the body frame though the positioning connecting rod.

The ultrasonic generating device in the present invention includes an ultrasonic generator 1 and a transducer 2. The generated ultrasonic waves are transmitted to the circumcision device by a main body 3 of the transmission device and a forepart 4 of the transmission device. The forepart of the transmission device can be connected to the positioning cylinder 19 of the circumcision device and/or the cutting device 24 through fixed-connected device 5, so that the ultrasonic waves are transmitted to the first annular contact surface 21 and/or the second annular contact surface 25. The fixed-connected device 5 can perform connection through internal and external thread or the buckle d.

In order to prevent adhesions between the foreskin and the circumcision device during surgery to cause re-tearing of the wound, the portion of the positioning cylinder and the cutting device wherein in contact with the foreskin is provided with the anti-adhesion coating 16 (not shown in the figures). Preferably, the anti-adhesion coating 16 is provided on the inside of the positioning cylinder, flange and the second annular contact surface of the cutting device.

In order to avoid generating smoke and smell when the circumcision is performed by using ultrasonic, and affecting the visual field and the surgical environment, the circumcision device of the present invention is further provided with a water mist generator. Referring to FIG. 10, the water mist generator can include the annular water storage device 6 provided on the body frame, wherein the annular water storage device 6 is located on the outer peripheral or inner periphery of the cutting device. A water outlet 7 (not shown in the figures) is provided on the side of the annular water storage device 6 facing the first annular contact surface 21. Water, alcohol, disinfectant and other liquids can be stored in the annular water storage device 6, and be sprayed by squeezing, pushing or ultrasonic vibration from the water outlet 7. Therefore, forming a water mist environment around the first annular contact surface 21 before the circumcision, during the circumcision and/or after the circumcision.

More preferably, according to another embodiment of the present invention, there is provided an ultrasound subassembly for compressing, cutting, hemostasis and healing of foreskin, comprises an ultrasonic generating device, a transmission device and a circumcision device. The ultrasonic generating device is configured to generate ultrasonic waves, which is connected to the transmission device and can transmits the ultrasonic waves to the transmission device. The transmission device is connected to the circumcision device and can transmits the ultrasonic waves to the circumcision device, and the circumcision device is used to compress and/or cut the foreskin, and/or to stop bleeding and/or heal the wound.

Figure 14:
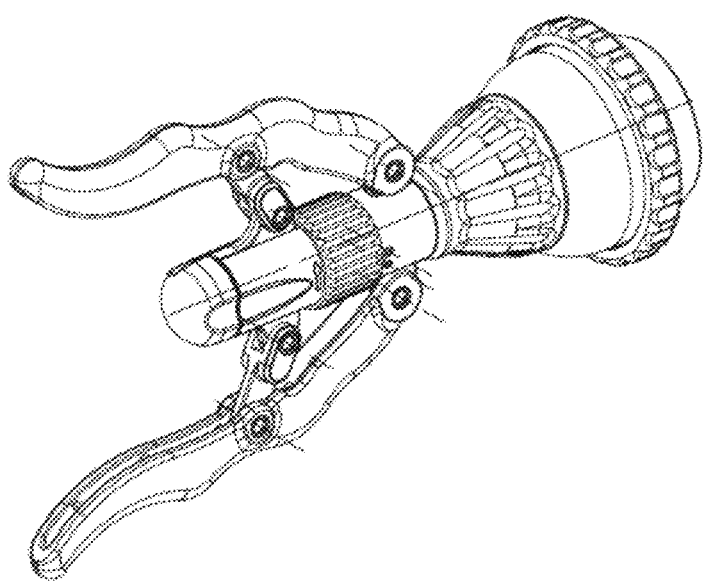
FIG. 14 is a front view of the inverted ultrasound subassembly for compressing, cutting, hemostasis and healing of foreskin of an embodiment of the present invention.

For better understanding, in the present embodiment, one end of the circumcision device and each component near the human body during the circumcision operation (for example, the right end as shown in FIG. 14) is referred to as a distal end, and one end of the circumcision device and each component away from the human body or near the operator (for example, the left end as shown in FIG. 14) is referred to as a proximal end.

A first annular contact surface 21 is formed on the proximal end surface of the flange, The circumcision device in the present embodiment includes: a positioning cylinder 19, which is configured to sleeve the glans, and the first annular contact surface 21 provided at the proximal end of the positioning cylinder. The first annular contact surface 21 is used to support the redundant foreskin on the proximal end of the positioning cylinder 19 after the glans crosses the positioning cylinder 19 to form a structure that the positioning cylinder as a whole is located outside the outer plate of the foreskin, which is called aninvert structure.

In the positioning cylinder 19, the angle between the first annular contact surface and the axis of the positioning cylinder can be a right angle or an acute angle. The range of the acute angle can be from 30 to 60 degrees, so as to matching the shape of the coronary sulcus of the glans, which is convenient to more precise positioning.

In the positioning cylinder, the positioning cylinder further includes a clamping band (not shown in the figures). The clamping band is disposed on the periphery of the positioning cylinder for clamping the foreskin over the first annular contact surface to the outside of the positioning cylinder. The clamping band is provided with a plurality of ratchets that allow the clamping band to be clamped in one-way clamping.

The circumcision device in the present embodiment further includes a body frame 23 wherein the positioning cylinder is mounted in the body frame, and a cutting device 24 mounted on the body frame, and the cutting device 24 further includes a second annular contact surface 25. The cutting device 24 can be configured to be moved toward the positioning cylinder by a driving device 26 until the second annular contact surface is in contact with the first annular contact surface to compress, cut, stop bleeding, and heal the foreskin therebetween. The driving device can be a handle which is provided on the body frame and can be pressed, the handle can be pressed to push the cutting device moving inside the body frame by external force, and to be reset by the rebound force of the spring after the surgery is completed.

Figure 15:
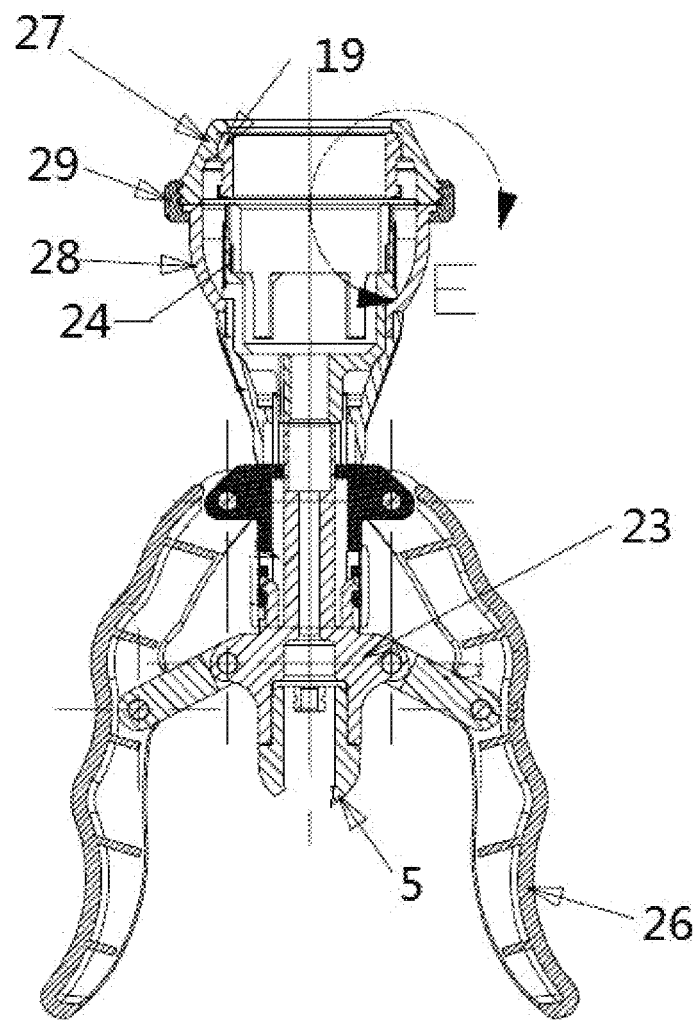
FIG. 15 is a sectional view of the FIG. 14.
Figure 16:
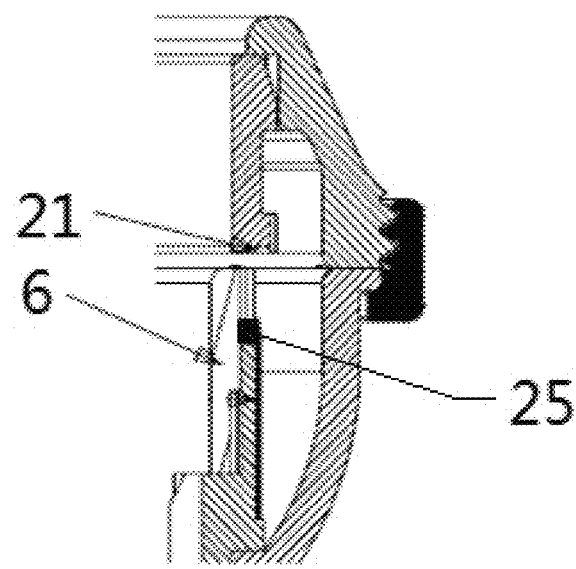
FIG. 16 is a partial enlarged view of the FIG. 15.
Figure 17:
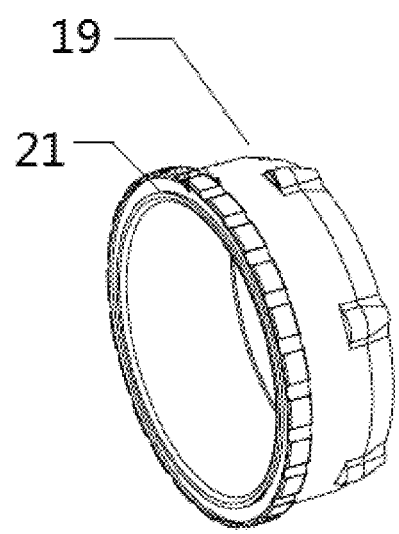
FIG. 17 is a front view of the circumcision device shown in FIG. 8.
Figure 18:
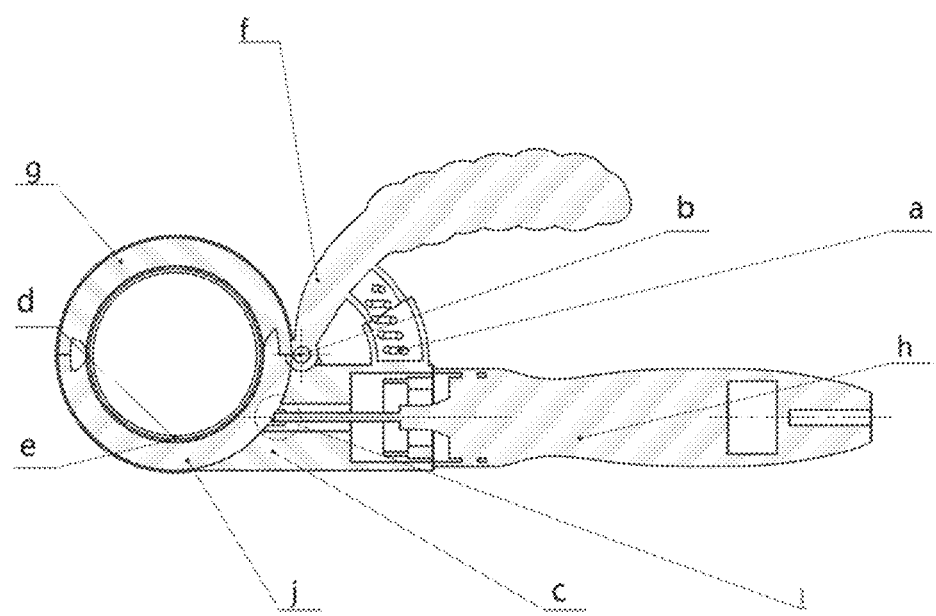
FIG. 18 is a sectional view of a pliers-type ultrasonic single-oscillation annular knife.
Figure 19:
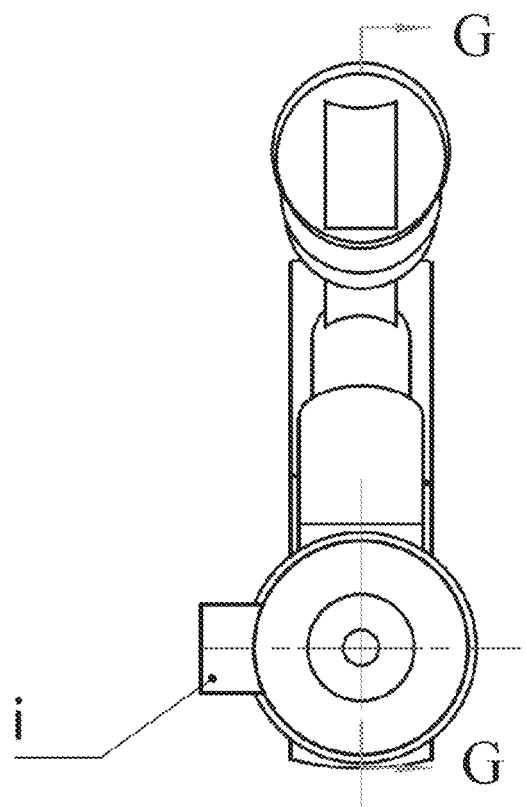
FIG. 19 is a bottom view of a pliers-type ultrasonic single-oscillation annular knife.
Figure 20:
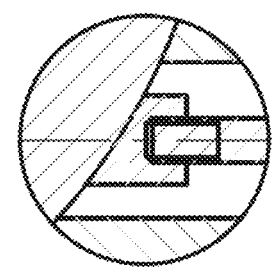
FIG. 20 is an enlarged view of the part I of the pliers-type ultrasonic single-oscillation annular knife shown in FIG. 18.
Figure 21:
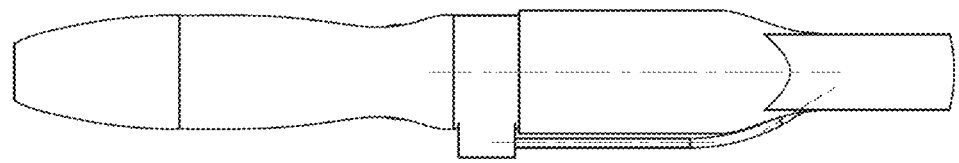
FIG. 21 is a first side view of the pliers-type ultrasonic single-oscillation annular knife.
Figure 22:
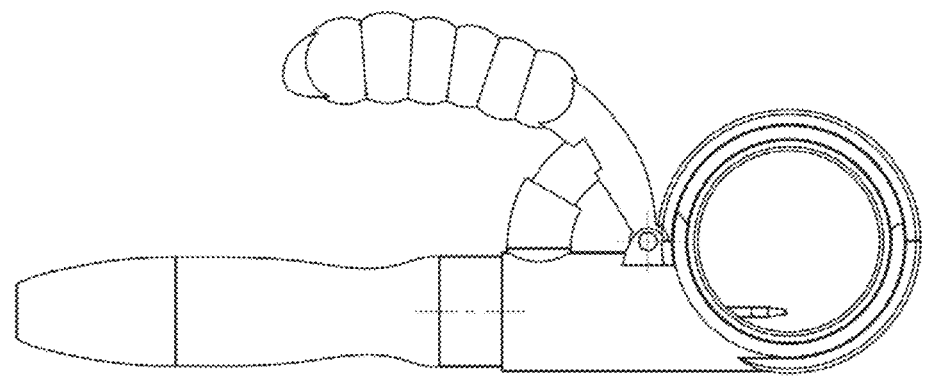
FIG. 22 is a top view of a pliers-type ultrasonic single-oscillation annular knife.
Figure 23:
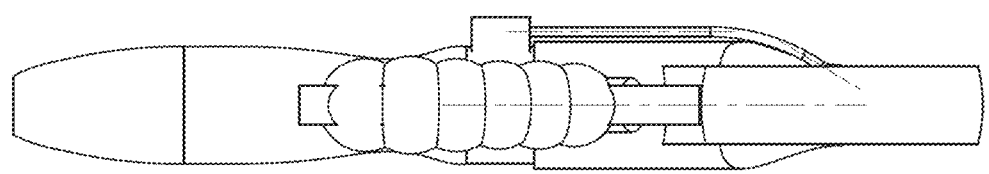
FIG. 23 is a second side view of the pliers-type ultrasonic single-oscillation annular knife.
Figure 24:
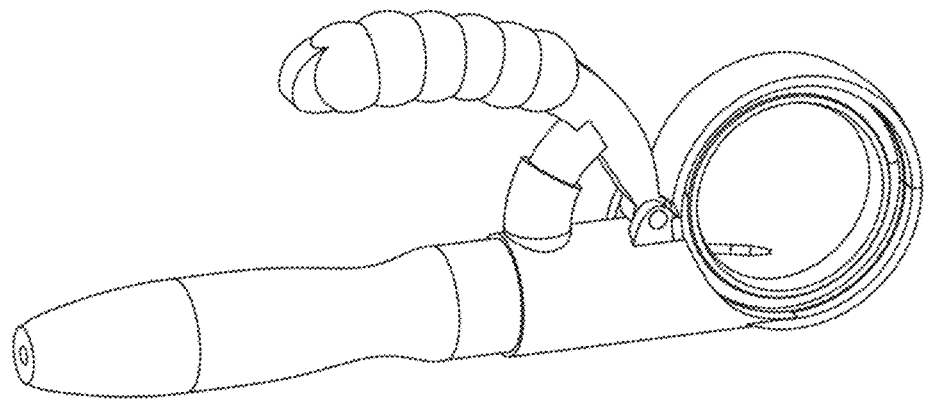
FIG. 24 is a perspective view of the pliers-type ultrasonic single oscillation annular knife.
Figure 25:
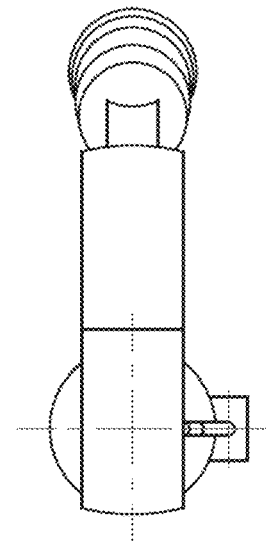
FIG. 25 is a view of top portion of the pliers-type ultrasonic single-oscillation annular knife.
Figure 26:
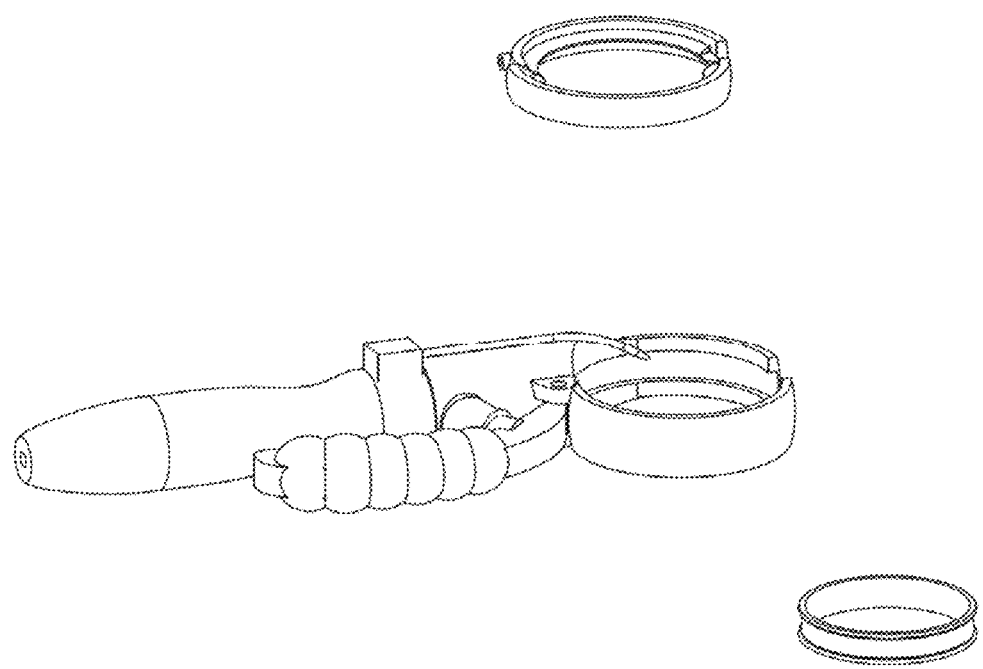
FIG. 26 is a first perspective view of the pliers-type ultrasonic single-oscillation annular knife.
Figure 27:
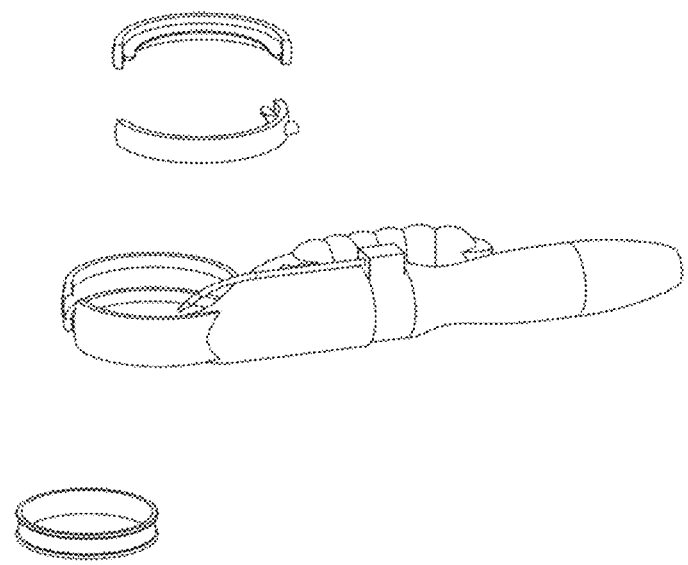
FIG. 27 is a second perspective view of the pliers-type ultrasonic single-oscillation annular knife.
Figure 28:
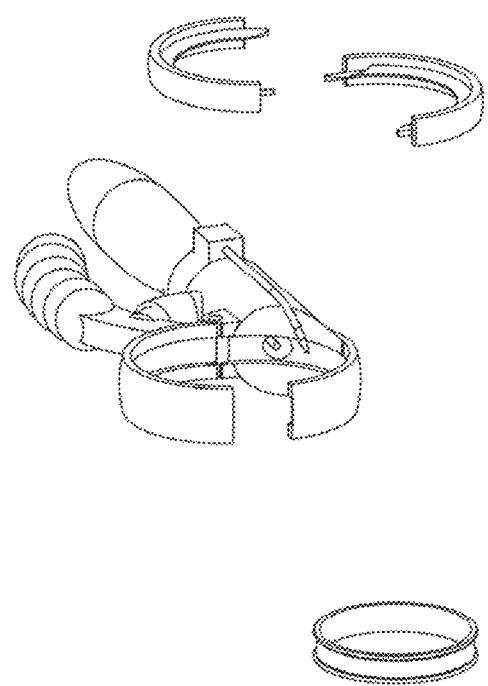
FIG. 28 is a third perspective view of the pliers-type ultrasonic single-oscillation annular knife.
Figure 29:
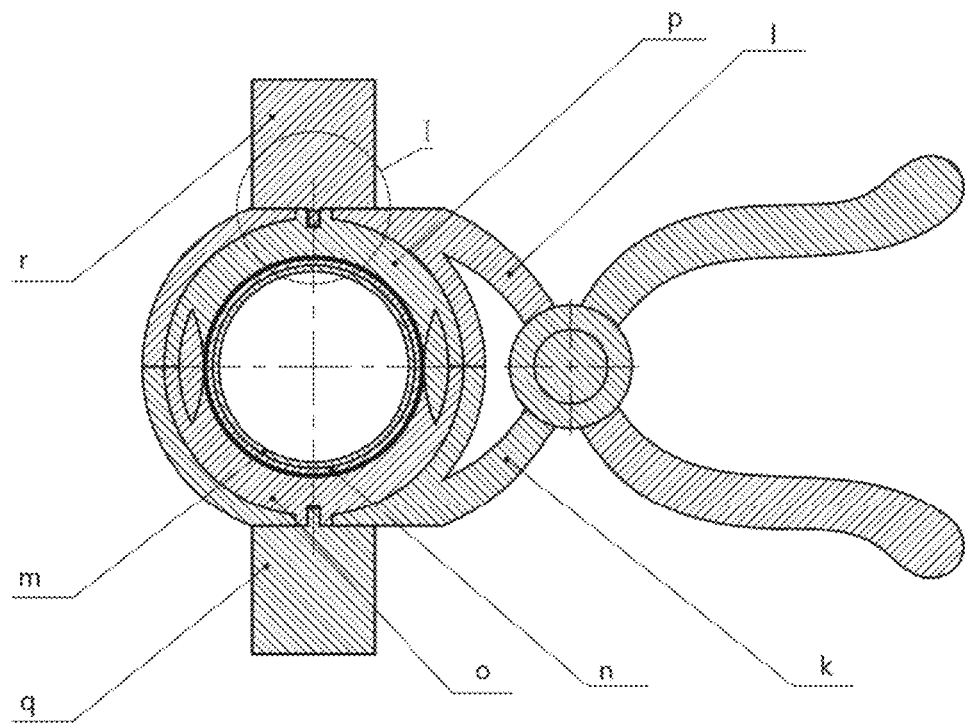
FIG. 29 is a sectional view of a pliers-type ultrasonic dual-oscillation annular knife.
Figure 30:
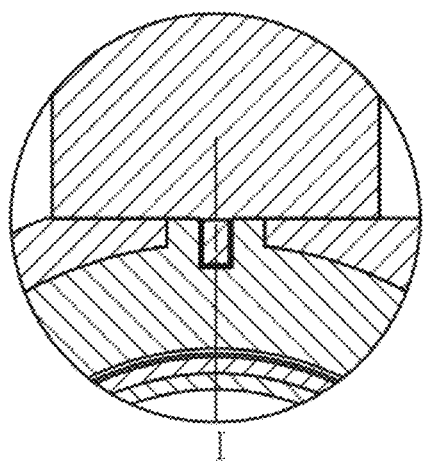
FIG. 30 is an enlarged view of the part I of the pliers-type ultrasonic dual-oscillation annular knife.
Figure 31:
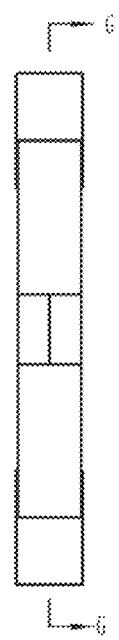
FIG. 31 is a view of top portion of the pliers-type ultrasonic dual-oscillation annular knife.
Figure 32:
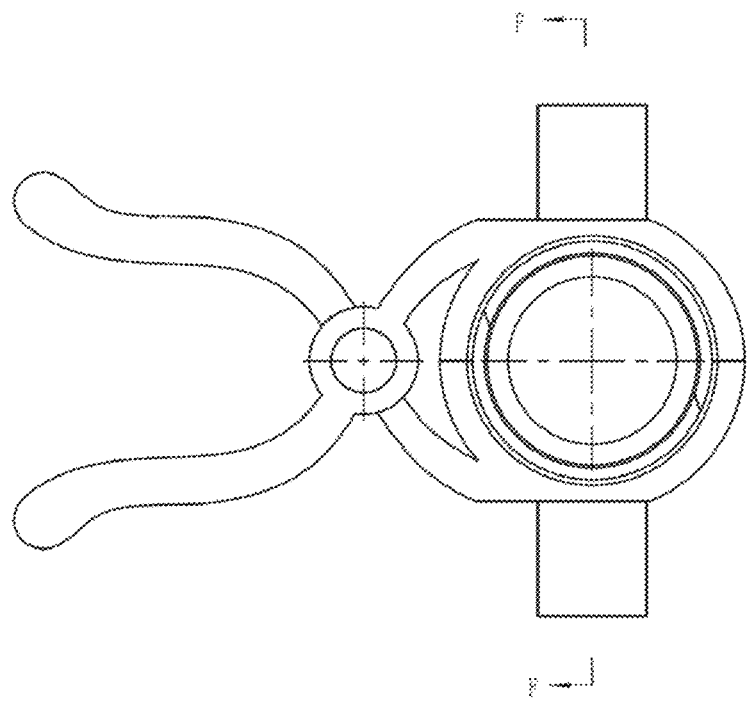
FIG. 32 is a top view of the pliers-type ultrasonic dual-oscillation annular knife.
Figure 33:
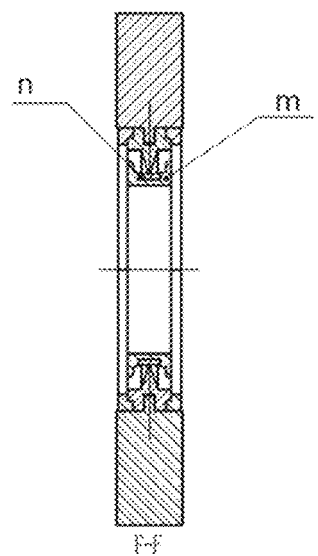
FIG. 33 is an F-F sectional view of the pliers-type dual-oscillation annular knife shown in FIG. 32.
Figure 34:
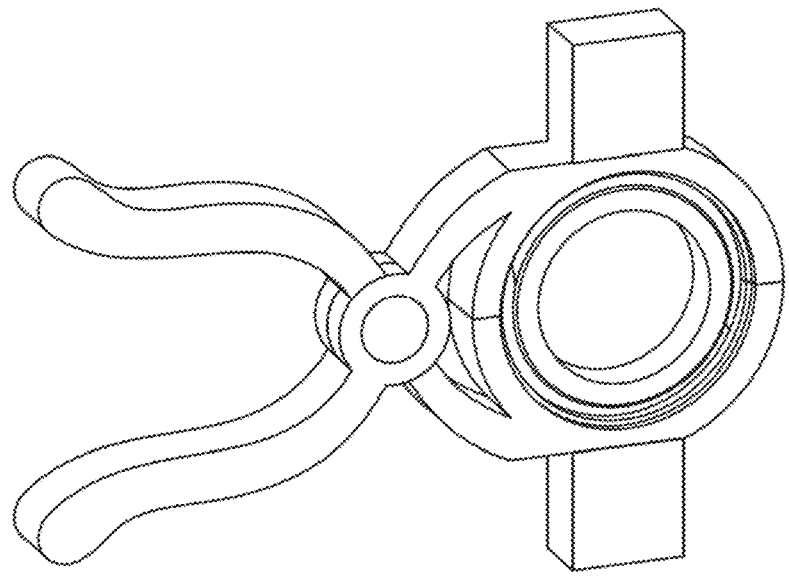
FIG. 34 is a perspective view of the pliers-type dual-oscillation annular knife.
Figure 35:
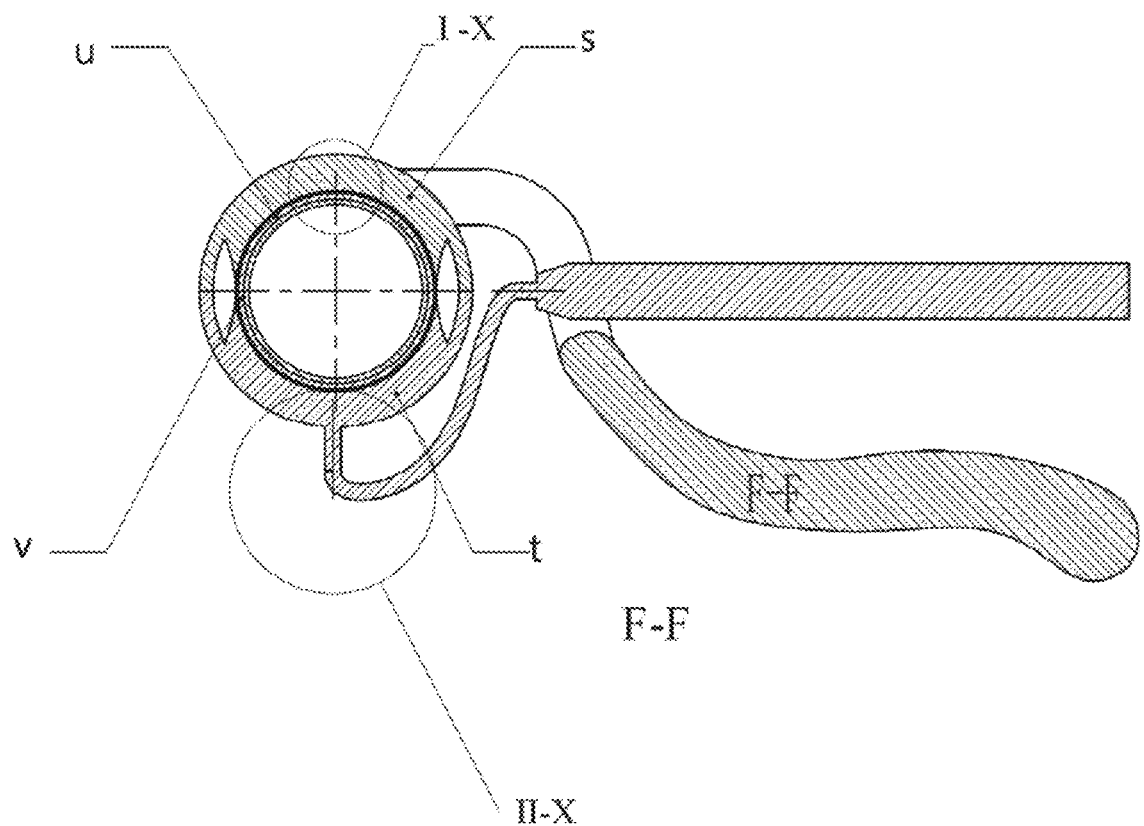
FIG. 35 is a sectional view of a direct-vibration shear annular knife system.
Figure 36:
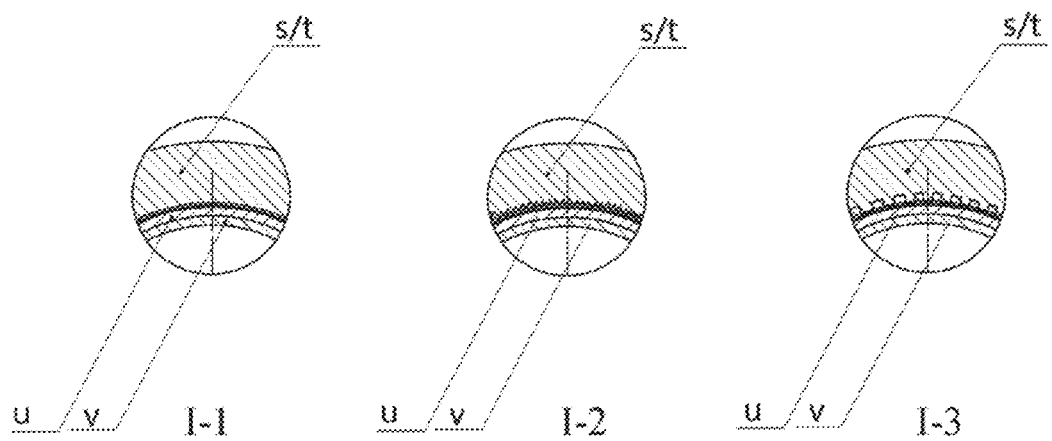
FIGS. 36A-36C are alternative schematic diagrams of I-X part of the direct-vibration scissor annular knife system shown in FIG. 35 (A-flat blade, B-triangle sawtooth blade, C-square sawtooth blade).
Figure 37:
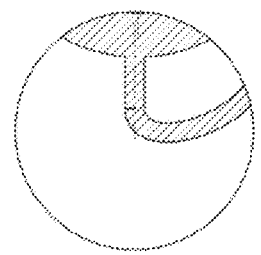
FIGS. 37A-37D are alternative schematic diagrams of II-X part of the direct vibration scissor annular knife system shown in FIG. 35 (A-Rigid connecting rod, outer annular knife, B-Screw fixed connecting rod, outer annular knife, C-Clasp fixed connecting rod, outer annular knife, D-buckle, thread compound fixed connecting rod, outer annular knife)
Figure 37:
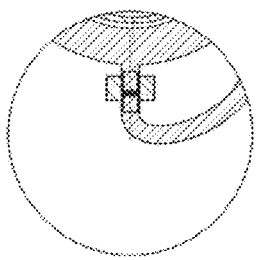
Figure 37:
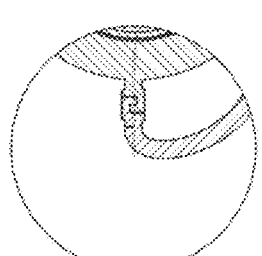
Figure 37:
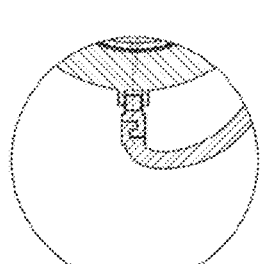
Figure 38:
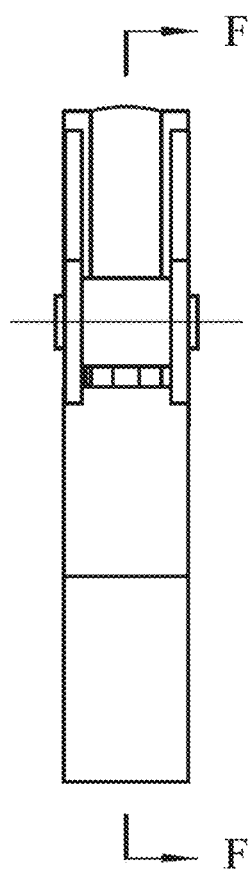
FIG. 38 is a view of a top portion of a direct-vibration scissor annular knife system.
Figure 39:
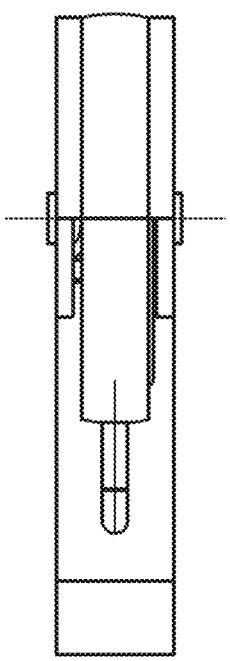
FIG. 39 is a view of a bottom portion of a direct-vibration scissor annular knife system.
Figure 40:
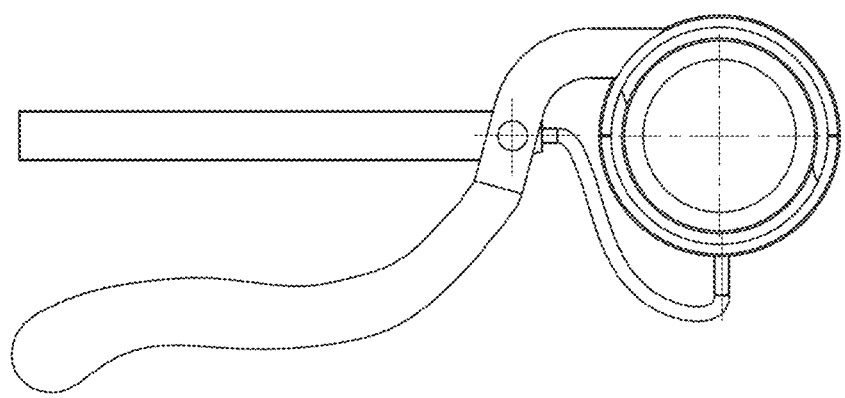
FIG. 40 is a top view of a direct-vibration scissor annular knife system.
Figure 41:
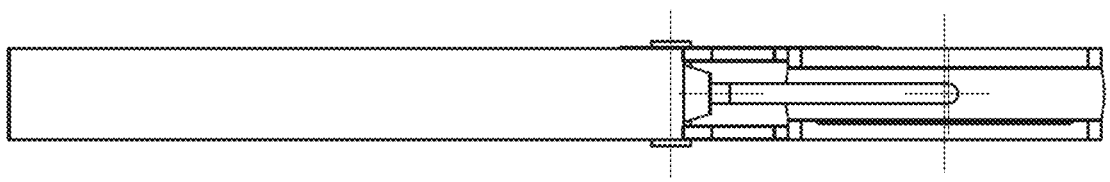
FIG. 41 is a first side view of a direct-vibration scissor annular knife system.
Figure 42:
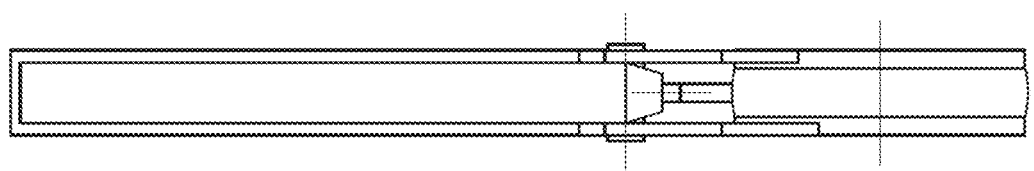
FIG. 42 is a second side view of a direct-vibration scissor annular knife system.
Figure 43:
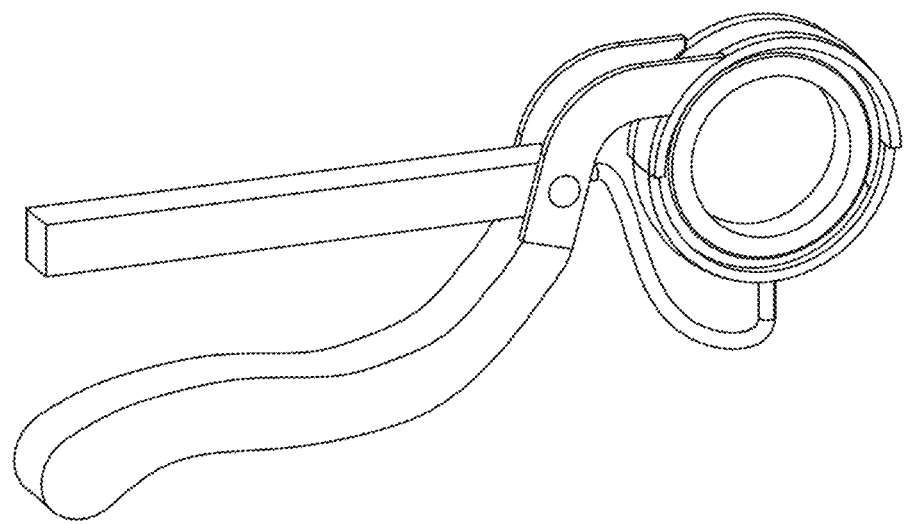
FIG. 43 is a first perspective view of a direct-vibration scissor annular knife system.
Figure 44:
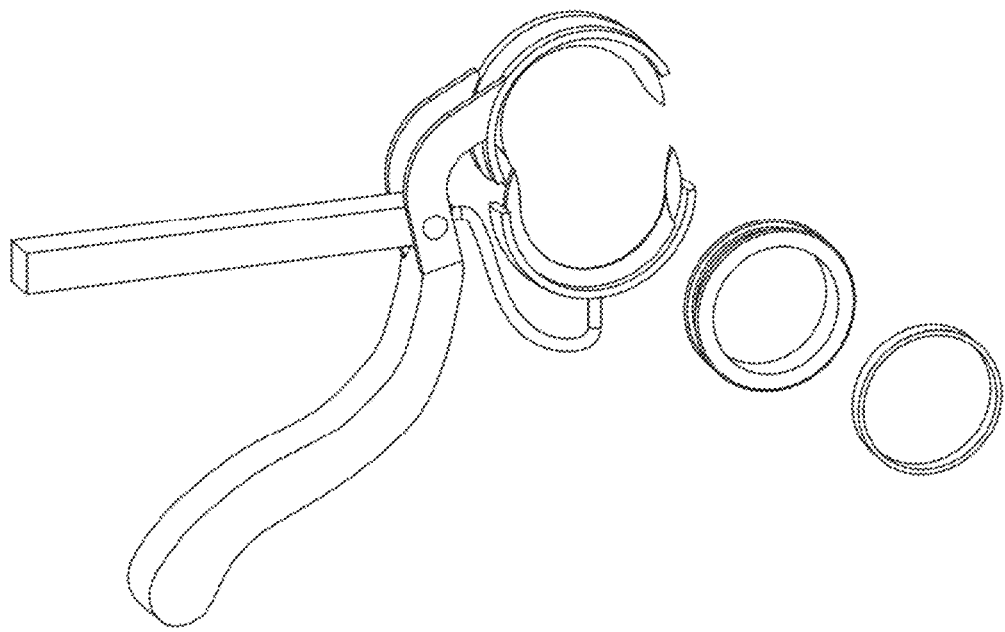
FIG. 44 is a second perspective view of a direct-vibration scissor annular knife system.
Figure 45:
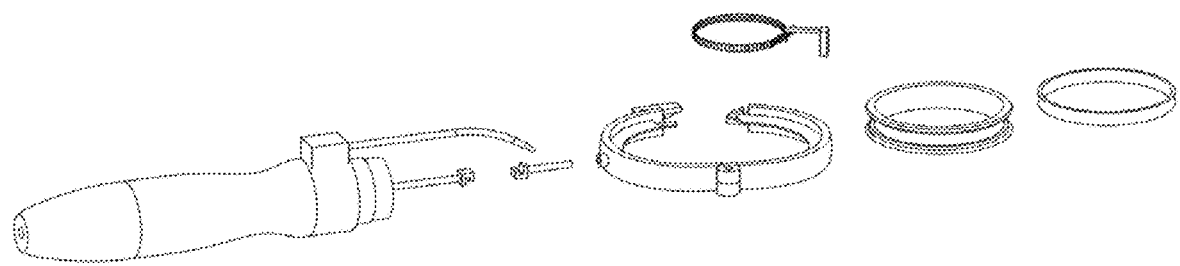
FIG. 45 is a decomposition diagram of an ultrasonic vibrating system using the buckle/thread compound connection of the ultrasonic vibrating rod and the outer annular knife (with protection device/restraint protection strap).
Figure 46:
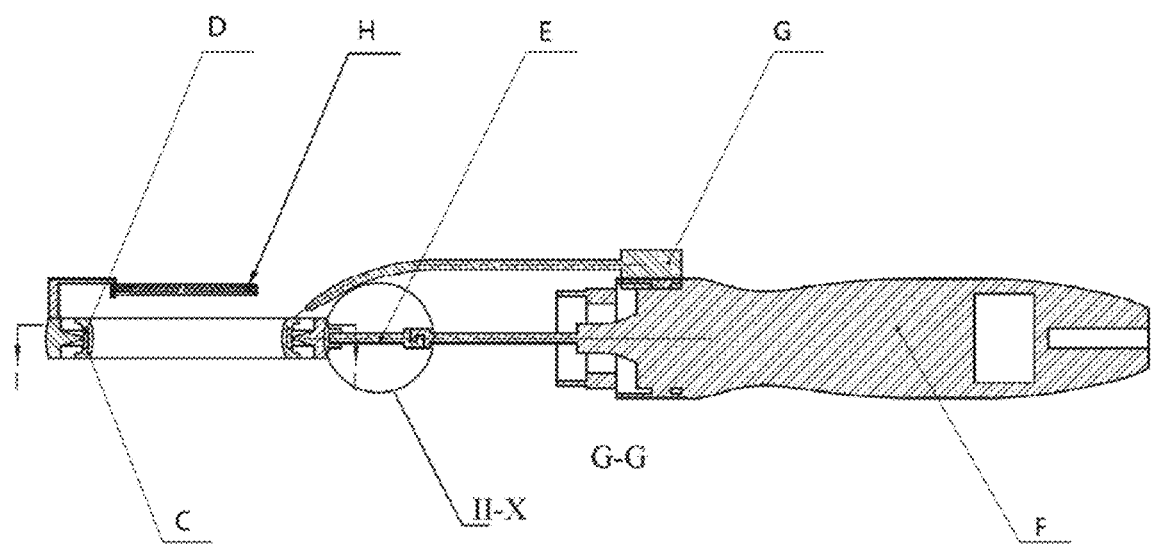
FIG. 46 is a sectional view from the side of an ultrasonic vibrating system using the buckle/thread compound connection of the ultrasonic vibrating rod and the outer annular knife (with protection device/restraint protection strap).
Figure 47:
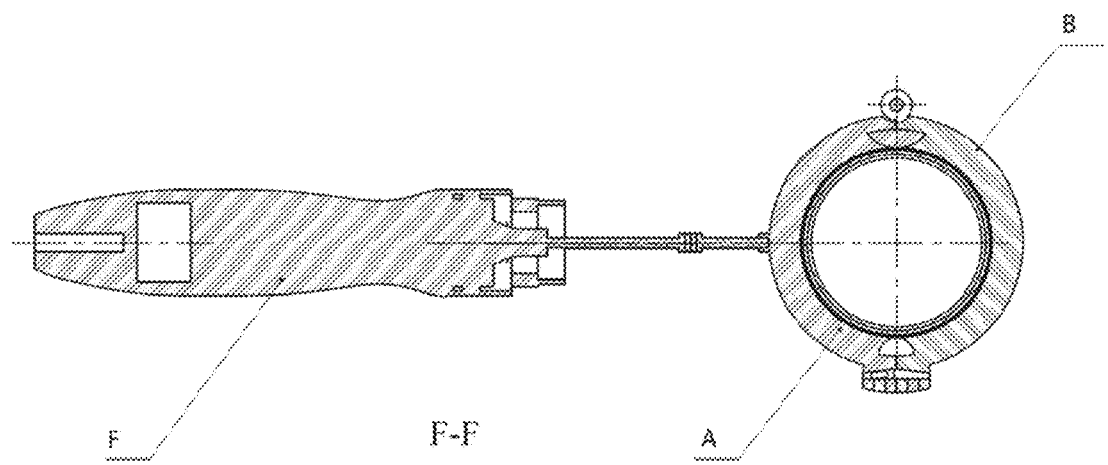
FIG. 47 is a sectional view from the front of an ultrasonic vibrating system using the buckle/thread compound connection of the ultrasonic vibrating rod and the outer annular knife (with protection device/restraint protection strap).
Figure 48:
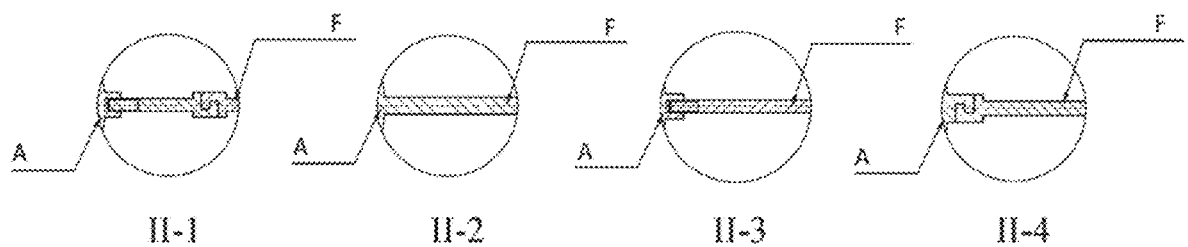
FIGS. 48A-48D are alternative connection schematic diagrams of the part II-X of an ultrasonic vibrating system using the buckle/thread compound connection of the ultrasonic vibrating rod and the outer annular knife (with protection device/restraint protection strap) shown in FIG. 46 (A-buckle, thread compound fixed connecting rod, outer annular knife, B-rigid connecting rod, outer annular knife, C-Screw fixed connecting rod, outer annular knife, D-Clasp fixed connecting rod, outer annular knife)
Figure 49:
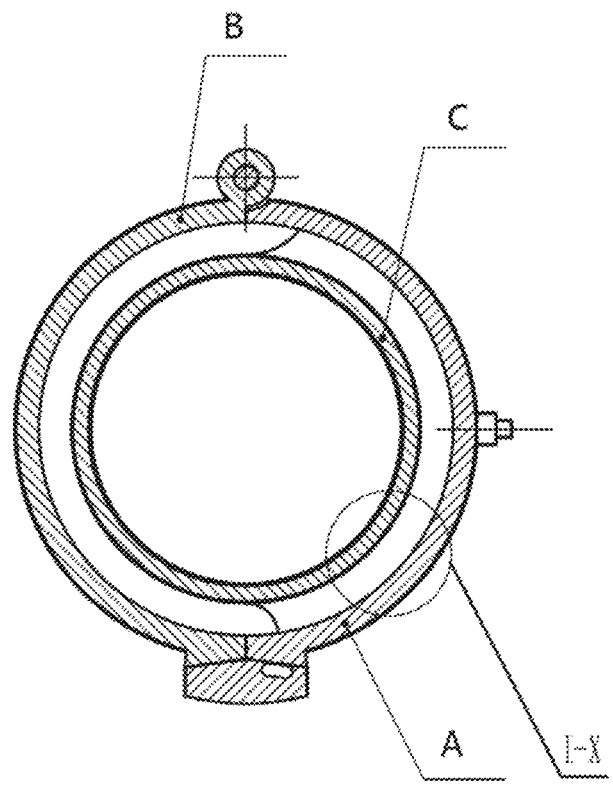
FIG. 49 is a schematic diagram of a handle-piece of an ultrasonic vibrating system using the buckle/thread compound connection of the ultrasonic vibrating rod and the outer annular knife (with protection device/restraint protection strap).
Figure 50:
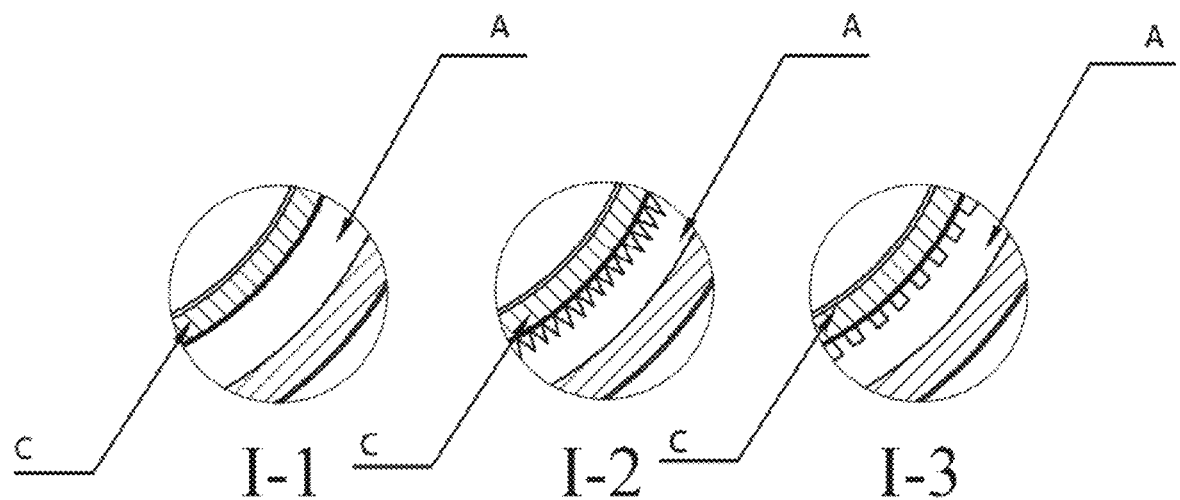
FIGS. 50A-50C are alternative schematic diagrams of I-X part of the ultrasonic vibrating system using the buckle/thread compound connection of the ultrasonic vibrating rod and the outer annular knife (with protection device/restraint protection strap) shown in FIG. 49 (A-flat blade outer ring, B-triangle sawtooth blade outer ring, C-square sawtooth blade outer ring).
Figure 51:
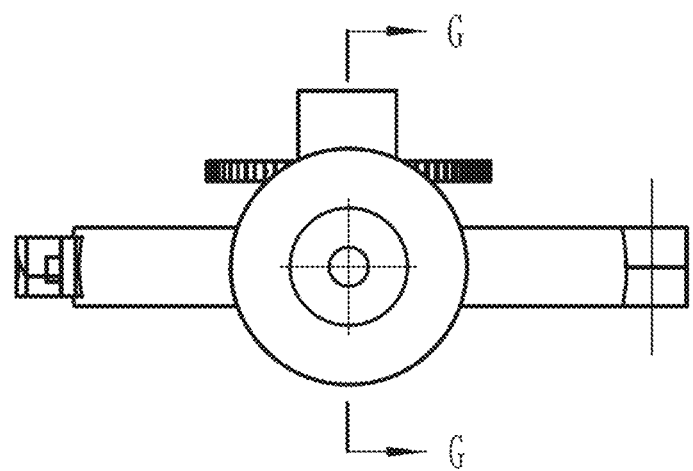
FIG. 51 is view of the top portion of the ultrasonic vibrating system using the buckle/thread compound connection of the ultrasonic vibrating rod and the outer annular knife (with protection device/restraint protection strap).
Figure 52:
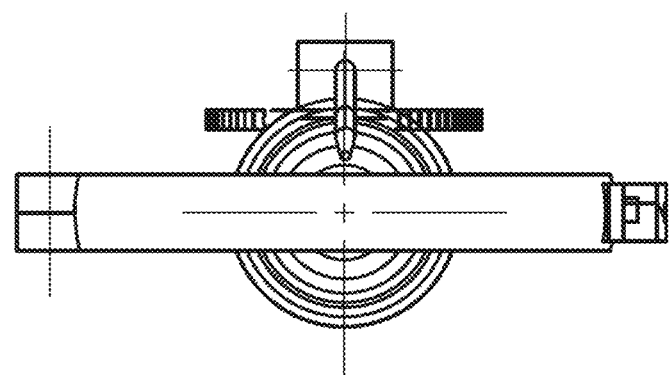
FIG. 52 is view of the bottom portion of the ultrasonic vibrating system using the buckle/thread compound connection of the ultrasonic vibrating rod and the outer annular knife (with protection device/restraint protection strap).
Figure 53:
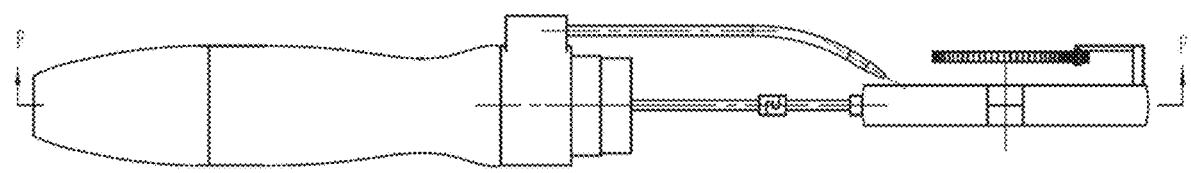
FIG. 53 is side view of the ultrasonic vibrating system using the buckle/thread compound connection of the ultrasonic vibrating rod and the outer annular knife (with protection device/restraint protection strap).
Figure 54:
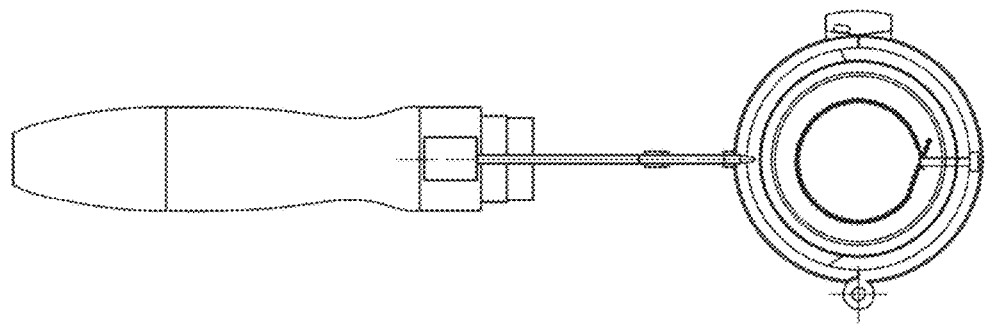
FIG. 54 is top view of the ultrasonic vibrating system using the buckle/thread compound connection of the ultrasonic vibrating rod and the outer annular knife (with protection device/restraint protection strap).
Figure 55:
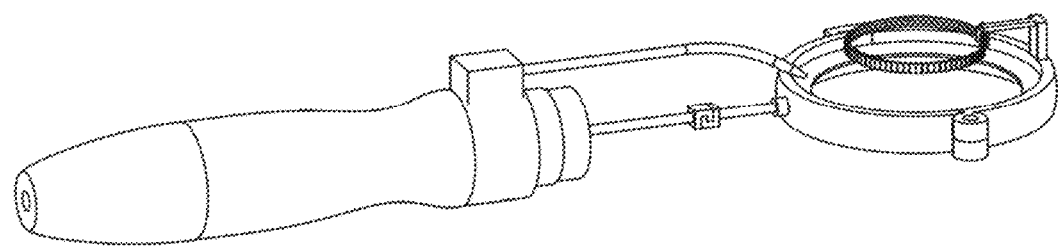
FIG. 55 is stereogram of the ultrasonic vibrating system using the buckle/thread compound connection of the ultrasonic vibrating rod and the outer annular knife (with protection device/restraint protection strap).
Figure 56:
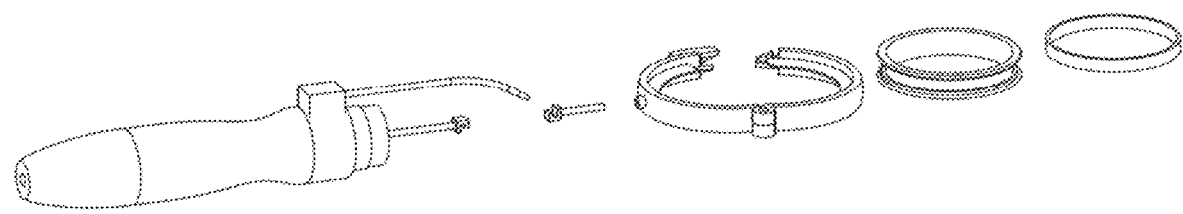
FIG. 56 is decomposition diagram of the ultrasonic vibrating system using a thread and buckle compound connection of the ultrasonic vibrating rod and the outer annular knife.
Figure 57:
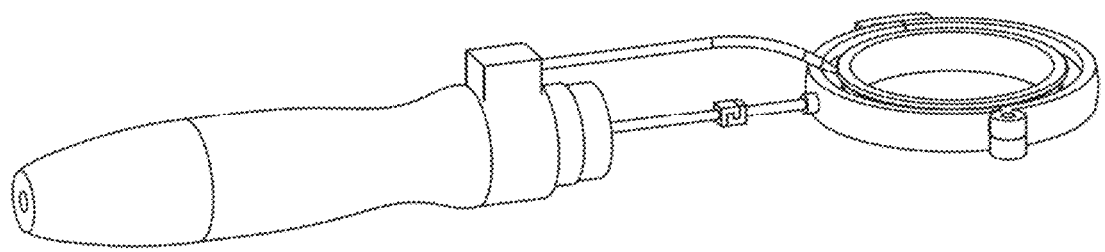
FIG. 57 is holistic diagram of the ultrasonic vibrating system using a thread and buckle compound connection of the ultrasonic vibrating rod and the outer annular knife.
Figure 58:
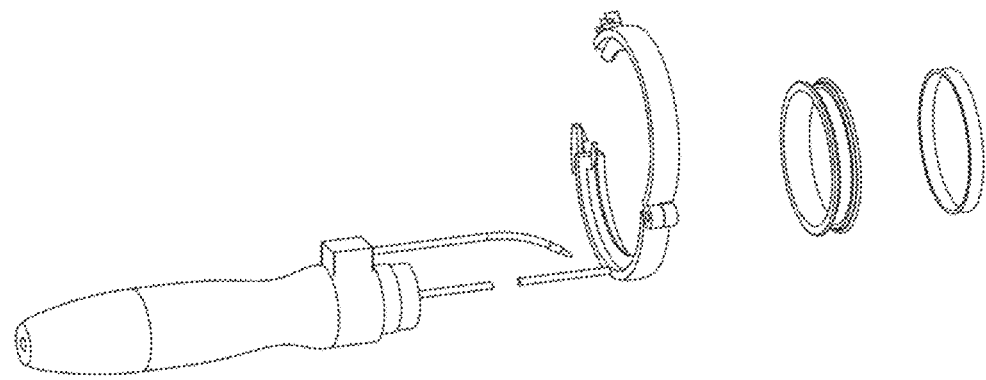
FIG. 58 is a decomposition diagram of the ultrasonic vibrating system wherein the ultrasonic vibrating system uses a rigid or integrated connection and is perpendicular between the ultrasonic vibrating rod and the outer annular knife.
Figure 59:
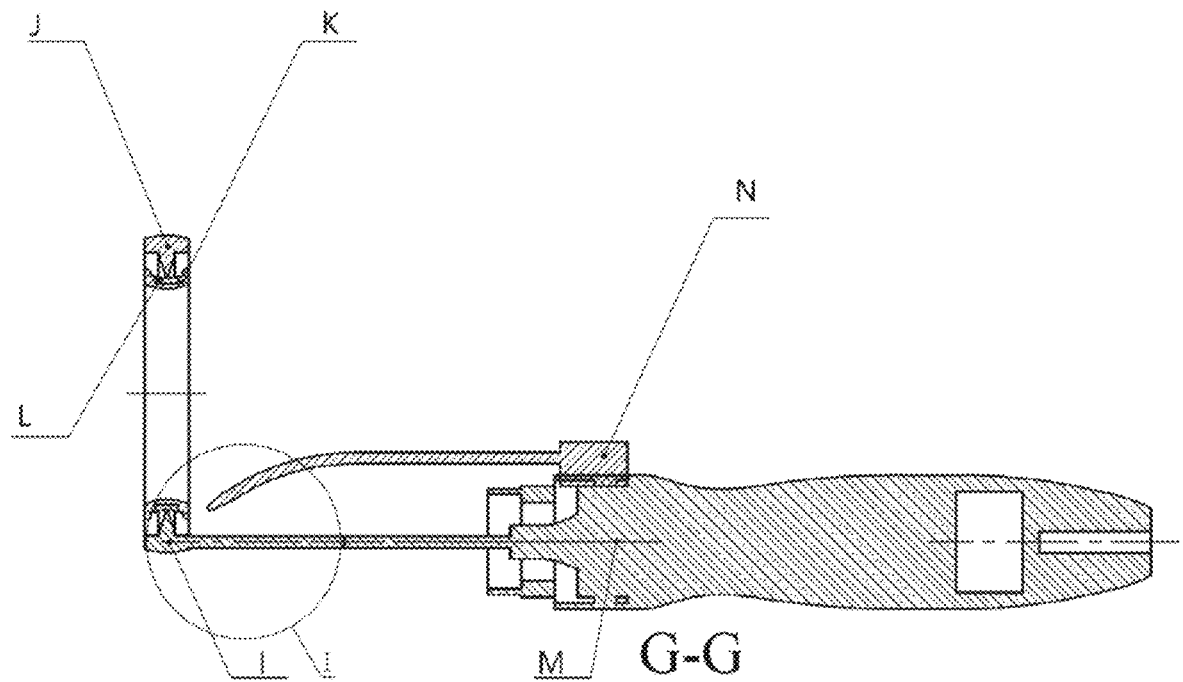
FIG. 59 is a sectional view of the ultrasonic vibrating system wherein the ultrasonic vibrating system uses a rigid or integrated connection and is perpendicular between the ultrasonic vibrating rod and the outer annular knife.
Figure 60:
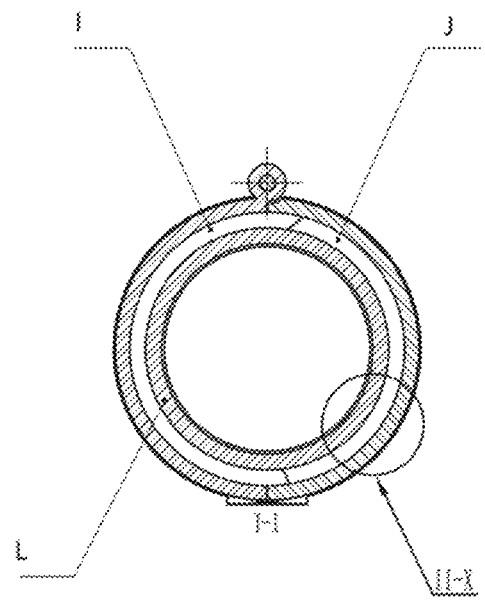
FIG. 60 is a schematic diagram of handlepiece of the ultrasonic vibrating system wherein the ultrasonic vibrating system uses a rigid or integrated connection and is perpendicular between the ultrasonic vibrating rod and the outer annular knife.
Figure 61:
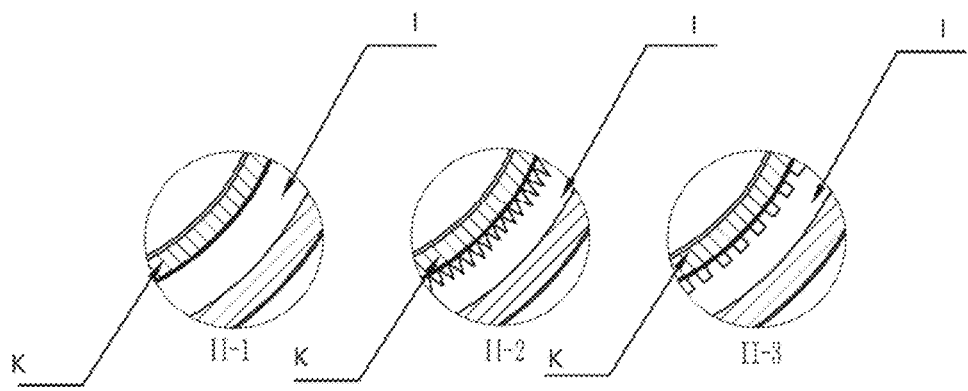
FIGS. 61A-61C are alternative schematic diagrams of II-X part shown in the FIG. 60. A-flat blade outer ring, B-triangle sawtooth blade outer ring, C-square sawtooth blade outer ring).
Figure 62:
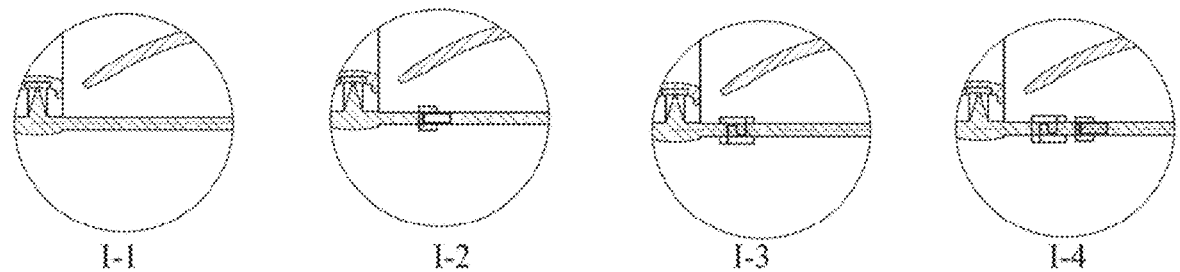
FIGS. 62A-62D are alternative schematic diagrams of I-X part shown in the FIG. 59 (A-Rigid connecting rod, outer annular knife, B-Screw fastener connecting rod, outer annular knife, C-Clasp fastener connecting rod, outer annular knife, D-Buckle, Thread compound fixed connecting rod, outer annular knife).
Figure 63:
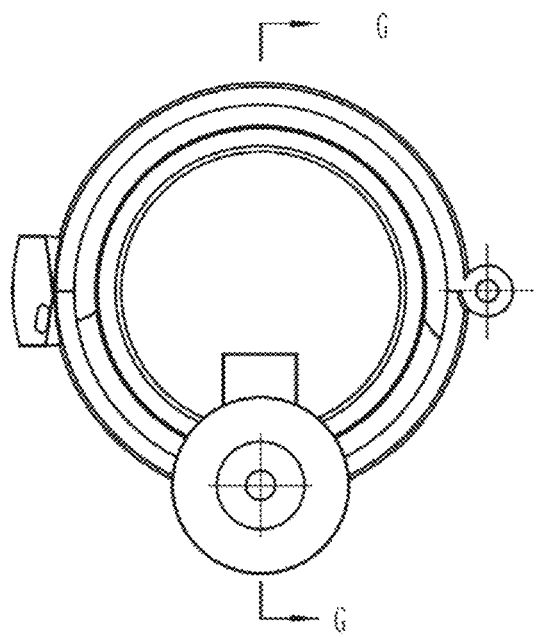
FIG. 63 is a view of the top portion of the ultrasonic vibrating system, wherein the ultrasonic vibrating system uses a rigid or integrated connection and is perpendicular between the ultrasonic vibrating rod and the outer annular knife.
Figure 64:
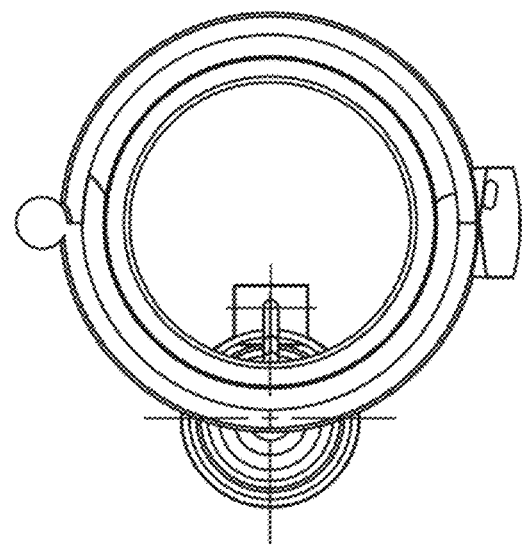
FIG. 64 is a view of the bottom portion of the ultrasonic vibrating system, wherein the ultrasonic vibrating system uses a rigid or integrated connection and is perpendicular between the ultrasonic vibrating rod and the outer annular knife.
Figure 65:
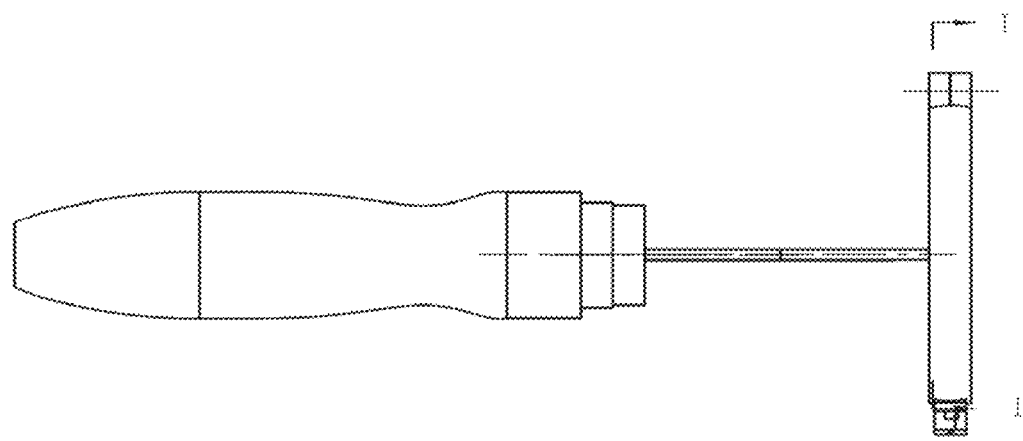
FIG. 65 is a bottom view of the ultrasonic vibrating system, wherein the ultrasonic vibrating system uses a rigid or integrated connection and is perpendicular between the ultrasonic vibrating rod and the outer annular knife.
Figure 66:
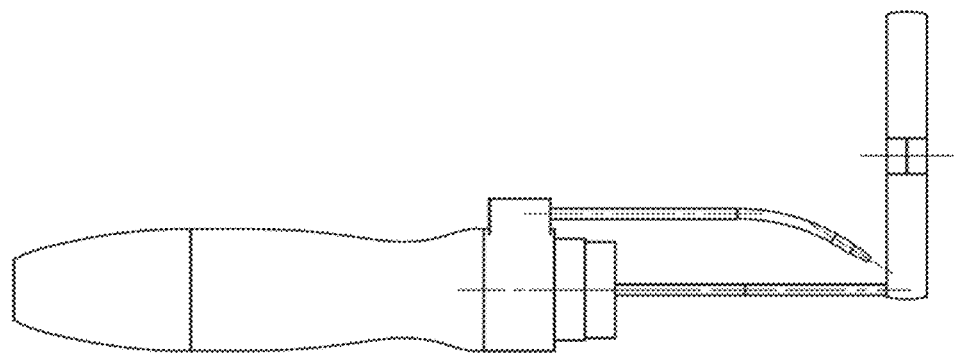
FIG. 66 is a side view of the ultrasonic vibrating system, wherein the ultrasonic vibrating system uses a rigid or integrated connection and is perpendicular between the ultrasonic vibrating rod and the outer annular knife.
Figure 67:
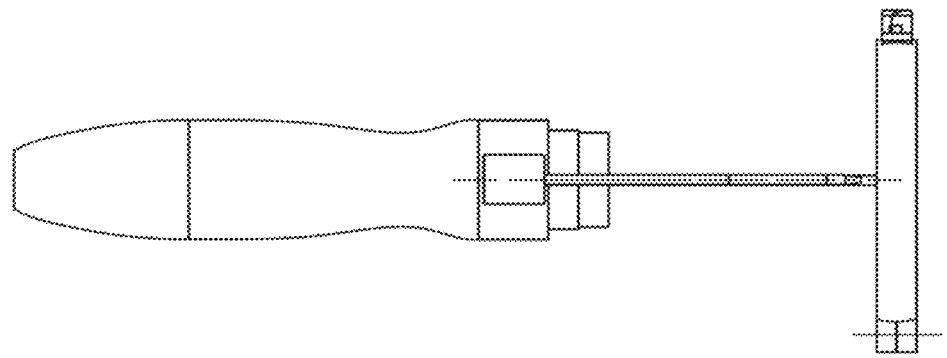
FIG. 67 is a top view of the ultrasonic vibrating system, wherein the ultrasonic vibrating system uses a rigid or integrated connection and is perpendicular between the ultrasonic vibrating rod and the outer annular knife.
Figure 68:
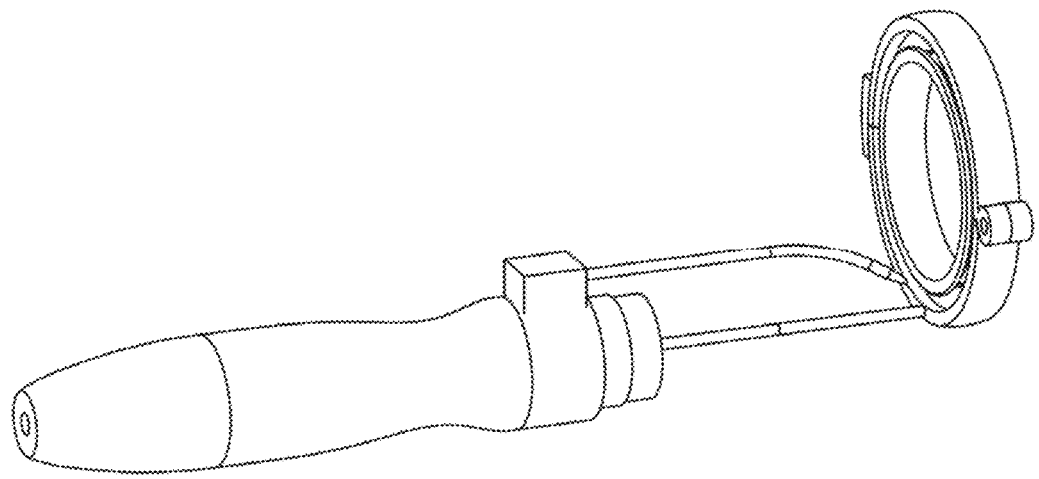
FIG. 68 is a perspective view of the ultrasonic vibrating system, wherein the ultrasonic vibrating system uses a rigid or integrated connection and is perpendicular between the ultrasonic vibrating rod and the outer annular knife.
Figure 69:
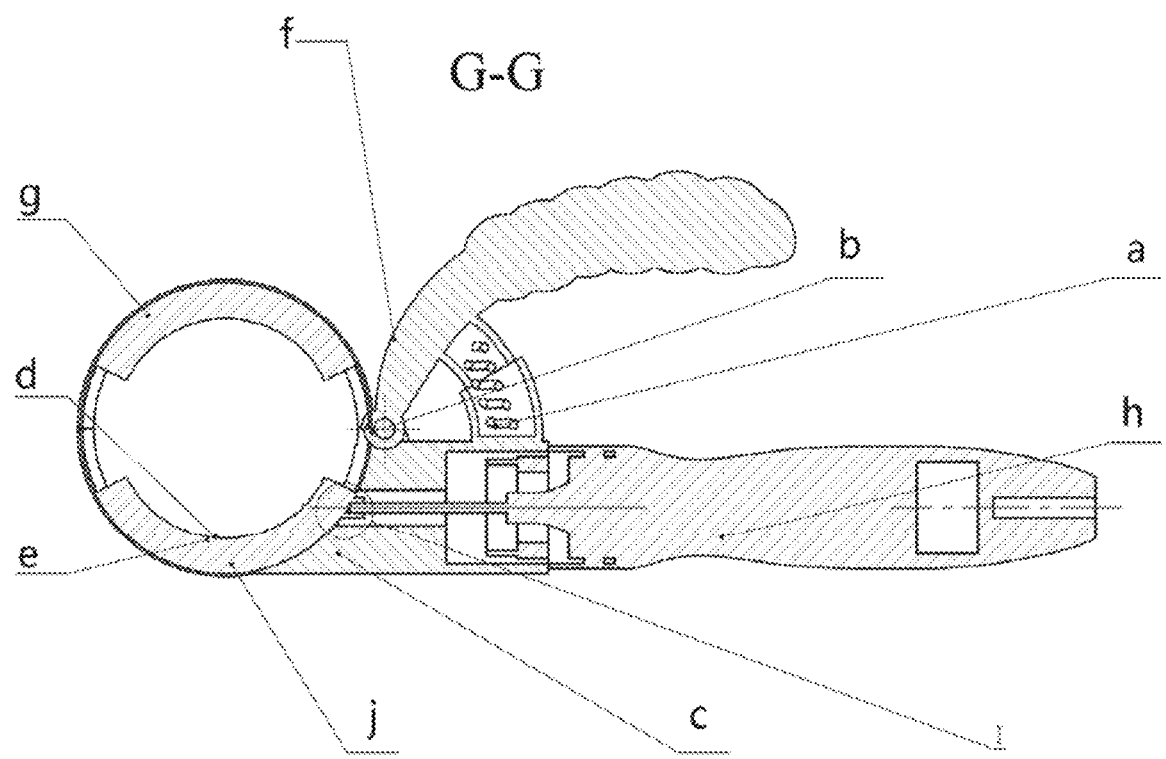
FIG. 69 is a sectional view of a pliers-type ultrasonic single-oscillation annular knife (the outer ring uses a semi-annular knife).
Figure 70:
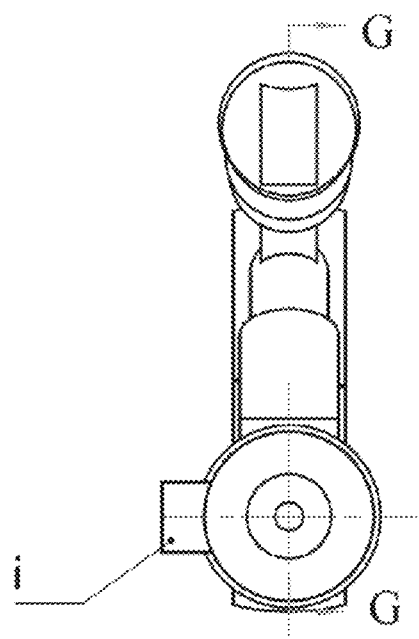
FIG. 70 is a bottom view of a pliers-type ultrasonic single-oscillation annular knife (the outer ring uses a semi-annular knife).
Figure 71:
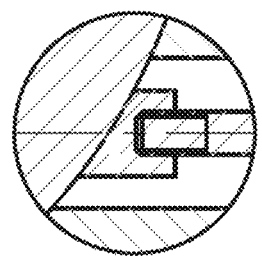
FIG. 71 is a partial enlarged view of part I of a pliers-type ultrasonic single-oscillation annular knife (the outer ring uses a semi-annular knife) shown in FIG. 69.
Figure 72:
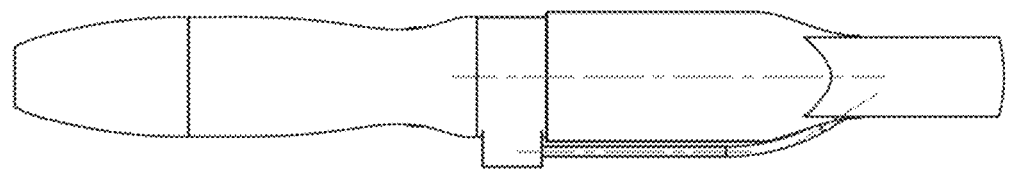
FIG. 72 is a first side view of a pliers-type ultrasonic single-oscillation annular knife (the outer ring uses a semi-annular knife).
Figure 73:
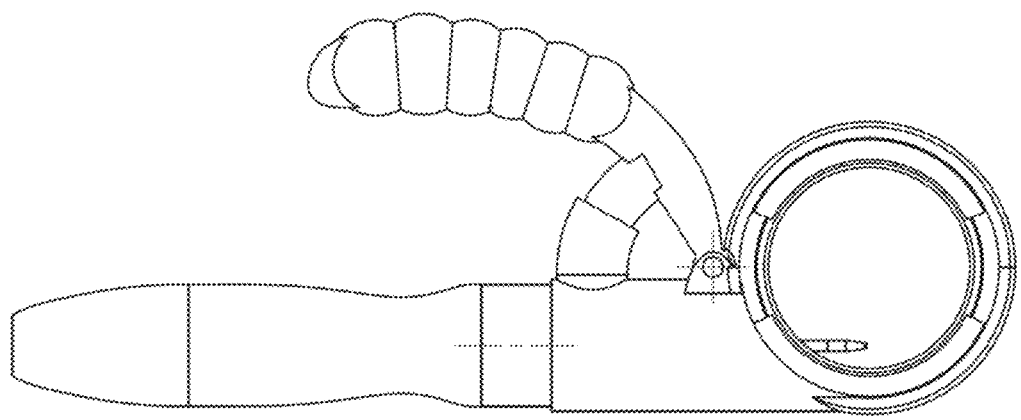
FIG. 73 is a top view of a pliers-type ultrasonic single-oscillation annular knife (the outer ring uses a semi-annular knife).
Figure 74:
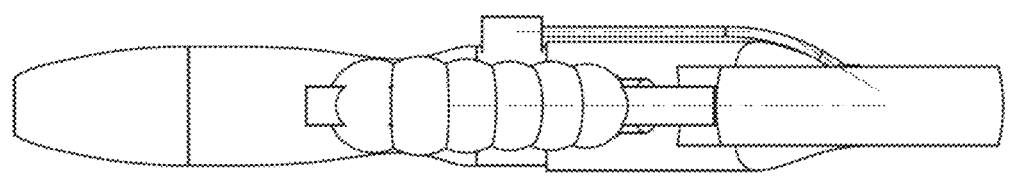
FIG. 74 is a second side view of a pliers-type ultrasonic single-oscillation annular knife (the outer ring uses a semi-annular knife).
Figure 75:
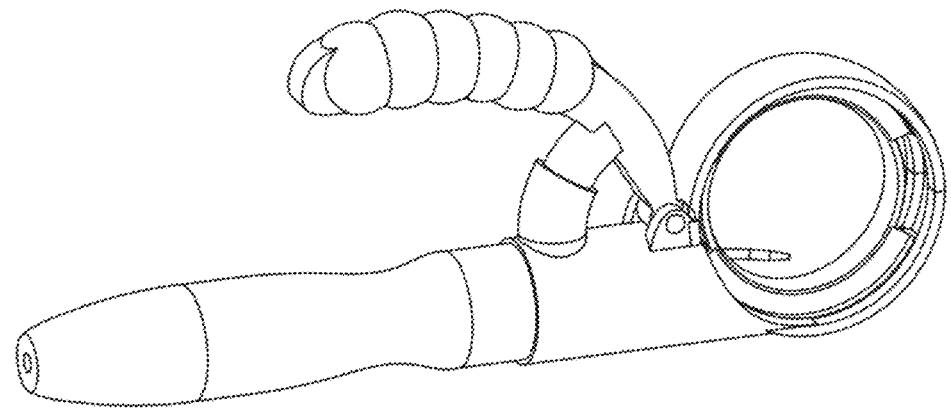
FIG. 75 is a perspective view of a pliers-type ultrasonic single-oscillation annular knife (the outer ring uses a semi-annular knife).
Figure 76:
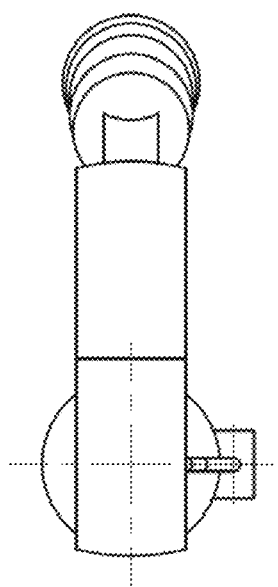
FIG. 76 is a view of a top portion of a pliers-type ultrasonic single-oscillation annular knife (the outer ring uses a semi-annular knife).
Figure 77:
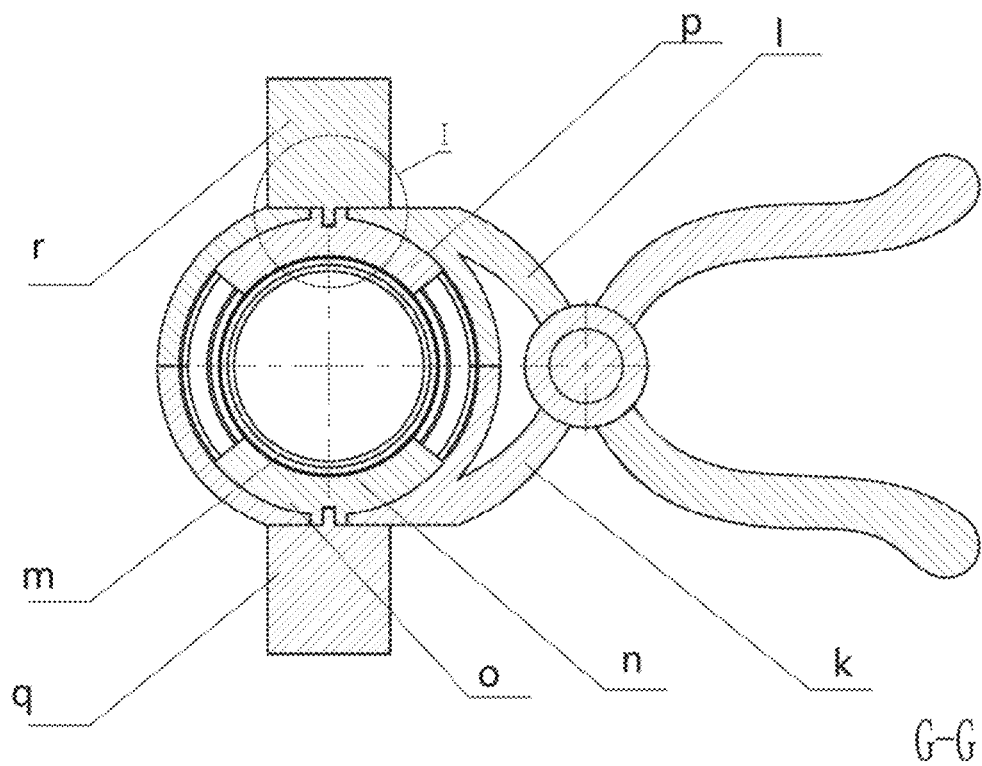
FIG. 77 is a sectional view of a pliers-type ultrasonic dual-oscillation annular knife.
Figure 78:
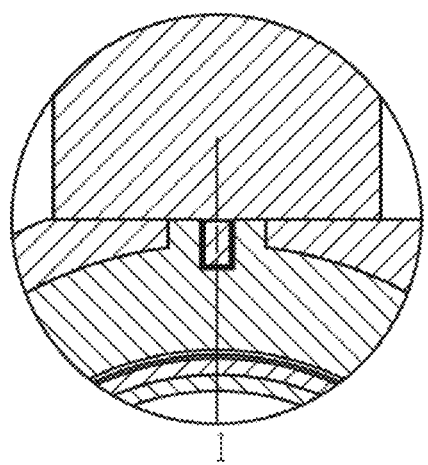
FIG. 78 is a partial enlarged view of part I of a pliers-type ultrasonic dual-oscillation annular knife (the outer ring uses a semi-annular knife) shown in FIG. 77.
Figure 79:
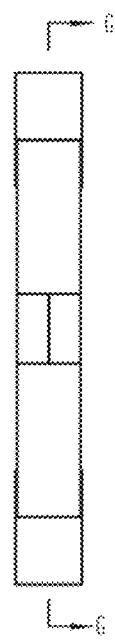
FIG. 79 is a view of top portion of a pliers-type ultrasonic dual-oscillation annular knife (the outer ring uses a semi-annular knife).
Figure 80:
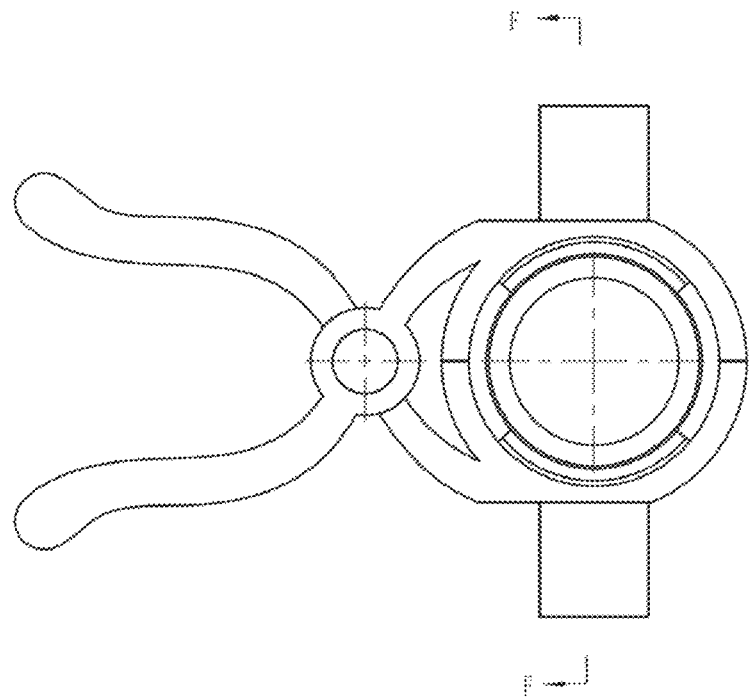
FIG. 80 is a top view of a pliers-type ultrasonic dual-oscillation annular knife (the outer ring uses a semi-annular knife).
Figure 81:
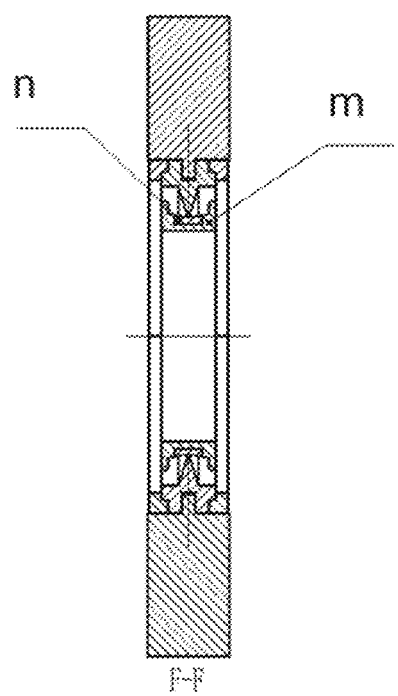
FIG. 81 is an F-F sectional view of a pliers-type ultrasonic dual-oscillation annular knife (the outer ring uses a semi-annular knife) shown in FIG. 80.
Figure 82:
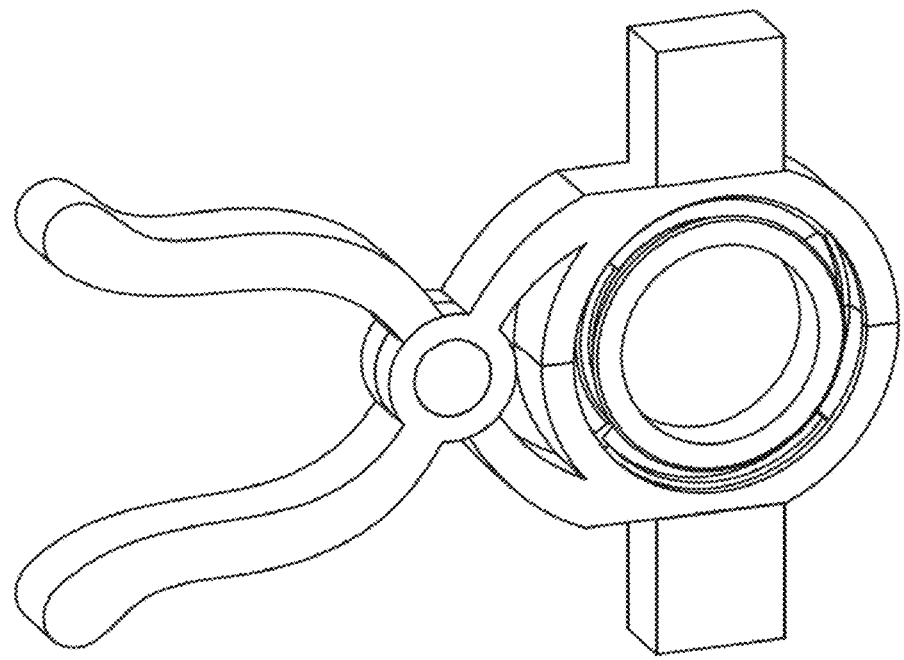
FIG. 82 is a perspective view of a pliers-type ultrasonic dual-oscillation annular knife (the outer ring uses a semi-annular knife).
Figure 83:
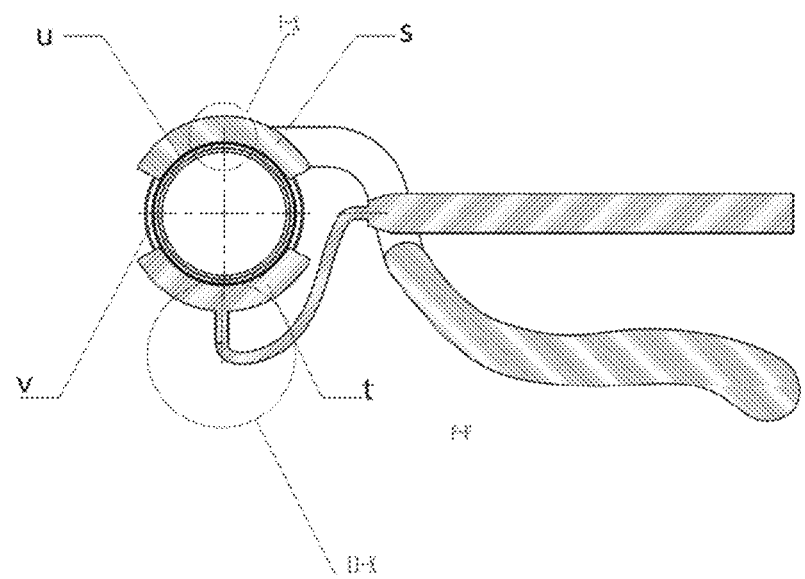
FIG. 83 is a sectional view of a direct-vibration scissor annular knife (semi-annular knife, quarter-annular knife) system.
Figure 84:
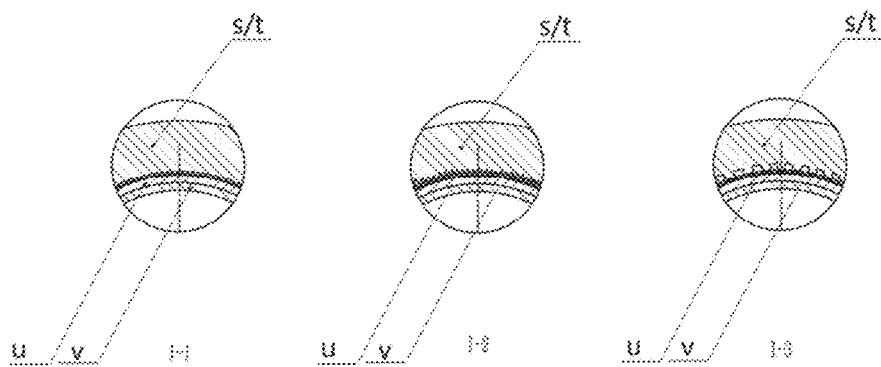
FIGS. 84A-84C are alternative schematic diagrams of I-X part of the direct-vibration scissor annular knife (semi-annular knife, quarter-annular knife) system shown in FIG. 87 (A-flat blade, B-triangle sawtooth blade, C-square sawtooth blade).
Figure 85:
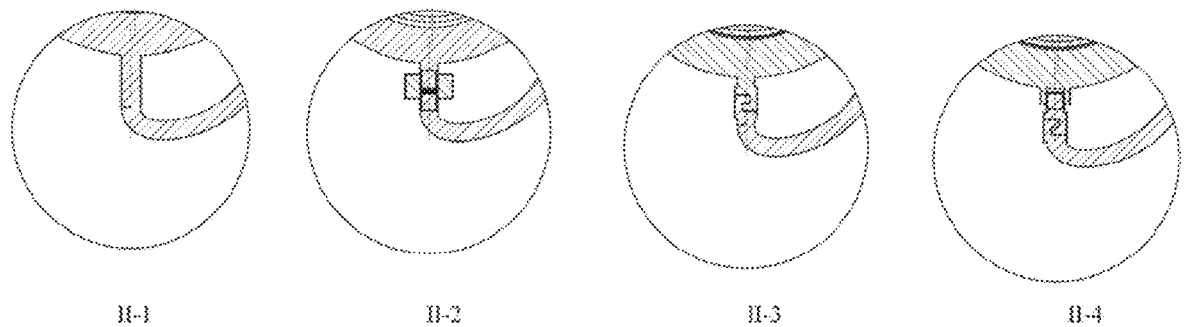
FIGS. 85A-85D are alternative schematic diagrams of II-X part of the direct-vibration scissor annular knife (semi-annular knife, quarter-annular knife) system shown in FIG. 87 (A-Rigid connecting rod, outer annular knife, B-thread fixed connecting rod, outer annular knife, C-buckle fixed connecting rod, outer annular knife, D-thread compound fixed connecting rod, outer annular knife)
Figure 86:
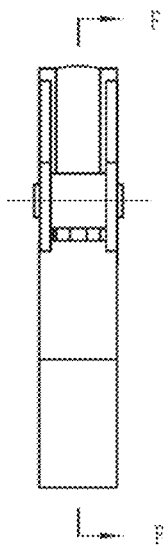
FIG. 86 is a view of top portion of a direct-vibration scissor annular knife (semi-annular knife, quarter-annular knife) system.
Figure 87:
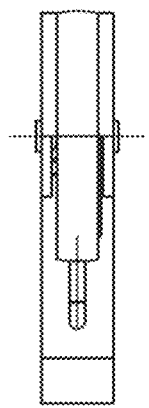
FIG. 87 is a view of bottom portion of a direct-vibration scissor annular knife (semi-annular knife, quarter-annular knife) system.
Figure 88:
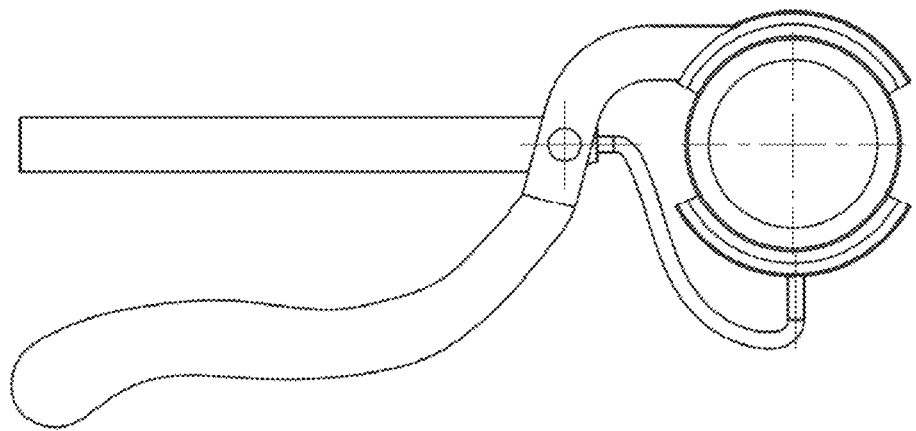
FIG. 88 is a top view of a direct-vibration scissor annular knife (semi-annular knife, quarter-annular knife) system.
Figure 89:
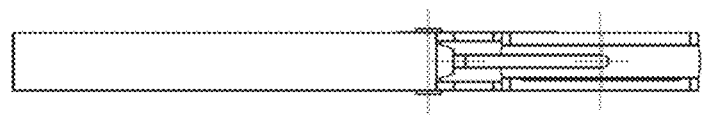
FIG. 89 is a first side view of a direct-vibration scissor annular knife (semi-annular knife, quarter-annular knife) system.
Figure 90:
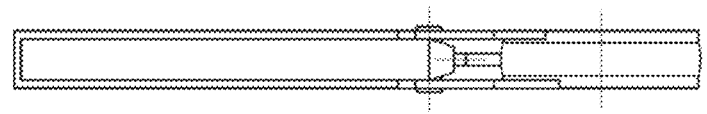
FIG. 90 is a second side view of a direct-vibration scissor annular knife (semi-annular knife, quarter-annular knife) system.
Figure 91:
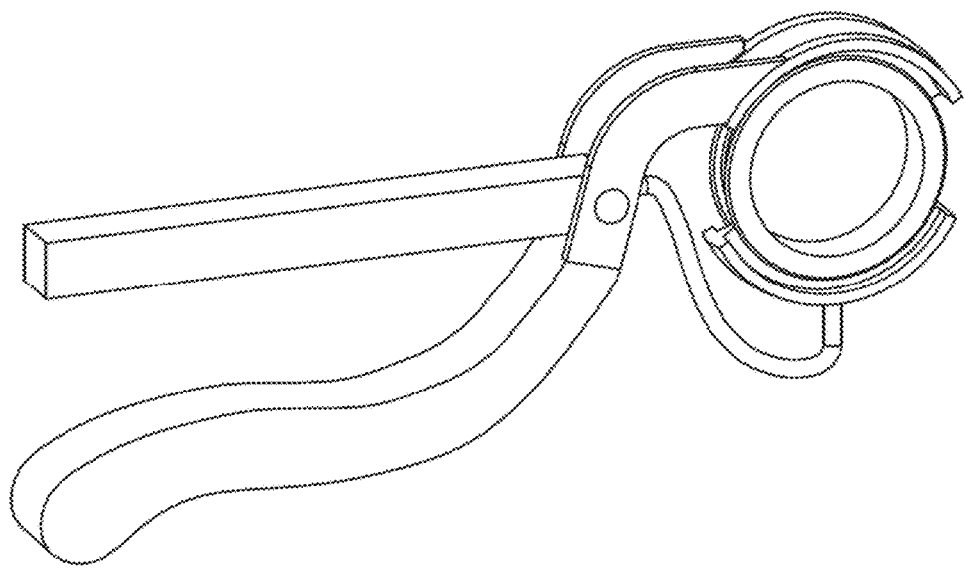
FIG. 91 is a first perspective view of a direct-vibration scissor annular knife (semi-annular knife, quarter-annular knife) system.
Figure 92:
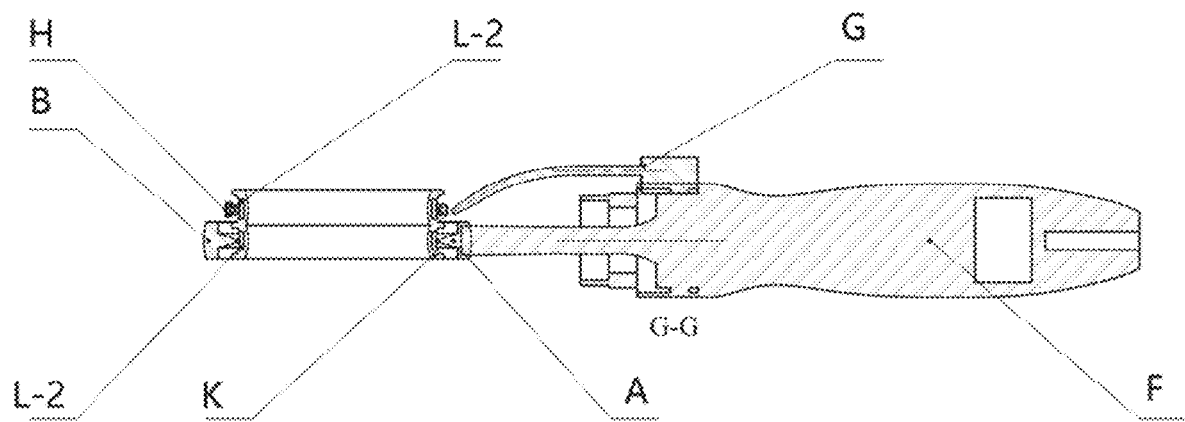
FIG. 92 is a sectional view of the side view of the double inner ring/inner ring with double-grooves ultrasonic vibration system.
Figure 93:
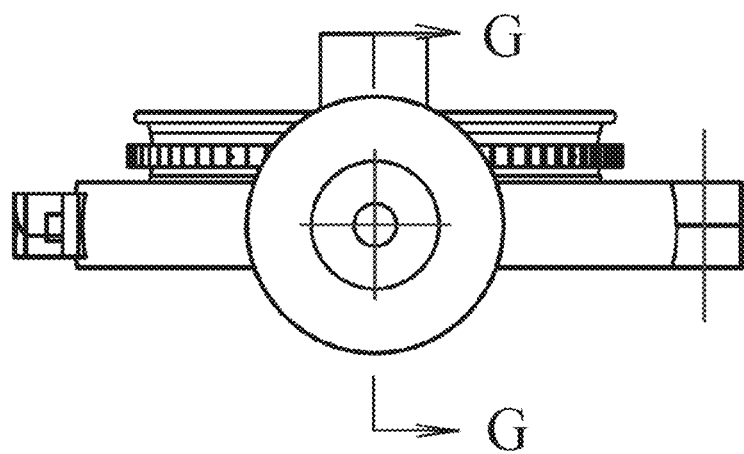
FIG. 93 is a view of the top portion of the double inner ring/inner ring with double-grooves ultrasonic vibration system.
Figure 94:
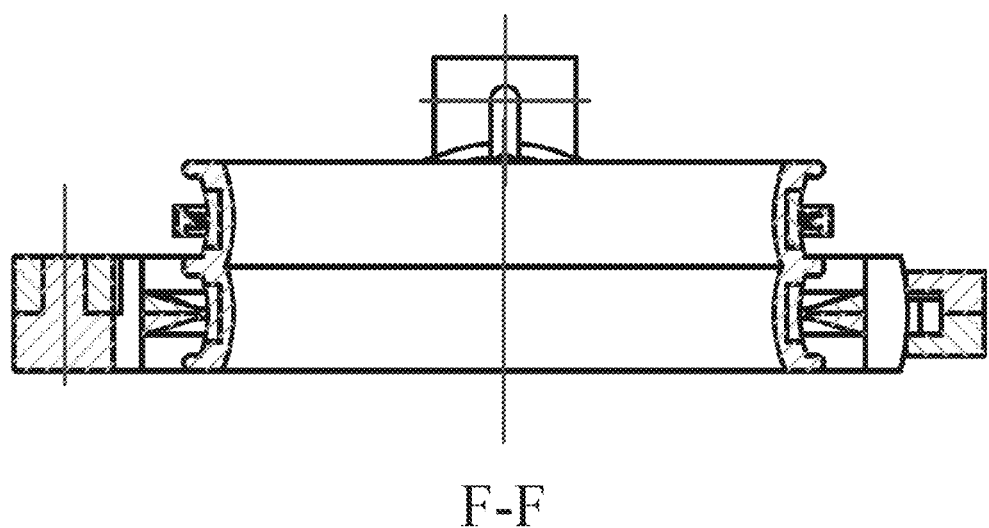
FIG. 94 is a bottom view of the double inner ring/inner ring with double-grooves ultrasonic vibration system.
Figure 95:
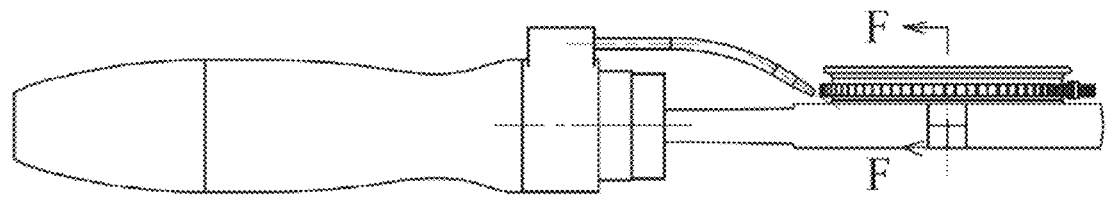
FIG. 95 is a side view of the double inner ring/inner ring with double-grooves ultrasonic vibration system.
Figure 96:
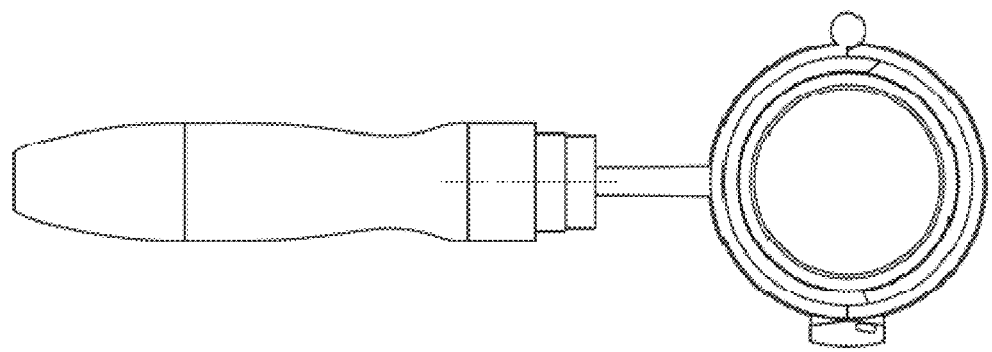
FIG. 96 is a top view of the double inner ring/inner ring with double-grooves ultrasonic vibration system.
Figure 97:
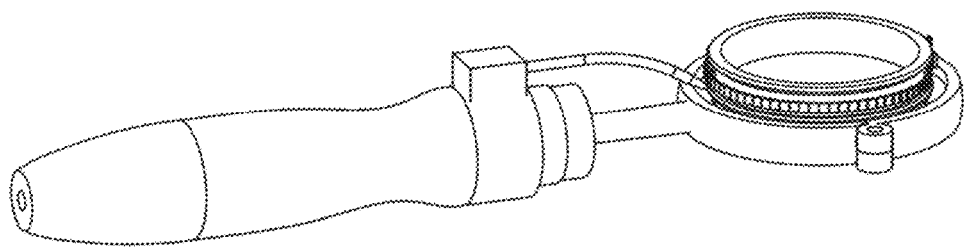
FIG. 97 is a perspective view of the double inner ring/inner ring with double-grooves ultrasonic vibration system.
Figure 98:
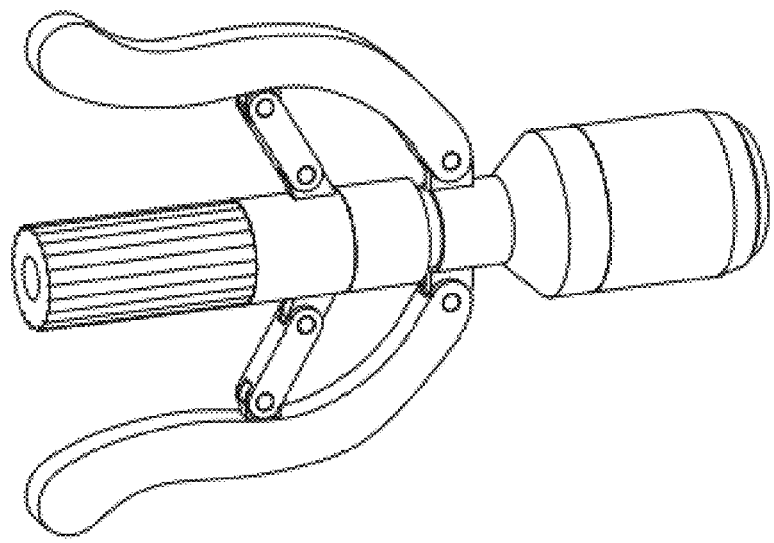
FIG. 98 is a front view of a circumcision device of the introverted ultrasound subassembly for compressing, cutting, hemostasis and healing of foreskin of the present invention.
Figure 99:
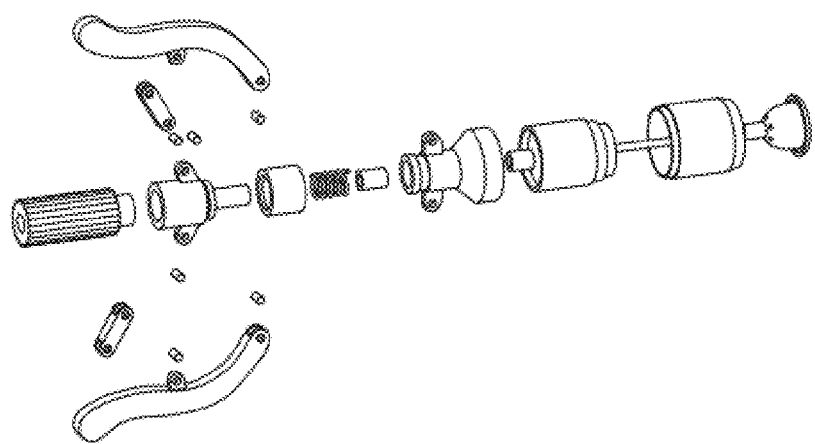
FIG. 99 is an explosive view of the circumcision device of the introverted ultrasound subassembly for compressing, cutting, hemostasis and healing of foreskin of the present invention.
Figure 100:
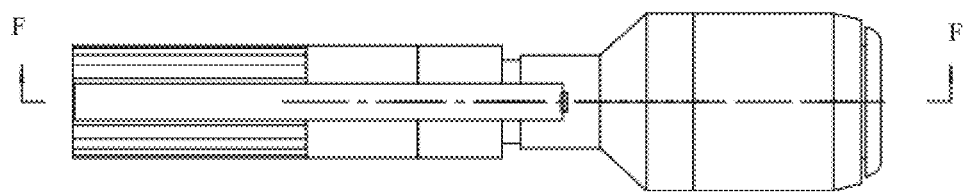
FIG. 100 is a top view of the circumcision device of the introverted ultrasound subassembly for compressing, cutting, hemostasis and healing of foreskin of the present invention.

Referring to FIG. 15 and FIG. 16, the positioning cylinder in the present embodiment can be fixed together with the body frame by matching structure of an upper housing 27, lower housing 28, and a locking ring 29. The nosing of distal end of the upper housing is to support the distal end of the positioning cylinder. The outside of the proximal end of the upper housing is provided with the external thread, the outside of distal end of the lower housing is also provided with the external thread, the inside of the locking ring is provided with internal thread, the upper housing, lower housing, a locking ring are fixedly connected by the threads.

The ultrasonic generating device in the present invention includes an ultrasonic generator 1 and a transducer 2. The generated ultrasonic waves are transmitted to the circumcision device by a main body 3 of the transmission device and a forepart 4 of the transmission device. The forepart of the transmission device can be connected to the positioning cylinder 19 of the circumcision device and/or the cutting device 24 through the fixedly-connected device 5, so that the ultrasonic waves are transmitted to the first annular contact surface 21 and/or the second annular contact surface 25. The fixedly-connected device 5 can perform connection through internal and external thread or the buckle device.

In order to prevent adhesions between the foreskin and the circumcision device during surgery to cause re-tearing of the wound, the portion of the positioning cylinder and the cutting device wherein in contact with the foreskin is provided with the anti-adhesion coating 16 (not shown in the figures). Preferably, the anti-adhesion coating 16 is provided on the first annular contact surface of the positioning cylinder and the second annular contact surface of the cutting device.

In order to avoid generating smoke and smell when the circumcision is performed by using ultrasonic, and affecting the visual field and the surgical environment, the circumcision device of the present invention is further provided with a water mist generator. Referring to FIG. 13, the water mist generator can include the annular water storage device 6 provided on the body frame, and located in the outer peripheral or the inner periphery of the cutting device. A water outlet 7 (not shown in the figures) which is disposed on a side of the annular water storage device facing the first annular contact surface 21. Water, alcohol, disinfectant and other liquids can be stored in the annular water storage device 6, and be sprayed by squeezing, pushing or ultrasonic vibration from the water outlet 7. Therefore, forming a water mist environment around the first annular contact surface 21 before the circumcision, during the circumcision and/or after the circumcision.

In the preferably embodiment, an ultrasonic circumcision assembly includes an ultrasonic generating device, a transmission device, and a circumcision device. The ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device is a closed circular ring and is used for performing circumcision to the foreskin. The circumcision device and the transmission device is integrally fixed connection as a whole or detachably connection, and/or the transmission is a detachable structure. The circumcision device is a close-ring structure whose aperture can be shrunk, which can receive the ultrasonic waves transmitted form the transmission device and perform ultrasonic cutting and/or clotting. The circumcision device includes the first ring and the second ring. The first ring and the second ring are arranged at intervals along the extension direction of the foreskin or relative to the inside and outside of the foreskin. The first ring is connected to the transmission device, and/or, the second ring is connected to the first ring and/or the transmission, and is used to receive the ultrasonic waves transmitted form the transmission device and performs ultrasonic cutting and/or clotting. The first ring is an inner ring, which is disposed inside of the foreskin, the second ring is an outer ring, which is disposed outside the foreskin. The inner ring and the outer ring cooperate to each other to clamp the foreskin. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generator, the transmission device, and the circumcision device. And/or, the water mist generator is integrally arranged on the ultrasonic generating device, the transmission device or the circumcision device. The water mist generator includes an atomizing chamber. Wherein the ultrasonic generating device is connected to the atomizing chamber and is used to provide ultrasonic waves to the atomizing chamber to atomize the stored water, and/or, ultrasonic circumcision assembly further includes a second ultrasonic generating device. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture and is configured to fasten the foreskin at a position adjacent to a front part of the glans. And/or, the protection device can be a baffle built in the foreskin and in the front part of the glans. And/or, the protection device can be an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure, preferably is a rubber ring connection provided in the inner loop of the inner ring.

An ultrasonic surgical device includes an ultrasonic generating device, a transmission device, an end structure, and a water mist generator. Wherein the ultrasonic generating device is used to generate ultrasonic waves and is connected to the transmission device to transmit ultrasonic waves to the transmission device. The transmission device is further connected to the end structure to transmit the ultrasonic waves to the end structure. The water mist generator is used to spry water mist on the end structure and/or the position where the end structure works before the end structure takes action, during the end structure is taking action, and/or after the end structure has taken action. The end structure is a circumcision device. The water mist generator is separately arranged with respect to the ultrasonic generating device, the transmission device, and the circumcision device. The water mist generator is integrally arranged on the ultrasonic generating device, the transmission device or the circumcision device. The water mist generator is an ultrasonic water mist generator. The water mist generator includes atomizing chamber. The ultrasonic generating device is connected to the atomizing chamber and is used to provide ultrasonic waves to the atomizing chamber to atomize the stored water. The ultrasonic surgical device further includes a second ultrasonic generating device. The second ultrasonic generating device is connected to the atomizing chamber and is used to provide ultrasonic waves to the atomizing chamber to atomize the stored water. The circumcision device is a closed circular ring and is used for performing circumcision to the foreskin. The circumcision device and the transmission device is fixed connection or detachable connection, and/or the transmission device is a detachable structure. The circumcision device is a close-ring structure with reducible aperture, which can receive the ultrasonic waves transmitted form the transmission device and perform ultrasonic cutting and/or clotting. Or, the circumcision device includes the first ring and the second ring, wherein the first ring and the second ring are arranged at intervals along the extension direction of the foreskin or relative to the inside and outside of the foreskin.

A circumcision assembly includes a circumcision device and a water mist generator, the water mist generator for spraying water mist to the circumcision device and/or the circumcision area before the circumcision, during the circumcision and/or after the circumcision. The water mist generator is partial or integrally mounted on the circumcision device. The water mist generator includes a water tank and a nozzle. The nozzle is rightly faced to the position where the circumcision device clamps the foreskin. Further, the circumcision assembly includes an ultrasonic generating device and transmission device. The ultrasonic generating device is used to generate ultrasonic waves and is connected to the transmission device to transmit ultrasonic waves to the transmission device. The transmission device is further connected to the circumcision device and transmits the ultrasonic waves to the circumcision device. The water mist generator is partial or integrally provided on the ultrasonic generating device or the transmission device. The water mist generator is an ultrasonic water mist generator, and the water tank is an atomizing chamber. The ultrasonic generating device is connected to the atomizing chamber and is used to provide ultrasonic waves to the atomization chamber to atomize the stored water. The circumcision assembly further includes a second ultrasonic generating device. The second ultrasonic generating device is connected to the atomizing chamber and is used to provide ultrasonic waves to the atomizing chamber to atomize the stored water. The circumcision device is a closed circular ring and is used for performing circumcision to the foreskin. Or, the circumcision device is a close-ring structure with reducible aperture, which can receive the ultrasonic waves transmitted form the transmission device and perform ultrasonic cutting and/or clotting. Or, the circumcision device includes the first ring and the second ring, wherein the first ring and the second ring are arranged at intervals along the extension direction of the foreskin or relative to the inside and outside of the foreskin. The circumcision device and the transmission device is fixed connected or detachably connected, and/or the transmission device is a detachable structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is integrated connected with the transmission device, and the annular plane of the inner ring is not the same plane as the extension direction of the transmission device. The angle between the annular plane of the inner ring and the extension direction of the transmission device is 45°-135°. The annular plane of the inner ring is perpendicular to the extension direction of the transmission device. The connecting point of the inner ring and the transmission device is located on the upper and/or the lower side wall of the inner ring. The inner ring is a closed circular ring or a split ring formed by a circular smooth inner loop in a closed state. The outer ring is provided with an opening, and the opening can be closed by a locking device. The foreskin tissue which contacts with the circumcision device is coated with Teflon™ material. The inner ring is built in the inside of the foreskin. The outer ring is disposed on the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generating device, the transmission device, and the circumcision device; or, the water mist generator is integrally arranged on the ultrasonic generator, the transmission device, or the circumcision device. Preferably, the water mist generator includes an atomizing chamber. The ultrasonic generating device is connected to the atomizing chamber and is used to provide ultrasonic waves to the water-atomizing chamber to atomize the stored water, and/or, the ultrasonic circumcision assembly further includes a second ultrasonic generating device. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is annular structure with a reducible aperture and is configured to fasten the foreskin adjacent to the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. Preferably, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is integrated connection with the transmission device, and the annular plane of the inner ring is at the same plane as the extension direction of the transmission device. The connecting point where the inner ring and the transmission device integrated connected is located on the wall of the outer edge of the inner ring. The inner ring is built in the inside of the foreskin. The outer ring is used in the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The inner ring is a closed circular ring or a split ring formed by a circular smooth inner ring in a closed state. The outer ring is provided with an opening, and the opening can be closed by a locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device; or/and, the water mist generator is integrally arranged on the ultrasonic generating device, the transmission device, or the circumcision device. The water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin adjacent to the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. The protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, the second part is connected to the circumcision device. The first part and the second part use fixedly-connected device to achieve a detachable connection. The circumcision device includes the inner ring and the outer ring, and the inner ring and the outer ring are incorporated with each other. The second part of the transmission device is integrally connected to the inner ring. The annular plane of the inner ring is not at the same plane as the extension direction of the transmission device. The annular plane of the inner ring is perpendicular to the extension direction of the transmission device. The fixedly-connected device is internal and external threads, concave and convex structures, or buckle structures, which are provided in the first part and the second part and matches to each other. The fixedly-connected device is provided in the position where is close to the circumcision device along the extension direction of the transmission. And/or, the connecting point where the inner ring and the transmission device integrated connected is located on the wall of the outer edge of the inner ring. The inner ring is a closed circular ring or a split ring formed by a circular smooth inner ring in a closed state. The outer ring is provided with an opening, the opening can be closed by the locking device. And/or, the foreskin tissue which contacts with the circumcision device is coated with Teflon™ material. The inner ring is built in the inside of the foreskin. The outer ring is disposed on the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generating device, the transmission device, and the circumcision device. Or, the water mist generator is integrally arranged on the ultrasonic generating device, the transmission device, or the circumcision device. Preferably, the water mist generator includes a atomizing chamber. The ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. Preferably, the protection device is an annular structure with a reducible aperture, and is configured to fasten the foreskin adjacent to the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. Preferably, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, and the second part is connected to the circumcision device. The first part and the second part use the first fixedly-connected device to achieve a detachable connection. The circumcision device includes the inner ring and the outer ring, and the inner ring and the outer ring are matched with each other. The second part of the transmission device and the inner ring are use the second fixedly-connected device to achieve a detachable connection. The annular plane of the inner ring is not at the same plane as the extension direction of the transmission device. The annular plane of the inner ring is perpendicular to the extension direction of the transmission device. The first fixedly-connected device is internal and external threads, concave and convex structures, or buckle structures, which are provided in the first part and the first end of the second part and matches to each other. And/or, the second fixedly-connected device is internal and external threads, concave and convex structures, or buckle structures, which are provided in the inner ring and the second end of the second part and matches to each other. The first fixedly-connected device is provided in the position where is close to the circumcision device along the extension direction of the transmission. And/or, the connecting point where the inner ring and the transmission device connected is located on the wall of the outer edge of the inner ring. The inner ring is a closed circular ring or a split ring formed a circular smooth inner ring in a closed state. The outer ring is provided with an opening, the opening can be closed by the locking device. And/or, the foreskin tissue which contacts with the circumcision device is coated with Teflon™ material. The inner ring is built in the inside of the foreskin. The outer ring is used in the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generating device, the transmission device, and the circumcision device. Or, the water mist generator is integrally arranged on the ultrasonic generating device, the transmission device, or the circumcision device. Preferably, the water mist generator includes an atomizing chamber. The ultrasonic generating device is connected to the atomizing chamber and is used to provide ultrasonic waves to the atomizing chamber to atomize the stored water, and/or, the ultrasonic circumcision assembly further includes a second ultrasonic generating device. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. Preferably, the protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. Preferably, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring, and the inner ring and the outer ring are matched with each other. The transmission device and the inner ring use the fixedly-connected device to achieve a detachable connection. The annular plane of the inner ring is at the same plane as the extension direction of the transmission device. The annular plane of the inner ring is not at the same plane as the extension direction of the transmission device. The annular plane of the inner ring is perpendicular to the extension direction of the transmission device. The fixedly-connected device is internal and external threads, concave and convex structures, or buckle structures, which are provided in the inner ring and the transmission device and match to each other. The fixedly-connected device is located at the end of the transmission device, wherein the end of the transmission device is connected to the inner ring, and/or, the side wall and/or the wall of the inner ring, wherein the side wall and/or the wall of the inner ring is connected to transmission device. The inner ring is a closed circular ring or a split ring formed a circular smooth inner ring in a closed state. A closing device of the inner ring with an opening can work as a fixedly-connected device with the transmission device to achieve a detachable connection. The outer ring is provided with an opening, the opening can be closed by the locking device. And/or, the foreskin tissue which contacts with the circumcision device is coated with Teflon™ material. The inner ring is built in the inside of the foreskin. The outer ring is disposed on the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generating device, the transmission device, and the circumcision device. Or, the water mist generator is integrally arranged on the ultrasonic generating device, the transmission device, or the circumcision device. Preferably, the water mist generator includes a atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. Preferably, the protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. Preferably, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein, the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The outer ring is integrally connected to the transmission device, and the plane where the annular of the outer ring and the plane along the extension direction of the transmission device are not in the same plane. The plane where the annular of the outer ring is located is at an angle of 45 degrees to 135 degrees to the extension direction of the transmission device. The plane where the annular of the outer ring and the plane along the extension direction of the transmission device are perpendicular to each other. The connecting point where the outer ring and the transmission device integrally connected is located on the wall of the outer edge of the outer ring, or, upper side wall, or, lower side wall. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The inner ring is built in the inside of the foreskin. The outer ring is disposed on the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generating device, the transmission device, and the circumcision device. And/or, the water mist generator is integrally arranged on the ultrasonic generating device, the transmission device, or the circumcision device. Preferably, the water mist generator includes a atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. Preferably, the protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein, the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The outer ring is integrally connected to the transmission device, and the annular plane of the outer ring and the plane along the extension direction of the transmission device are in the same plane. The connecting point where the outer ring and the transmission device integrally connected is located on the wall of the outer edge of the outer ring. The inner ring is built in the inside of the foreskin. The outer ring is disposed on the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device. And/or, the water mist generator is integrally arranged on the ultrasonic generating device, the transmission device, or the circumcision device. The water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin adjacent to the front part of the glans. And/or, the protection device is a baffle arranged inside the foreskin and in the front part of the glans. And/or, the protection device is an ultrasonic insulation structure and/or a vibration-damping energy-dissipation structure arranged at the inner edge of the inner ring. The protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, the second part is connected to the circumcision device. The first part and the second part use the first fixedly-connected device to achieve a detachable connection. The circumcision device includes the inner ring and the outer ring, and the inner ring and the outer ring are matched with each other. The second part of the transmission device and the outer ring are integrally connected, and further, the annular plane of the outer ring is at the same plane as the extension direction of the transmission device. The connecting point where the outer ring and the transmission device are integrally connected is located on the wall of the outer edge of the outer ring. The inner ring is built in the inside of the foreskin. The outer ring is used in the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The first fixedly-connected device is internal and external threads, concave and convex structures, or buckle structures, which are provided in the first part and the first end of the second part and matches to each other. The fixedly-connected device is provided in the position where is closer to the circumcision device along the extension direction of the transmission. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device. And/or, the water mist generator is integrally arranged on the ultrasonic generating device, the transmission device, or the circumcision device. And/or, the water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. Preferably, the protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, the second part is connected to the circumcision device. The first part and the second part use the first fixedly-connected device to achieve a detachable connection. The circumcision device includes the inner ring and the outer ring, and the inner ring and the outer ring are matched with each other. The second part of the transmission device and the outer ring use the second fixedly-connected device to achieve a detachable connection, and further, the annular plane of the outer ring is at the same plane as the extension direction of the transmission device. The first fixedly-connected device is internal and external threads, concave and convex structures, or buckle structures, which are provided in the first part and the first end of the second part and matches to each other. And/or, the second fixedly-connected device is internal and external threads, concave and convex structures, or buckle structures, which are provided in the outer ring and the second end of the second part and matches to each other. The first fixedly-connected device is provided in the position where is closer to the circumcision device along the extension direction of the transmission device. The connecting point where the outer ring and the transmission device are connected is located on the wall of the outer edge of the outer ring. The inner ring is built in the inside of the foreskin. The outer ring is used in the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device. And/or, the water mist generator is integrally arranged on the ultrasonic generating device, the transmission device, or the circumcision device. And/or, the water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes the inner ring and the outer ring, and the inner ring and the outer ring are matched with each other. The transmission device and the outer ring use the fixedly-connected device to achieve a detachable connection, and further, the annular plane of the outer ring is at the same plane as the extension direction of the transmission device. The fixedly-connected device is internal and external threads, concave and convex structures, or buckle structures, which are provided in the outer ring and the transmission device and matches to each other. The fixedly-connected device is located at the end of the outer ring connecting to the transmission device, and/or the side wall and/or the wall in the outer edge of outer ring connecting to the transmission device. The outer ring is provided with an opening, and the locking device of the opening can work as a fixedly-connected device of the outer ring and the transmission device to achieve a detachable connection. The inner ring is built in the inside of the foreskin. The outer ring is used in the outside of the foreskin, and the inner ring and the outer ring are matched with each other to clamp the foreskin. Or, the inner ring is sleeved on the outside of the foreskin of the penis and is placed inside the inverted foreskin when the foreskin is inverted. The outer ring is arranged outside the inverted foreskin. The inner ring and the outer ring are matched with each other to clamp the foreskin. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device. And/or, the water mist generator is integrally arranged on the ultrasonic generating device, the transmission device, or the circumcision device. The water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, the second part is connected to the circumcision device. The first part and the second part use the first fixedly-connected device to achieve a detachable connection. The circumcision device includes the inner ring and the outer ring, and the inner ring and the outer ring are matched with each other. The second part of the transmission device and the outer ring are integrally connected to each other, and further, the annular plane of the outer ring is not at the same plane as the extension direction of the transmission device. The annular plane where the outer ring is located is at an angle of 45 degrees to 135 degrees to the extension direction of the transmission device. The annular plane of the outer ring is perpendicular to the plane as the extension direction of the transmission device. The connecting point where the outer ring and the transmission device are connected is located on the wall of the outer edge of the outer ring, or, upper side wall, or, lower side wall. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The fixedly-connected device is internal and external threads, concave and convex structures, or buckle structures, which are provided in the first part and the second part and matches to each other. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device, and the circumcision device. And/or, the water mist generator is integrally arranged on the ultrasonic generating device, the transmission device, or the circumcision device. And/or, the water mist generator includes an atomizing chamber. Wherein, the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. Wherein the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The transmission device includes a first part and a second part, wherein the first part is connected to the ultrasonic generating device, the second part is connected to the circumcision device. The first part and the second part use the first fixedly-connected device to achieve a detachable connection. The circumcision device includes the inner ring and the outer ring, and the inner ring and the outer ring are matched with each other. The second part of the transmission device and the outer ring use the second fixedly-connected device to achieve a detachable connection, and further, the annular plane of the outer ring is not at the same plane as the extension direction of the transmission device. The first fixedly-connected device is internal and external threads, concave and convex structures, or buckle structures, which are provided in the first part and the first end of the second part and matches to each other. And/or, the second fixedly-connected device is internal and external threads, concave and convex structures, or buckle structures, which are provided in the outer ring and the second end of the second part and matches to each other. The annular plane where the outer ring is located is at an angle of 45 degrees to 135 degrees to the extension direction of the transmission device. The annular where the outer ring is located and the plane along the extension direction of the transmission device are perpendicular to each other. The connecting point where the outer ring and the transmission device are connected is located on the wall of the outer edge of the outer ring, or, upper side wall, or, lower side wall. The inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generator, the transmission device, and the circumcision device. And/or, the water mist generator is integrally arranged on the ultrasonic generator, the transmission device, or the circumcision device. And/or, the water mist generator includes an atomizing chamber. Wherein, the ultrasonic generator is connected to the atomizing chamber and is used to provide ultrasonic waves to the atomizing chamber to atomize the stored water, and/or, a second ultrasonic generator is further included in the ultrasonic circumcision assembly. The second ultrasonic generator is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision.

An ultrasonic circumcision assembly includes an ultrasonic generator, a transmission device, and a circumcision device. Wherein, the ultrasonic generator is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The transmission device and the outer ring use the fixedly-connected device to achieve a detachable connection, and further, the annular plane of the outer ring is not at the same plane as the extension direction of the transmission device. The plane where the annular of the outer ring is located is at an angle of 45 degrees to 135 degrees to the extension direction of the transmission device. The plane where the annular of the outer ring is perpendicular to the plane along the extension direction of the transmission device. The fixedly-connected device is located at the end of the outer ring connecting to the transmission device, and/or the side wall and/or the outer edge of outer ring connecting to the transmission device. The fixedly-connected device is internal and external threads, concave and convex structures, or buckle structures, which are provided in the outer ring and the transmission device and matches to each other. The outer ring is provided with an opening, the locking device of the opening works as a fixedly-connected device to achieve a detachable connection with the transmission device. And/or, the inner ring is a closed circular ring or a split ring forming a circular smooth inner ring in a closed state. The outer ring is provided with an opening, the opening can be closed by the locking device. And/or, the foreskin tissue which contacts with the circumcision device is coated with Teflon™ material. The ultrasonic circumcision assembly further includes a water mist generator for spraying water mist to the circumcision device and/or the circumcision area before the circumcision, during the circumcision and/or after the circumcision. Preferably, the water mist generator is separately arranged with respect to the ultrasonic generator, the transmission device, and the circumcision device. And/or, the water mist generator is integrally arranged on the ultrasonic generator, the transmission device, or the circumcision device. And/or, the water mist generator includes an atomizing chamber. Wherein, the ultrasonic generator is connected to the atomizing chamber and is used to provide ultrasonic waves to the atomizing chamber to atomize the stored water, and/or, a second ultrasonic generator is further included in the ultrasonic circumcision assembly. The second ultrasonic generator is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, a first fixedly-connected device, a second fixedly-connected device and a circumcision device. The ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is a closed circular ring, wherein the inner ring is detachably connected to the transmission device through the first fixedly-connected device, the outer ring is detachably connected to the transmission device through the second fixedly-connected device. The spaces between the first fixedly-connected device and the second fixedly-connected device is provided that after the inner ring and the outer ring are fixedly matched and fastened, the pressure of the circumferential line at the contact area of the outer edge of the inner ring and the inner edge of the outer ring is 0.1-3.5 N/mm. The first fixedly-connected device and the second fixedly-connected device are internal and external threads, concave and convex structures, or buckle structures, which are provided in the inner ring, the outer ring, and the transmission device and matches to each other, respectively. The transmission device includes a first part and a second part. The first part is connected to the ultrasonic generating device. The second part is connected to the circumcision device. The first part and the second part are detachably connected via a third fixedly-connected device. The annular plane where the inner ring and/or the outer ring is located is at an angle of 45 degrees to 135 degrees to the extension direction of the transmission device. The annular plane where the inner ring and/or the outer ring is located is perpendicular to the extension direction of the transmission device. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device and the circumcision device. And/or, the water mist generator may be integrally arranged on the ultrasonic generating device, the transmission device or the circumcision device. And/or, the water mist generator may include an atomizing chamber. Wherein the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, a first fixedly-connected device, a second fixedly-connected device and a circumcision device. Wherein, the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is an open-close circular ring consisting of two or more arc-shaped structures. The inner ring is detachably connected to the transmission device through the first fixedly-connected device. The outer ring is detachably connected to the transmission device through the first fixedly-connected device. The spaces between the first fixedly-connected device and the second fixedly-connected device is provided that after the inner ring and the outer ring are fixedly matched and fastened, the pressure of the circumferential line at the contact area of the outer edge of the inner ring and the inner edge of the outer ring is 0.1-3.5 N/mm. The first fixedly-connected device and the second fixedly-connected device are internal and external threads, concave and convex structures, or buckle structures, which are provided in the inner ring, the outer ring, and the transmission device and match to each other, respectively. The transmission device includes a first part and a second part. The first part is connected to the ultrasonic generating device. The second part is connected to the circumcision device. The first part and the second part are detachably connected via a third fixedly-connected device. The annular plane where the inner ring and/or the outer ring is located is at an angle of 45 degrees to 135 degrees to the extension direction of the transmission device. The annular plane where the inner ring and/or the outer ring is located is perpendicular to the extension direction of the transmission device. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device and the circumcision device. And/or, the water mist generator may be integrally arranged on the ultrasonic generating device, the transmission device or the circumcision device. And/or, the water mist generator may include a atomizing chamber. Wherein the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner edge of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, a fixedly-connected device and a circumcision device. Wherein, the ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is a closed circular ring. The inner ring is detachably connected to the transmission device through the fixedly-connected device. The outer ring is detachably connected to the transmission device through the fixedly-connected device. After the inner ring and the outer ring are fixedly matched and fastened, the pressure of the circumferential line at the contact area of the outer edge of the inner ring and the inner edge of the outer ring is 0.1-3.5 N/mm. The fixedly-connected device is internal and external threads, concave and convex structures, or buckle structures, which are provided in the transmission device and the structures that are matched with the inner ring, the outer ring. The transmission device includes a first part and a second part. The first part is connected to the ultrasonic generating device. The second part is connected to the circumcision device. The first part and the second part are detachably connected via a third fixedly-connected device. The annular plane where the inner ring and/or the outer ring is located is at an angle of 45 degrees to 135 degrees to the extension direction of the transmission device. The annular plane where the inner ring and/or the outer ring is located is perpendicular to the extension direction of the transmission device. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device and the circumcision device. And/or, the water mist generator can be integrally arranged on the ultrasonic generating device, the transmission device or the circumcision device. And/or, the water mist generator includes an atomizing chamber. Wherein the ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the atomizing chamber and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with a reducible aperture, and is configured to fasten the foreskin near the front part of the glans. And/or, the protection device is a baffle arranged inside the foreskin and in the front part of the glans. And/or, the protection device is an ultrasonic insulation structure and/or a vibration-damping energy-dissipation structure arranged at the inner periphery of the inner ring. And/or, the protection device and the circumcision device are connected or unconnected. Preferably, the protection device and the circumcision device are connected through the ultrasonic insulation structure and/or the vibration-damping energy-dissipation structure.

An ultrasonic circumcision assembly includes an ultrasonic generating device, a transmission device, a fixedly-connected device and a circumcision device. The ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The inner ring is a closeable circular ring consisting of two or more arc-shaped structures. The inner ring is detachably connected to the transmission device via the fixing device. The outer ring is detachably connected to the transmission device via the fixing device. After the inner ring and the outer ring are fixedly connected to the fixing device, respectively, and the inner ring and the outer ring are fastened, the pressure of the circumferential line at the contact part of the outer edge of the inner ring and the inner edge of the outer ring is 0.1-3.5 N/mm. The fixing device is an internal-external thread, or, a concave-convex structure or a snap-fit structure which is arranged on the transmission device and matches with the corresponding structures on the inner ring and the outer ring. The transmission device includes a first part and a second part. The first part is connected to the ultrasonic generating device. The second part is connected to the circumcision device. The first part and the second part are detachably connected via a third fixing device. The plane where the inner ring and/or the outer ring is located is at an angle of 45 degrees to 135 degrees to the extending direction of the transmission device. Preferably, the plane where the inner ring and/or the outer ring is located is perpendicular to the extending direction of the transmission device. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device and the circumcision device. And/or, the water mist generator may be integrally arranged on the ultrasonic generating device, the transmission device or the circumcision device. And/or, the water mist generator may include an atomizing chamber. The ultrasonic generating device is connected to the atomizing chamber and is used to provide ultrasonic waves to the atomizing chamber to atomize the stored water, and/or, a second ultrasonic generating device is further included in the ultrasonic circumcision assembly. The second ultrasonic generating device is connected to the water-atomization tank and is used to provide ultrasonic waves to the atomizing chamber to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with an reducible aperture and is configured to fasten the foreskin at a position near a front part of the glans. And/or, the protection device may be a baffle arranged inside the foreskin and in the front part of the glans. And/or, the protection device may be an ultrasonic insulation structure and/or a vibration-damping energy-dissipation structure arranged at the inner periphery of the inner ring. And/or, the protection device and the circumcision device are connected or not connected. Preferably, the protection device and the circumcision device are connected through the ultrasonic insulation structure and/or the vibration-damping energy-dissipation structure.

An ultrasonic circumcision assembly includes an ultrasonic generating device, a transmission device, and a circumcision device. The ultrasonic generating device is used to generate ultrasonic waves and is connected to the transmission device to transmit ultrasonic waves to the transmission device. The transmission device is further connected to the circumcision device to transmit the ultrasonic waves to the circumcision device. The circumcision device includes an inner ring and an outer ring. The inner ring matches with the outer ring. The transmission device is respectively connected to the inner ring and the outer ring. The transmission device includes a first transmission device and a second transmission device. The first transmission device is connected to the outer ring. The second transmission device is connected to the inner ring. The ultrasonic generating device includes a first ultrasonic generating device and a second ultrasonic generating device. The first ultrasonic generating device is connected to the first transmission device. The second ultrasonic generating device is connected to the second transmission device. The plane where the annulus of the outer ring is located is at an angle of 45 degrees to 135 degrees to the extending direction of the first transmission device, and/or, the plane where the annulus of the inner ring is located is at an angle of 45 degrees to 135 degrees to the extending direction of the transmission device. Preferably, the plane where the annulus of the outer ring is located is perpendicular to the extending direction of the first transmission device, and/or, the plane where the annulus of the inner ring is located is perpendicular to the extending direction of the transmission device. The first transmission device is detachably connected to the outer ring through a fixing device, and/or the second transmission device is detachably connected to the inner ring through a fixing device, and/or, the first transmission device includes a first part and a second part, wherein the first part is connected to the ultrasonic generating device, the second part is connected to the outer ring, and the first part and the second part are detachably connected through a fixing device, and/or, the second transmission device includes a first part and a second part, wherein the first part is connected to the ultrasonic generating device, the second part is connected to the inner ring, and the first part and the second part are detachably connected through a fixing device. The ultrasonic circumcision assembly further includes a water mist generator for spraying water mist to the circumcision device and/or the circumcision area before the circumcision, during the circumcision and/or after the circumcision. The water mist generator is separately arranged with respect to the ultrasonic generating device, the transmission device and the circumcision device. And/or, the water mist generator may be integrally arranged on the ultrasonic generating device, the transmission device or the circumcision device. And/or, the water mist generator may include an atomizing chamber. The ultrasonic generating device is connected to the atomizing chamber and is used to provide ultrasonic waves to atomize the stored water, and/or, a second ultrasonic generating device is further included. The second ultrasonic generating device is connected to the atomizing chamber and is used to provide ultrasonic waves to atomize the stored water. The ultrasonic circumcision assembly further includes a protection device which is configured to protect the glans and/or the foreskin that needs to be reserved before the circumcision, during the circumcision and/or after the circumcision. The protection device is an annular structure with adjustable diameter and is configured to fasten the foreskin at a position near a front part of the glans. And/or, the protection device may be a baffle arranged inside the foreskin and in the front part of the glans. And/or, the protection device may be an ultrasonic insulation structure and/or a vibration-damping energy-dissipation structure arranged at the inner periphery of the inner ring. And/or, the protection device and the circumcision device are connected or not connected. Preferably, the protection device and the circumcision device are connected through the ultrasonic insulation structure and/or the vibration-damping energy-dissipation structure.

The water mist/powder generator includes an annular storing device which is arranged along the transmission device and is configured to store water, liquid medicine or powder. The rear end of the storing device may be connected to the ultrasonic generating device, so as to atomize the water or liquid medicine. The front end of the storing device is provided with a closable spraying mouth or opening.

Optionally, a spraying device and an atomizing chamber which are fixed on the transmission device are provided.

Preferably, the protection device/structure is an ultrasonic insulation structure and/or a vibration-damping energy-dissipating structure. Preferably, the protection device/structure is a rubber ring arranged at the inner loop of the inner ring.

A portion of the circumcision device that contacts the foreskin tissues is coated with Teflon™ material.

The frequency of the ultrasonic generating device is adjustable.

A blade is arranged between the inner ring and the outer ring for cutting. After the cutting is completed, the side surface i.e. the blunt side contacts the wound, so the blood coagulation is accomplished.

The ultrasonic circumcision assembly further includes a protection device which is configured to protect the penis, the glans and/or the foreskin that needs to be reserved before the circumcision, during the circumcision and/or after the circumcision.

The protection device is an ultrasonic insulation structure and/or a vibration-damping energy-dissipation structure which is arranged on the circumcision device in contact with penis, glans and/or the foreskin that needs to be reserved.

A portion of the circumcision device that contacts the foreskin tissues is coated with Teflon™ material.

The ultrasonic generating device is connected to a control unit. The ultrasonic generating device includes a longitudinal ultrasonic driver and a lateral ultrasonic driver.

The vibration frequency of the circumcision device is 55.5 kHz-100 kHz.

When the water mist generator is an ultrasonic water mist generator, the working frequency is greater than 1.7 MHz.

When the inner ring uses an open-loop structure, a smooth circular inner loop is formed when the inner ring is closed.

The inner ring or the outer ring is provided with an opening. A closing device of the opening also constitutes a fixedly-connected device which is detachably connected to the transmission device.

An angle-adjustable device is arranged between the inner ring and/or outer ring and the transmission device.

The ultrasonic generating device includes an ultrasonic generator and an ultrasonic transducer. The ultrasonic generator is driven connected to the ultrasonic transducer. The ultrasonic transducer is connected to the transmission device.

The transmission device is an ultrasonic transmitting rod.

After the inner ring and the outer ring are fastened, the pressure of the circumferential line where the outer edge of the inner ring and the inner edge of the outer ring are in contact is 0.1-3.5 N/mm (The knife-edge connecting point of the upper half part and the knife-edge connecting point of the lower half part that match with each other are located at the outer edge of the inner ring and the inner edge of the outer ring. The inner ring has at least one circle of grooves. After the inner ring and the outer ring are closed, the pressure of the circumferential line between the knife-edge and the outer groove of the inner ring is 0.1-3.5 N/mm).

The inner ring or the outer ring is made of elastic material.

The knife-edge is arranged on the outer edge of the inner ring or the inner edge of the outer ring.

The outer periphery of the inner ring is provided with an elastic ring.

The outer periphery and/or the outer sidewall of the outer ring is provided with an anti-slip structure.

A separate knife-edge is further provided. The separate knife-edge structure is movably mounted on the outer ring or inner ring.

A soft pad is further provided on the inner periphery of the inner ring and/or between the inner ring and the outer ring.

The circumcision device is fixedly connected or detachably connected to the transmission device.

The circumcision device is a closed annular structure with a reducible aperture and can receive ultrasonic waves transmitted by the transmission device to perform an ultrasonic cutting and/or blood coagulation.

The circumcision device includes a first ring and a second ring. The first ring and the second ring are arranged at intervals or are arranged at inside and outside of the foreskin, respectively along the extending direction of the foreskin.

The first ring is connected to the transmission device. The second ring is connected to the first ring and/or the transmission de The first ring is an inner ring which is placed inside the foreskin. The second ring is an outer ring which is placed outside the foreskin. The inner ring and the outer ring cooperate with each other to tightly lock the foreskin.

The outer ring has an opening that can be closed by a locking device.

The inner ring and/or the outer ring are/is connected to the transmission device.

A water mist generator is further provided to spray water mist to the circumcision device and/or the circumcision area before the circumcision, during the circumcision and/or after the circumcision.

The water mist generator is separately arranged with respect to the ultrasonic generating device, the transmission device and the circumcision device.

The water mist generator is integrally arranged on the ultrasonic generating device, the transmission device or the circumcision device.

The water mist generator is an ultrasonic water mist generator.

The water mist generator includes an atomizing chamber. The ultrasonic generating device is connected to the water atomization tank and is used to send ultrasonic waves to the atomizing chamber to atomize the stored water.

A second ultrasonic generating device is further provided. The second ultrasonic generating device is connected to the atomizing chamber and is used to send ultrasonic waves to the water atomization tank to atomize the stored water.

A protection device is further provided to protect the glans and/or the foreskin that needs to be preserved before the circumcision, during the circumcision and/or after the circumcision.

The protection device is an annular structure with reducible aperture, so as to fasten the foreskin near the front part the glans.

The protection device is a baffle arranged inside the foreskin and in the front part of the glans.

The protection device is an ultrasonic insulation structure and/or a vibration-damping energy-dissipation structure arranged on the inner periphery of the inner ring.

The distance between the protection device and the circumcision device is 1 mm-20 mm.

The protection device and the circumcision device are connected or not connected.

The protection device and the circumcision device are connected through an ultrasonic insulation structure and/or a vibration-damping energy-dissipation structure.

The circumcision device is a closed annular structure with reducible aperture. The circumcision device can receive ultrasonic waves transmitted by the transmission device and perform ultrasonic cutting and/or blood coagulation.

The circumcision device includes a first ring and a second ring. The first ring and the second ring are arranged at intervals or are arranged at inside and outside of the foreskin along the extending direction of the foreskin. The first ring is connected to the transmission device, and/or, the second ring is connected to the first ring and/or the transmission device. The first ring and/or the second ring receives the ultrasonic waves transmitted by the transmission device and performs ultrasonic cutting and/or blood coagulation. The first ring is an inner ring which is placed inside the foreskin. The second ring is an outer ring which is placed outside the foreskin. The inner ring and the outer ring cooperate with each other to fasten the foreskin.

The circumcision device is fixedly connected or detachably connected to the transmission device, and/or the transmission device has a detachable structure.

The plane where the loop of the inner ring or the outer ring is located is at an angle of 45 degrees to 135 degrees to the extending direction of the transmission device.

The plane where the loop of the inner ring or the outer ring is located is perpendicular to the extending direction of the transmission device.

The connection point which the inner ring or the outer ring is integrally connected to the transmission device is located on the upper and/or lower sidewall or the outer edge wall or inner edge wall of the inner ring or the outer ring.

The inner ring is a closed circular ring or an open ring with a smooth circular inner loop in a closed state. The outer ring has an opening. The opening can be closed by a locking device.

The inner ring is placed inside the foreskin. The outer ring is placed outside the foreskin. The inner ring and the outer ring cooperate with each other to fasten the foreskin. Alternatively, the inner ring is sleeved outside the foreskin on the penis and when the foreskin is inverted, the inner ring is covered inside the inverted foreskin. The outer ring is placed outside the inverted foreskin. The inner ring and the outer ring cooperate with each other to fasten the foreskin.

The fixedly-connected device is internal-external threads, concave-convex structure or snap-fit structure that match with each other and are respectively arranged on the inner ring, the outer ring and/or the transmission device.

The inner ring is detachably connected to the transmission device through the first fixedly-connected device. The outer ring is detachably connected to the transmission device through the second fixedly-connected device.

The inner ring and the outer ring are detachably connected to the transmission device through a fixedly-connected device.

Two transmission devices may be provided. The first transmission device is connected to the outer ring. The second transmission device is connected to the inner ring. The ultrasonic generating device includes a first ultrasonic generating device and a second ultrasonic generating device. The first ultrasonic generating device is connected to the first transmission device. The second ultrasonic generating device is connected to the second transmission.

In other alternative embodiments, a water mist generator is further provided to spray water mist to the circumcision device and/or the circumcision area before the circumcision, during the circumcision and/or after the circumcision. The water mist generator is separately arranged with respect to the ultrasonic generating device, the transmission device and the circumcision device, and/or, the water mist generator is integrally arranged on the ultrasonic generating device, the transmission device or the circumcision device. The water mist generator includes a water atomization tank. The ultrasonic generating device is connected to the atomizing chamber and is used to send ultrasonic waves to the atomizing chamber to atomize the stored water, and/or, a second ultrasonic generating device is further provided. The second ultrasonic generating device is connected to the atomizing chamber and is used to send ultrasonic waves to the water atomization tank to atomize the stored water.

A protection device is further provided which is configured to protect the glans and/or the foreskin that needs to be reserved before the circumcision, during the circumcision and/or after the circumcision. The protection device is an annular structure with reducible aperture and is configured to fasten the foreskin at a position near a front part of the glans, and/or, the protection device may be a baffle arranged inside the foreskin and in the front part of the glans, and/or, the protection device may be an ultrasonic insulation structure and/or a vibration-damping energy-dissipation structure arranged at the inner periphery of the inner ring. The protection device and the circumcision device are connected or not connected, the protection device and the circumcision device are connected through the ultrasonic insulation structure and/or the vibration-damping energy-dissipation structure.

The circumcision device is a closed annular structure with reducible aperture. The circumcision device can receive ultrasonic waves transmitted by the transmission device and perform ultrasonic cutting and/or blood coagulation.

The circumcision device includes a first ring and a second ring. The first ring and the second ring are arranged at intervals or are arranged at inside and outside of the foreskin along the extending direction of the foreskin. The first ring is connected to the transmission device, and/or, the second ring is connected to the first ring and/or the transmission device. The first ring and/or the second ring receives the ultrasonic waves transmitted by the transmission device and performs ultrasonic cutting and/or blood coagulation. The first ring is an inner ring which is placed inside the foreskin. The second ring is an outer ring which is placed outside the foreskin. The inner ring and the outer ring cooperate with each other to fasten the foreskin.

The circumcision device is fixedly connected or detachably connected to the transmission device, and/or the transmission device has a detachable structure.

The plane where the loop of the inner ring or the outer ring is located is at an angle of 45 degrees to 135 degrees to the extending direction of the transmission device.

The plane where the loop of the inner ring or the outer ring is located is perpendicular to the extending direction of the transmission device.

The connection point which the inner ring or the outer ring is integrally connected to the transmission device is located on the upper and/or lower sidewall or the outer edge wall or inner edge wall of the inner ring or the outer ring.

The inner ring is a closed circular ring or an open ring with a smooth circular inner loop in a closed state. The outer ring has an opening. The opening can be closed by a locking device.

The inner ring is placed inside the foreskin. The outer ring is placed outside the foreskin. The inner ring and the outer ring cooperate with each other to fasten the foreskin. Alternatively, the inner ring is sleeved outside the foreskin on the penis and when the foreskin is inverted, the inner ring is covered inside the inverted foreskin. The outer ring is placed outside the inverted foreskin. The inner ring and the outer ring cooperate with each other to fasten the foreskin.

The fixedly-connected device is internal-external threads, concave-convex structure or snap-fit structure that match with each other and is respectively arranged on the inner ring and the outer ring and/or the transmission device.

The inner ring is detachably connected to the transmission device through the first fixedly-connected device. The outer ring is detachably connected to the transmission device through the second fixedly-connected device.

The inner ring and the outer ring are detachably connected to the transmission device through a fixedly-connected device.

Two transmission devices may be provided. The first transmission device is connected to the outer ring. The second transmission device is connected to the inner ring. The ultrasonic generating device includes a first ultrasonic generating device and a second ultrasonic generating device. The first ultrasonic generating device is connected to the first transmission device. The second ultrasonic generating device is connected to the second transmission.

The sidewall of the ring in this application refers to the upper and lower surfaces of the ring when laid flat. The outer edge of the ring refers to the annular outer wall of the circular outer periphery. The inner edge of the ring refers to the annular inner wall of the circular inner periphery.

In the experiment, normal humidifier or dip can reach the desired effect while in the clinical use, the specially designed adjustable water mist generator can achieve better results. The above-mentioned structure would be filed as a separate application, and the details would not be repeated hereinafter.

In an alternative embodiment, the cross-section of the inner ring and the outer ring is groove-shaped, or the outer edges of the inner ring and the outer ring are each provided with a groove, or the inner ring and the outer ring are each provided with an arm, or the inner ring and the outer ring have the same inner diameter, the inner side of the outer ring is provided with an outer ring step groove, the inner ring is matched and snapped in the outer ring step groove.

In an alternative embodiment, the outer ring is an elastic rubber ring or the outer ring is in annular shape and has an opening and an edge baffle, or the groove edge of the inner ring has a double-ring knife shape, or the inner ring is a closed concave ring that has an concave surface, the concavity is low inside and high outside, so that the outer ring can be placed in the concavity of the inner ring, or the annular handle-piece includes an inner ring that is sleeved around the glans and an outer ring that matches with the inner ring. The inner ring is an elastic ring. The inner wall of the outer ring is provided with a groove which receives the elastic ring, or an outer side of the inner ring is provided with a knife-edge. The inner wall of the outer ring is provided with a groove which receives the knife-edge.

In an alternative embodiment, the annular handle-piece consists of an outer ring sleeve and an inner ring sleeve. The outer ring sleeve consists of a ratchet ring and a cutting ring. The ratchet ring is sleeved on a circular step protruding from an inner ring hole at the back of the cutting ring and is snapped by a snap ring in a circular groove on the circular step. The circular step is provided with a set of fixing pins which pierce the annular wall of the circular step and are annularly arranged. Each fixing pin is partially bent above the pin hole. The front part and the rear part are cocked-up. In the assembled state, the peak point of each ratchet corresponds to the lowest point at the middle of the bent part of the fixing pin. When the peak point of the ratchet moves backward (or forward), the cocked-up tail portion of the fixing pin can be pushed down. So that the fixing pin would be lifted along the pin hole, until the fixing pin is completely retracted back into the pin hole. When the peak point of the ratchet moves forward (or backward), the cocked-up front portion of the fixing pin can be pushed down, so that the fixing pin is inserted deeper along the pin hole. The insertion depth makes it be nailed onto an inner ring sleeve (outer wall) that has a certain gap to an inner hole wall of the outer ring sleeve.

In an alternative embodiment, the annular handle-piece consists of an outer ring, an inner ring and a ring handle. The outer ring is an open circular ring. The inner ring is a closed circular ring. The upper edge of the outer ring is inclined to the ring center and has a trapezoidal notch. The lower edge of the outer ring has a semicircular notch.

In an alternative embodiment, the annular handle-piece includes two parts, an inner ring and an outer fastener. The inner ring is a closed concave ring with a concave ring surface. The concavity is low inside and high outside. The outer fastener is placed in the concavity of the inner ring. The outer fastener is strip-shaped with a latch and lock tooth.

In an alternative embodiment, the annular handle-piece includes a fixing ring, an auxiliary ring and a fastening rope. The fixing ring consists of two semi-circular rings which are hinged together through a hinge pin. An inner hole of the fixing ring is provided with a ring washer which is formed by a taper hole. The opening end of the two semi-circular rings is provided with a convex connecting end which is in detachable connection through screws. A binding post is protruded from the outer loop of one of the semi-circular rings. The auxiliary ring is an integrated ring formed by cone rings at two ends and cylindrical ring in the middle. The cross-section of the auxiliary ring is U-shaped. The diameter of the inner ring is desirable so the glans of the penis can pass through. A certain gap is provided between the bottom diameter of the outer ring and the ring washer of the fixing taper hole, so the foreskin of the penis can pass through. The binding rope is an elastic rope that has a certain length. An end of the binding rope is sleeved on the binding post of the fixing ring.

In an alternative embodiment, the annular handle-piece consists of a large-diameter cone ring, a small-diameter cone ring and a handle, which are sequentially integrated. The large ends of large-diameter cone ring and the small-diameter cone ring face outward, and the small ends thereof intersect with each other. The inner diameter of the intersecting point smoothly transits. The inner diameter has a desirable size and allows children's glans of penis to pass through. The handle is a crescent-shaped sheet, two tips of which are connected to the outer edge of the small-diameter cone ring. The crescent-shaped gap is large enough to avoid children's glans of the penis extending out from the cone ring.

In an alternative embodiment, the annular handle-piece uses a cut ring piece which consists of a circular inner ring and an open outer ring that is arranged corresponding to the inner ring where the outer ring is accommodated. A bridging piece is further provided between the open outer ring and the inner ring. The bridging piece is configured by fastening the screw into the screw hole on the protruding part at the opening of the outer ring.

In an alternative embodiment, the annular handle-piece includes a gasket, a bottom loop and a bolt. The gasket and the bottom loop of the circumcision ring are fixedly connected through the bolt. The foreskin is press and sandwiched between the gasket and the bottom loop. The bolt passes through the connecting hole of the gasket and pass by the foreskin to screw into the connecting of the bottom loop.

In an alternative embodiment, the annular handle-piece includes an inner ring and an outer ring. A binding hole is drilled in a lower portion of the handle of the outer ring. The binding rope passes through the binding hole.

In an alternative embodiment, the annular handle-piece consists of an inner ring and an outer ring. The inner ring has an annular plate which has an inverted edge. The outer ring sleeved on the inner ring is a round ring formed by connecting two identical semi-circular ring through a fixing device of a connection part. The inner surface of the round ring is serrated, and the spike-shaped protrusions are uniformly distributed. The outer edge of the outer ring is introverted toward the center.

In an alternative embodiment, the outer wall of the annular handle-piece is provided with an annular groove.

In an alternative embodiment, the annular handle-piece is further provided with an embedder.

In an alternative embodiment, the annular handle-piece has a glans ferrule. A fastening device is arranged outside the glans ferrule. A rubber ring is arranged between the glans ferrule and the fastening device.

In an alternative embodiment, the outer loop of the inner ring of the annular handle-piece is provided with a cutting blade. The upper portion of the annular handle-piece is provided with a pair of snap holes. The upper end surface of the annular handle-piece is provided with fixing thorn. The outer snap ring having a handle is provided with a snap ring sheet. Two ends of the u-shaped handle are stuck up.

In an alternative embodiment, the annular handle-piece consists of a main ring, a sub-ring, a spiral ring and two quantitative rings. The main ring and the sub-ring are locked by two snap-fit locks and snapped into the groove of the spiral ring. The main ring and the sub-ring snapped into the groove are fastened to the spiral ring through the threads of the spiral ring and the main ring.

In an alternative embodiment, the annular handle-piece includes an auxiliary ring and a handle. The auxiliary ring is formed by connecting a large cone ring and a small cone ring back to back. The ends having larger diameter of the large cone ring and the small cone ring face outward. The ends having smaller diameter of the large cone ring and the small cone ring are connected with each other. The inner wall of the joint transits smoothly. The outer wall of the joint forms an annular groove. The front end of the handle is a crescent-shaped sheet. The middle of the crescent-shaped sheet is connected to the handle body of the handle. Two tips of the crescent-shaped sheet are connected to the outer edge of the small cone ring to form a breakable connection. The space covered by the crescent-shaped sheet can accommodate children's glans of penis extending from the inner hole of the auxiliary ring.

In an alternative embodiment, the annular handle-piece includes an auxiliary ring, a fixing ring. The auxiliary ring is formed by two cone rings and a cylindrical ring in the middle. The ends with larger diameter of the two cone rings face outwards. The ends with smaller diameter of the two cone rings are respectively connected to the outer edge of the cylindrical at two sides. The inclined outer surface of the two cone rings and the outer surface of the cylindrical ring form a circular groove. The fixing ring is formed by hinging two semi-circle rings. The outer circle at the open ends of the two semi-circle rings is provided with a screw seat. The bolt is screwed into the screw seat. The open ends of the two semi-circle rings are detachably connected through the screws. The inner peripheral surfaces of the two semi-circle rings are concave arc surfaces that are oppositely connected to form the inner hole of the fixing ring. The inner hole of the fixing ring is a conical hole having a larger hole at one end and a smaller hole at the other end. The smaller hole at one end of the fixing ring is ferruled in the circular groove on the outer surface of the auxiliary ring. The cone ring on one side of the cylindrical ring is embedded in the fixing ring through the larger hole at the other end of the fixing ring. The cone ring at the other side of the cylindrical ring is located at the outer side of fixing ring. An outer circle of one semi-circle ring of the fixing ring is provided with a binding post. A bottom end of the binding post is connected to the outer circle of the semi-circle ring through a thin neck part, so the connection is broken easily.

In an alternative embodiment, the circumcision device with annular handle-piece includes a glans ferrule. A rubber loop is movably sleeved on the glans ferrule. The outer edge of the rubber ring is covered with a fastening device. Wherein the outer edge of the glans ferrule is provided with a first inclined surface. The first inclined surface is provided with a first groove. The inner edge of the fastening device is provided with a second inclined surface corresponding to the inclined surface of the outer edge of the glans ferrule. The second inclined surface is provided with a second groove for accommodating the outer edge of the rubber ring.

In an alternative embodiment, the annular handle-piece includes an inner ring and an outer ring. The outer ring consists of two semi-circles. The ends of each of the two semi-circles are connected through an outer ring shaft. The other ends of each of the two semi-circles are connected through locking screws.

In an alternative embodiment, the annular handle-piece includes a fastening device and a glans ferrule. An outer edge of the glans ferrule is provided with two or more first grooves. A first protrusion is formed between the first grooves. The inner edge of the fastening device has two or more second protrusions cooperating with the first grooves. A second groove is formed between the second protrusions. The second groove cooperate with the first protrusion to form a cavity to hold the liquid medicine therein. The fastening device is provided with a channel for injecting the liquid medicine. The channel is connected to the cavity.

In an alternative embodiment, the annular handle-piece includes a fastening device and a glans ferrule. The glans ferrule consists of a left half ferrule and a right half ferrule which are separated with each other. A connection part of the left half ferrule and the right half ferrule is provided with a rounded corner.

In an alternative embodiment, the annular handle-piece includes a fastening device and a glans ferrule. The fastening device is an elastic circular sheet structure with an opening therein. Sliding grooves are arranged on the sheets on both sides of the opening. A sliding rod matched with the sliding groove is arranged on the sheet at one side. A fixing piece is arranged on the sheets located on the two sides of the opening. A threaded connecting rod is arranged between the fixing pieces. The outer side of the fixing piece is provided with a movable piece that is matched with the connecting rod and the threads. An elastic component is provided between the fixing pieces.

In an alternative embodiment, the annular handle-piece includes a fastening device and a glans ferrule. The fastening device consists of two half-circle pieces and a connecting buckle. The ends of each of the two half-circle pieces are connected with each other through the connecting buckle. The other ends of each of the two half-circle rings are respectively provided with a strip-shaped tooth body or a strip-shaped tooth hole which is matched with the strip-shaped tooth hole or the strip-shaped tooth body of the other half-circle piece.

In an alternative embodiment, the annular handle-piece includes a fastening device and a glans ferrule. The fastening device consists of two half-circle pieces and a connecting buckle. The ends of each of the two half-circle pieces are connected with each other through the connecting buckle. The other ends of each of the two half-circle rings are respectively provided with L-shaped parts that are matched with each other. The top of the L-shaped part is provided with a connecting rod, and the bottom platform thereof is provided with a connecting hole. The connecting rod matches with the connecting hole on the bottom platform of the L-shaped part on the other end of the other half-circle piece. The inner side of the upright end of the L-shaped part is provided with a tooth-shaped protrusion or a tooth-shaped groove. The tooth-shaped protrusion or the tooth-shaped groove is matched with the tooth-shaped protrusion or the tooth-shaped groove on the inner side of the upright end on the other end of the other half-circle piece.

In an alternative embodiment, the annular handle-piece includes a fastening device and a glans ferrule. The fastening device consists of two half-circle pieces and a connecting buckle. The ends of each of the two half-circle pieces are connected with each other through the connecting buckle. The other ends of each of the two half-circle rings are respectively provided with a hook-shaped protrusion or slot which is matched with the slot or hook-shaped protrusion of the other half-circle piece. The hook-shaped protrusion consists of a connecting plate and an inverted V-shaped fastening plate. One end of the connecting plate is connected to the end of the half-circle piece. The other end of the connecting plate is connected to the middle of the fastening plate.

In an alternative embodiment, the annular handle-piece includes a fastening device and a glans ferrule. The glans ferrule consists of a left half ferrule and a right half ferrule which are separated with each other. A connection part of the left half ferrule and the right half ferrule is provided with a rounded corner.

In an alternative embodiment, the annular handle-piece includes a fastening device and a glans ferrule. The fastening device is provided with an opening. Two ends of the opening are respectively provided with a knife-edge connecting point of the upper half part and a knife-edge connecting point of the lower half part that corresponds to each other. An end of the opening that is provided with the knife-edge connecting point of the upper half part is provided with a first step-shaped snap-fit block. An end of the opening that is provided with the knife-edge connecting point of the lower half part is provided with a second step-shaped snap-fit block. The first step-shaped snap-fit block and the second step-shaped snap-fit block are matched with each other. The first step-shaped snap-fit block is located below the knife-edge connecting point of the upper half part. The second step-shaped snap-fit block is located above the knife-edge connecting point of the lower half part.

In an alternative embodiment, the annular handle-piece further includes a fastening device. The circumcision device further includes a timer. The timer is disposed on the fastening device.

In an alternative embodiment, the annular handle-piece includes a fastening device and a glans ferrule. The fastening device has an opening. Two ends of the opening are respectively provided with a knife-edge connecting point of the upper half part and a knife-edge connecting point of the lower half part that correspond with each other. The edges of the knife-edge connecting point of the upper half part and the knife-edge connecting point of the lower half part are provided with rounded corners.

In an alternative embodiment, the annular handle-piece includes a ligaturing ring and an elastic lashing. The ligaturing ring is elastic and the outer circumference thereof is provided with an annular groove. The foreskin is bound by the elastic lashing in the annular groove. The ligaturing ring is provided with a pair of or more protrusions which are located on one side of the annular groove. The arrangement of the protrusions should not affect the binding of the foreskin. The connection between each pair of protrusions can be disconnected or released.

In an alternative embodiment, the annular handle-piece includes a ligaturing ring and an elastic lashing. The ligaturing ring is elastic and the outer circumference thereof is provided with an annular groove. The foreskin is bound in the annular groove. The ligaturing ring is divided into N arc segments. The connection between two adjacent arc segments can expand and contract within a certain range. N is a positive integer greater than 0, can be 1,2,3,4,5,6,7,8.

In an alternative embodiment, the annular handle-piece includes a fastening device and a glans ferrule. One side of the fastening device is provided with a plurality of cutting pieces to cut the necrosis foreskin into pieces.

In an alternative embodiment, the annular handle-piece includes a fastening device and a glans ferrule. The fastening device includes an annular inflation part. The inner edge of the annular inflation part is connected to a cutting part. The annular inflation part is provided with a lockable inflation port.

In an alternative embodiment, the annular handle-piece includes an elastic outer ferrule and an elastic inner ferrule. The outer ferrule is a ring made of elastic material. The opening is provided with a connecting device. The inner ferrule is an elastic annular loop that is soft inside and hard outside or is a single elastic inner ferrule. The outer width of the cross section of the outer ferrule is greater than the inner width thereof. The width of the inner ferrule is greater than or equal to the outer width of the outer ferrule.

In an alternative embodiment, the annular handle-piece includes a fastening device and a glans ferrule. The fastening device includes an annular inflation part. The inner edge of the annular inflation part is connected to a cutting part. The annular inflation part is provided with a lockable inflation port.

In an alternative embodiment, the annular handlepiece includes a fastening device and a glans ferrule. The fastening device is an integral circular structure that has an open end. The open end is provided with a fixing device.

In an alternative embodiment, the annular handle-piece includes a fastening device and a glans ferrule. The fastening device has an open end where a measuring device is provided.

In an alternative embodiment, the annular handle-piece includes a fastening device and a glans ferrule. The fastening device and the glans ferrule are integral oval structure. The fastening device has an open end where a fixing device is disposed.

In an alternative embodiment, the annular handle-piece includes an outer loop, a semi-annulus inner loop arranged at the inner side of the outer loop and an adjusting bolt for adjusting the position of the inner loop. The inner loop includes an upper piece and a lower piece. Two adjusting bolts are provided. The adjusting bolt is connected to the outer loop through threads and then is fixedly connected to the inner loop.

In an alternative embodiment, the annular handle-piece includes a ligaturing ring that is expanded and shrunk along with the penis and an elastic lashing. The ligaturing ring is elastic. An annular groove is arranged on the outer circumference of the ligaturing ring. The foreskin is bound inside the annular groove by the lashing.

In an alternative embodiment, the annular handle-piece includes a tubular inner ring and a tubular outer ring that is sleeved outside the inner ring. The outer surface of the inner ring is provided with at least one circle of grooves. The surface of the groove is provided with an elastic gasket. The inner side of the outer ring is provided with at least a circle of knife-edge. A plurality of sawtooth or protrusions are arranged at the edge of the knife-edge. The knife-edge is matched with the grooves to compress and/or cut the foreskin.

In an alternative embodiment, the annular handle-piece includes a glans ferrule and a fastening device. The inner side of the fastening device is provided with a knife-edge. The outer side of the fastening device is provided with a rubber pad for buffering.

In an alternative embodiment, the annular handle-piece includes an inner ring, an outer ring, and a connecting ring for fixing the inner ring to the outer ring. The inner ring, outer ring and connecting ring are elastic open rings with reducible aperture. A connecting piece and/or a connecting structure is arranged at the opening of the elastic open ring. One end of the inner ring is provided with a circumcision knife to cut the foreskin. One end of the outer ring is provided with a ring washer. The circumcision knife cooperates with the ring washer to compress the foreskin. A gap for accommodating the foreskin is arranged between the inner ring and the outer ring. The other end of the outer ring is connected to one end of the connecting ring. The other end of the connecting ring is provided with a blocking piece for pressing against the other end of the inner ring.

In an alternative embodiment, the annular handle-piece includes an inner ring sleeved on the glans and an outer ring cooperating with the inner ring. The inner ring has a cylinder structure. The top of the cylinder is provided with an outward-facing knife-edge. The outer ring has an annular ferrule structure. The outer ring is provided a groove matching with the knife-edge at the top of the inner ring. The inner wall of the groove is in press-fit with the knife-edge. The outer wall of the inner ring is provided with a fixing device for fixing the outer ring. The outer wall of the inner ring is provided with a binding groove.

In an alternative embodiment, the annular handle-piece includes an outer ring and an inner ring that are matched with each other. One of the inner ring or the outer ring is a fastening ring having a groove. The other one of the inner ring or the outer ring is a metal ring. The fastening ring is an inclined structure matched with the surgery spot of the penis of human body.

In an alternative embodiment, the annular handle-piece includes an annular body, an easy-to-remove block, a left handle and a right handle. The annular body and the easy-to-remove block are connected to form a complete circle ring. The connecting point of the annular body and the easy-to-remove block has a left gap and a right gap that are axially arranged. The left end of the annular body is connected to the left end of the easy-to-remove block through the bottom of the left gap. The right end of the annular body is connected to the right end of the easy-to-remove block through the bottom of the right gap. A position on the annular body near the left gap is provided with the left handle. A position on the annular body near the right gap is provided with the right handle.

In an alternative embodiment, the annular handle-piece includes an outer ring and an inner ring. The outer ring is provided with a knife-edge. An inner side of the knife-edge of the outer ring is provided with a plurality of teeth to snap the foreskin so the foreskin would not move. The teeth are arranged at the inner side of the knife-edge for one circle.

In an alternative embodiment, the annular handle-piece includes an outer ring for cutting and clamping and an inner ring for sleeving the foreskin. The inner ring consists of a one integral ring or two semi-rings or more than two arc segments. Two or more first grooves are arranged on the outer edge of the inner ring. A first protrusion is formed between the first grooves. Two or more second protrusions cooperating with the first grooves are provided on the inner edge of the outer ring. Second grooves are formed between the second protrusions. The second grooves cooperate with the second protrusions to form a cavity for containing liquid medicine. A channel is formed on the outer ring for injecting the liquid medicine. The cavity is connected to the channel.

In an alternative embodiment, the annular handle-piece includes an inner ring and an outer ring. The inner ring and the outer ring cooperate with each other. The outer ring is provided with at least two knife-edges. A plurality of cutting pieces are disposed between the knife-edges to cut the necrosis foreskin into pieces.

In an alternative embodiment, the annular handle-piece includes an inner ring and an outer ring. The outer ring has open ends. The open ends are connected through a fixing device. The knife-edge structure is located at both sides of the open ends where a knife-edge connecting point of the upper half part and a knife-edge connecting point of the lower half part are located. The knife-edge connecting point of the upper half part and the knife-edge connecting point of the lower half part are formed at both ends of the opening of the outer ring and both extend toward the outer end to form an extending section. The extending section is provided with a reinforcing rib.

In an alternative embodiment, the annular handlepiece includes an inner ring and an outer ring matched with the inner ring. The outer ring has a side wall which is connected to the knife-edge. The side wall of the outer ring is provided with an accommodating part to accommodate the gasket.

In an alternative embodiment, the annular handlepiece includes an inner ring and an outer ring. The outer ring has an opening. The opening is closed through the fixing device. The annular handlepiece further includes a separate knife-edge which is movably mounted on the outer ring or the inner ring.

In an alternative embodiment, the annular handlepiece includes an inner ring and an outer ring. The outer ring has an opening. The opening is closed through a fixing device. The outer ring uses a separated type connection structure. The open end is arranged at a corresponding position above the scrotum. The separated connecting end is disposed at a position staggered with the scrotum.

In an alternative embodiment, the annular handlepiece includes an inner ring. The inner ring has an upper end face and a lower end face and further includes an outer ring made of an annular elastic loop. The size of the annular elastic loop is matched with the inner ring.

In an alternative embodiment, the annular handlepiece includes an inner magnet ring and an outer magnet ring. The inner magnet ring and the outer magnet ring are in coaxial and are magnetically attracted. The fitting surface of the inner magnet ring and the outer magnet ring is near the penis to form a blunt oppression to the foreskin. The inner magnet ring and the outer magnet ring are covered by a covering layer.

In an alternative embodiment, the annular handlepiece includes an outer ring and an inner ring. The outer ring is provided with a knife-edge. The knife-edge has a microstructure that is used to prevent skin adhesion.

In an alternative embodiment, the annular handlepiece includes an inner ring and an outer ring. The outer ring has open ends. The open ends are connected by a fixing device. Two ends of the fixing device are respectively provided with an anti-detach hook and an anti-detach groove that matches with each other.

In an alternative embodiment, the annular handlepiece includes a fastening device and a glans ferrule. The fastening device is provided with an opening. The fastening device includes a knife-edge for cutting the foreskin. Two ends of the knife-edge located at the opening are provided with a knife-edge connecting point of the upper half part and a knife-edge connecting point of the lower half part that corresponds to each other. The edges of the knife-edge connecting point of the upper half part and the knife-edge connecting point of the lower half part are provided with rounded corners. The knife-edge connecting point of the upper half part is located above the knife-edge connecting point of the lower half part.

In an alternative embodiment, the annular handlepiece includes a fastening device and a glans ferrule. The fastening device is provided with an opening. The opening is provided with a fixing device. The fastening device includes a knife-edge for cutting the foreskin. The knife-edge is a two-layer structure. An accommodating groove is formed between the two-layer knife-edges.

In an alternative embodiment, the annular handlepiece includes an outer ferrule and an inner ferrule. The outer ferrule is a ring made of elastic material. Two ends of the operation surfaces at the butt joint of the opening are respectively provided with a positioning-guiding structure which extends along the circumferential direction. The joint of the opening of the outer ferrule is provided with one or more cylindrical or polyhedral positioning pin. A corresponding side of the joint of the opening is provided with one or more positioning grooves which are closely matched with the cylindrical or polyhedral positioning pin. The inner ferrule is an elastic annular loop that is soft inside and hard outside or is an elastic annular loop with single structure. The outer width of the cross section of the outer ferrule is greater than the inner width thereof. The width of the inner ferrule is greater than the inner width of the outer ferrule and is greater than or equal to the outer width of the outer ferrule. The inner diameter of the outer ferrule is greater than or equal to the outer diameter of the concave surface of the inner ferrule. The operation surface of outer ferrule can be embedded into the concave surface of the inner ferrule. The outer ferrule and the inner ferrule work together to form a complete foreskin loop-ligation device. When the operation surfaces of the outer ferrule and the inner ferrule are connected, one or two concave cavities that have the same circle center with the outer ferrule and the inner ferrule are formed therebetween.

In an alternative embodiment, the annular handlepiece includes an inner ring sleeved on the glans and an outer ring cooperating with the inner ring. The side walls of the inner ring and the outer ring are inclined structures matched with the inclination of the coronary sulcus of the glans of the penis. The inner ring is a cylinder structure. The top of the cylinder is provided with a knife-edge faced outwardly. The outer ring is an annular ferrule structure. The outer ring has a groove matched with the knife-edge at the top of the inner ring. The inner wall of the groove is in press-fit with the knife-edge. The outer wall of the inner ring is provided with a fixing device for fixing the outer ring. The outer wall of the inner ring is provided with a binding groove.

In an alternative embodiment, the annular handlepiece includes an inner ring and an outer ring. The inner ring is matched with the outer ring. The outer ring is provided with at least two knife-edges. Cutting pieces are disposed between the knife-edges to cut the necrosis foreskin into pieces.

In an alternative embodiment, the annular handlepiece includes an inner ring and an outer ring. The outer ring has open ends. The open ends are connected by a fixing device. A rubber ring is disposed between the inner ring and the outer ring.

In an alternative embodiment, the annular handlepiece includes an inner ring and an outer ring. The outer ring has open ends. The open ends are connected by a fixing device. An outer side wall of the outer ring is provided with an anti-slip structure.

In an alternative embodiment, the annular handlepiece includes an inner ring and an outer ring. The outer ring has an opening. The opening is closed by a fixing device. A protection layer is covered on the whole circumcision device.

In an alternative embodiment, the annular handlepiece includes an inner ring and an outer ring. The outer ring has an opening. The opening is provided with a fixing device. The fixing device includes a first serrated snap-fit block and a second serrated snap-fit block which are disposed at two ends of the opening. The first serrated snap-fit block and the second serrated snap-fit block are in a snapping connection. A protection sleeve is sleeved outside the fixing device to prevent the outer ring from flicking. The shape of the protection sleeve is matched with the fixing device.

In an alternative embodiment, the annular handlepiece includes an inner ring and an outer ring. The outer ring has an opening. The opening is provided with a fixing device. The fixing device includes a first serrated snap-fit block and a second serrated snap-fit block which are disposed at two ends of the opening. The first serrated snap-fit block and/or the second serrated snap-fit block is provided with a lock hole that penetrates the first serrated snap-fit block and/or the second serrated snap-fit block. The first serrated snap-fit block and/or the second serrated snap-fit block is provided with a groove structure that would reduce the snapping strength of the first serrated snap-fit block and/or the second serrated snap-fit block.

In an alternative embodiment, the annular handlepiece includes an inner ring and an outer ring. The outer ring has an opening. The opening is provided with a fixing device. The fixing device includes a first serrated snap-fit block and a second serrated snap-fit block which are disposed at two ends of the opening. The first serrated snap-fit block and/or the second serrated snap-fit block is provided with a lock hole that penetrates the first serrated snap-fit block and/or the second serrated snap-fit block. The first serrated snap-fit block and/or the second serrated snap-fit block extends outwards to form a baffle that is used cover the joint of the snapping end.

In an alternative embodiment, the annular handlepiece includes an inner ring and an outer ring. The outer ring has open ends. The open ends are connected through a fixing device. The knife-edge structure is located at both sides of the open ends where a knife-edge connecting point of the upper half part and a knife-edge connecting point of the lower half part are located. The knife-edge connecting point of the upper half part and the knife-edge connecting point of the lower half part are formed at both ends of the opening of the outer ring and both extend toward the outer end to form an extending section. The extending section is provided with a reinforcing rib.

In an alternative embodiment, the annular handlepiece includes an inner ring and an outer ring matched with the inner ring. The outer ring is provided with a side wall. The side wall is connected to the knife-edge. The side wall of the outer ring is provided with an accommodating part for accommodating the gasket.

In an alternative embodiment, the annular handlepiece includes an inner ring and an outer ring. The outer ring has an opening. The opening is provided with a fixing device. The inner ring is provided with a knife-edge. The opening of the outer ring includes an upper half outer ring connecting point and a lower half outer ring connecting point. The upper half outer ring connecting point and the lower half outer ring connecting point each has a rounded corner structure that corresponds to each other. The upper half outer ring connecting point and lower half outer ring connecting point are overlapped to form a seamless smooth enclosure of the outer ring.

In an alternative embodiment, the annular handlepiece includes an inner ring sleeved on the penis. The inner ring is connected to a connecting rod.

In an alternative embodiment, the annular handlepiece includes an inner ring and an outer ring. The outer ring has an opening. The opening is closed by the fixing device. A separate knife-edge is further provided. The separate knife-edge structure is movably mounted on the outer ring or inner ring.

In an alternative embodiment, the annular handlepiece includes an inner ring, an outer ring and a pin sheath. The outer ring is formed by hinging three arc-shaped movable joints. A self-locking buckle with saw tooth is disposed at the outer side of the two movable joints. The inner side of the outer ring is provided with a limit groove. The inner side of the inner ring is a smooth surface, and the outer side thereof is an anvil with a rectangular groove. A pin groove is arranged on the circumference of the pin sheath. A pin-pushing pressing-plate is arranged at the back of the pin groove.

In an alternative embodiment, the annular handlepiece includes an inner ring and an outer ring. The inner ring is an annular cylinder. Two end surfaces of the inner ring extend from the inner side to the outer side to form an upper knife-edge and a lower knife-edge respectively. The middle of the outer side of the inner ring protrudes outward to form a protrusion. The upper knife-edge, the lower knife-edge and the protrusion form a double layer groove. The outer ring includes two limit bodies. The two limit bodies are connected to each other through the connection surface. The outer ring is sleeved outside the inner ring. The two limit bodies are embedded within the double layer groove. The connection surface closely contacts with the protrusion.

In an alternative embodiment, the annular handlepiece includes an inner ring and an outer ring. The outer ring has an opening. The opening is closed through a fixing device. The outer ring uses a separated type connection structure. The open end is arranged at a corresponding position above the scrotum. The separated connecting end is disposed at a position staggered with the scrotum.

In an alternative embodiment, the annular handlepiece includes a fastening device and a glans ferrule. The fastening device has an opening where a fixing device is disposed. The fastening device includes a knife-edge for cutting the foreskin. The fixing device is respectively disposed at a male part and a female part at two ends of the opening. The male part and the female part cooperate with each other. The female part is a female fixing seat. The female fixing seat is provided with a screw hole. The male part includes a male fixing seat. The male fixing seat is provided with a screw hole. The male fixing seat cooperates with the female fixing seat. Moreover, the male fixing part further includes a screw which matches the male fixing seat and the female fixing seat and is connected to the male part and the female part.

In an alternative embodiment, the annular handlepiece includes an inner ring and an outer ring that cooperate with each other. The outer ring has an outer wall and a knife-edge. A cavity is formed among the outer wall of the outer ring, the knife-edge and the inner ring. A protection cover is covered on the cavity so the cavity is isolated from the external environment.

In an alternative embodiment, the annular handlepiece includes an inner ring and an outer ring. The outer ring has a knife-edge and an opening. The side surfaces of the inner ring and the outer ring are inclined. Also, the inner ring and the outer ring each has an oval ring structure that are matched with each other.

In an alternative embodiment, the annular handlepiece includes an inner ring. The inner ring has an upper end surface and a lower end surface. The inner ring further includes an annular elastic ring. The size of the annular elastic ring is matched with the inner ring.

In an alternative embodiment, the annular handlepiece includes an outer ring and an inner ring. The outer ring has a left open end and a right open end. The left open end and the right open end are respectively provided with a male part and a female part that are matched with each other. The male part and the female part are respectively arranged at the left open end and the right open end. The male part includes a male connector. The male connector includes a rod body. The side surface of the rod body is provided with an elastic sheet. An angle is formed between the elastic sheet and the rod body. The female part includes a female connector. The female connector has an accommodating space. The accommodating space is matched with the shape of the male connector. The male connector is accommodated in the accommodating space. The female connector has a snapping edge where the elastic sheet is snapped so as to prevent the male connector from detaching.

In an alternative embodiment, the annular handlepiece includes an outer ring and an inner ring. The outer ring has a knife-edge. The knife-edge of the outer ring is provided with a plurality of drainage devices.

In an alternative embodiment, the annular handlepiece includes an inner magnet ring and an outer magnet ring. The inner magnet ring and the outer magnet ring are in coaxial and are magnetically attracted. The fitting surface of the inner magnet ring and the outer magnet ring is near the penis. The inner magnet ring and the outer magnet ring are covered by a covering layer.

In an alternative embodiment, the annular handlepiece includes a ring body. An annular V-shaped groove is disposed at the ring body. A binding gap is formed at the ring edge of the proximal end of the ring body to prevent compression of the foreskin.

In an alternative embodiment, the annular handlepiece includes an outer ring and an inner ring. The outer ring has a knife-edge. The knife-edge has a micro-structure for preventing skin adhesion.

In an alternative embodiment, the outer ring of the annular handlepiece has an opening. The open ends of the outer ring are connected through a fixing device. The fixing device includes a first connection end and a second connection end which are located at two sides of the opening. The fixing device is provided with a limit structure.

In an alternative embodiment, the annular handlepiece includes an inner ring and an outer ring. The outer ring has open ends which are connected through a fixing device. Two ends of the fixing device are respectively provided with an anti-detach hook and an anti-detach groove which cooperate with each other.

In an alternative embodiment, the annular handlepiece includes an outer ring and an inner ring. A shielding part is disposed at two ends of the inner ring. A notch is preset at one end surface of the inner ring.

In an alternative embodiment, the outer ring of the annular handlepiece has a knife-edge and a knife back. The opening of the outer ring is closed by a locking mechanism. The locking mechanism includes a locking male end and a locking female end. The locking male end is disposed at one end of the opening, and the locking female end is disposed at the other end of the opening.

In an alternative embodiment, the annular handlepiece includes an inner loop, and further includes a cutting blade and a cutter. The cutting blade is annular. The cutting blade is fixedly connected to the inner loop. The cutting blade is provided with a circular handlepiece. The blade of the circular handlepiece faces outward. The cutter includes a cutting tape. The cutting tape surrounds the outer periphery of the cutting blade corresponding to the circular handlepiece and is retractable toward the circular handlepiece.

In an alternative embodiment, the annular handlepiece includes an inner loop and further includes an annular cutting blade and a cutting ring. The annular cutting blade is fixedly connected to the inner loop. The annular cutting blade is provided with a circular handlepiece. The blade of the circular handlepiece faces outward. The cutting ring includes an upper semi-ring and a lower semi-ring. One end of the upper semi-ring is hinged to one end of the lower semi-ring. The cutting ring is located on the outer periphery of the annular cutting blade and corresponds to the circular handlepiece.

In an alternative embodiment, the outer ring of the annular handlepiece has an opening. The opening of the outer ring is closed by a closing adjustment structure. The closing adjustment structure includes an extension arm provided at one side of the opening, a hydraulic adjusting device provided at the other side of the opening including a hydraulic part and a moving part, wherein the hydraulic part is arranged near the open end, the moving part is arranged far away from the open end, an snap-fit part provided on the moving part of the hydraulic adjusting device. The extension arm and the snap-fit part are matched and fixed to achieve the open and close of the opening. The hydraulic part of the hydraulic adjusting device drives the moving part which is movably connected to the hydraulic part, so that the snap-fit part and the extension arm that are connected with each other are driven to move away from the open end.

In an alternative embodiment, the outer ring of the annular handlepiece has an opening. The knife-edge at two ends of the opening of the outer ring are respectively provided with a knife-edge connecting point of the upper half part and a knife-edge connecting point of the lower half part. A first extension arm is disposed at the left end of the opening. A second extension arm is disposed at the right end of the opening. The first extension arm and the second extension arm are disposed in a staggered manner. A hydraulic device is disposed at the opening. The center of the hydraulic device is provided with a hydraulic part. A left end of the hydraulic part is connected to a first push rod. A right end of the hydraulic part is connected to a second push rod. The first push rod is connected to the second extension arm. The second push rod is connected to the first extension arm. The hydraulic part of the hydraulic device drives the first push rod and the second push rod located at two sides so as to make the first push rod and the second push rod respectively slid toward the left side and the right side. The first push rod leads the second extension arm to move toward the left end, and the second push rod leads the first extension arm to move toward the right end so the tightness of the opening is adjusted.

In an alternative embodiment, the outer ring of the annular handlepiece has an opening. One side of the opening of the outer ring is provided with a first gear and a second gear. The first gear meshes with the second gear. The other side of the opening of the outer ring is provided with a first rack and a second rack that extend outward. The first gear meshes with the first rack. The first rack moves toward the opposite side of the first rack under the gradual drive of the first gear. The second gear meshes with the second rack. The second gear drives the second rack to move toward the opposite side of the second rack under the drive of the first gear.

In an alternative embodiment, the outer ring of the annular handlepiece has an opening. Two ends of the opening of the outer ring are respectively provided with a knife-edge connecting point of the upper half part and a knife-edge connecting point of the lower half part that are matched with each other. One side of the opening of the outer ring is provided with a rack. The other side of the opening of the outer ring is provided with a unidirectional-rotation gear that is matched with the rack.

In an alternative embodiment, the annular handlepiece includes a support structure and a blocking structure. The support structure and the blocking structure cooperates with each other to accomplish the circumcision. The support structure or the blocking structure should satisfy at least one of the following conditions: the supporting structure is a rigid structure, the blocking structure is an elastic structure, wherein the supporting structure is a rigid closed single-layer supporting ring, the blocking structure is an elastic blocking wire or an elastic blocking ring; the supporting structure is an elastic structure and the blocking structure is a rigid structure.

In an alternative embodiment, the annular handlepiece includes a knife-edge, an inner ring and an outer ring. An end of the knife-edge is provided with a medicine outlet hole. The disposable circumcision stapler is provided with a medicine injection hole that is communicated with the medicine outlet hole.

In alternative embodiments, the annular handlepiece includes an outer ring for cutting and clamping and an inner ring for sleeving around the foreskin. The inner ring consists of an integral ring, or two semi-rings, or more than two arc-shaped segments. The outer surface of the inner ring is provided with at least one circle of groove. The inner side of the outer ring is provided with at least one circle of knife-edge. A plurality of serrations or protrusions are uniformly distributed on the edge of the knife-edge. The knife-edge cooperates with the groove to compress and/or cut the foreskin.

In an alternative embodiment, the annular handlepiece includes an inner ring and an outer ring. The outer ring is provided with a knife-edge. The outer surface of the disposable circumcision stapler is provided with an elastic layer.

In an alternative embodiment, the annular handlepiece includes an inner ring and an outer ring with a knife-edge. The annular handlepiece further includes an elastic gasket that is disposed adjacent to the knife-edge.

In an alternative embodiment, the outer ring of the annular handlepiece has a knife-edge and a knife back. The opening of the outer ring is closed by a locking mechanism. The locking mechanism includes a locking male end and a locking female end. The locking male end is disposed at one end of the opening, and the locking female end is disposed at the other end of the opening.

In an alternative embodiment, the annular handlepiece includes an inner loop and further includes an annular cutting blade and a cutting ring. The annular cutting blade is fixedly connected to the inner loop. The annular cutting blade is provided with a circular handlepiece. The blade of the circular handlepiece faces outward. The cutting ring includes an upper semi-ring and a lower semi-ring. One end of the upper semi-ring is hinged to one end of the lower semi-ring. The cutting ring is located on the outer periphery of the annular cutting blade and corresponds to the circular handlepiece.

In an alternative embodiment, the annular handlepiece includes an outer ring and an inner ring. The outer ring has a knife-edge. The surface of the knife-edge of the outer ring is provided with a plurality of drainage grooves to relieve edema.

In an alternative embodiment, the annular handlepiece consists of an inner ring and an outer ring. The outer ring consists of a front ring, a back ring and a fixing handle. The front ring and the back ring are connected through the fixing handle. A gap between the front ring and the back ring is provided with a surgical knife handle. A surgical knife is fixed inside the surgical knife handle to cut the foreskin fixed by the inner ring.

In an alternative embodiment, the outer ring of the annular handlepiece has an opening. The opening of the outer ring is closed by a closing adjustment structure. The closing adjustment structure includes an extension arm disposed at one side of the opening, a hydraulic adjusting device disposed at the other side of the opening wherein the hydraulic adjusting device includes a hydraulic part and a moving part, the hydraulic part is arranged near the open end and the moving part is arranged far away from the open end, a snap-fit part disposed on the moving part of the hydraulic adjusting device. The extension arm is fixed to the snap-fit part to close the opening. The hydraulic part of the hydraulic adjusting device drives the moving part which is movably connected to the hydraulic part, so the snap-fit part and the extension arm that are connected with each other are driven to move away from the open end.

In an alternative embodiment, the outer ring of the annular handlepiece has an opening. The knife-edge at two ends of the opening of the outer ring are respectively provided with a knife-edge connecting point of the upper half part and a knife-edge connecting point of the lower half part. A first extension arm is disposed at the left end of the opening. A second extension arm is disposed at the right end of the opening. The first extension arm and the second extension arm are disposed in a staggered manner. A hydraulic device is disposed at the opening. The center of the hydraulic device is provided with a hydraulic part. A left end of the hydraulic part is connected to a first push rod. A right end of the hydraulic part is connected to a second push rod. The first push rod is connected to the second extension arm. The second push rod is connected to the first extension arm. The hydraulic part of the hydraulic device drives the first push rod and the second push rod located at two sides so as to make the first push rod and the second push rod respectively slid toward the left side and the right side. The first push rod leads the second extension arm to move toward the left end, and the second push rod leads the first extension arm to move toward the right end so the tightness of the opening is adjusted.

In an alternative embodiment, the outer ring of the annular handlepiece has an opening. Two ends of the opening of the outer ring are respectively provided with a knife-edge connecting point of the upper half part and a knife-edge connecting point of the lower half part that are matched with each other. One side of the opening of the outer ring is provided with a rack. The other side of the opening of the outer ring is provided with a unidirectional-rotation gear that is matched with the rack.

In an alternative embodiment, the outer ring of the annular handlepiece has an opening. One side of the opening of the outer ring is provided with a first gear and a second gear. The first gear meshes with the second gear. The other side of the opening of the outer ring is provided with a first rack and a second rack that extend outward. The first gear meshes with the first rack. The first rack moves toward the opposite side of the first rack under the gradual drive of the first gear. The second gear meshes with the second rack. The second gear drives the second rack to move toward the opposite side of the second rack under the drive of the first gear.

In an alternative embodiment, the annular handlepiece includes a knife-edge, an inner ring and an outer ring. An end of the knife-edge is provided with a medicine outlet hole. The disposable circumcision stapler is provided with a medicine injection hole that is communicated with the medicine outlet hole.

In an alternative embodiment, the annular handlepiece includes an outer ring. The outer ring includes a left semi-ring and a right semi-ring that cooperate with each other. Both ends of the left semi-ring and the right semi-ring are connected through a fastening device.

In an alternative embodiment, the annular handlepiece includes an inner ring and an outer ring. The outer ring is provided with a knife-edge. The outer surface of the disposable circumcision stapler is provided with an elastic layer.

In an alternative embodiment, the annular handlepiece includes an inner ring and an outer ring. The inner ring and the outer ring have the same inner diameter and outer diameter. The inner ring and the outer ring each has four gaps disposed at the periphery. A soft pad is disposed between the inner ring and the outer ring. An auxiliary ring with a blade is disposed outside the inner ring and the outer ring. A handle is disposed at the outer side of the auxiliary ring. A buckle is arranged on the outer side of the inner ring and the outer ring.

In an alternative embodiment, the annular handlepiece includes an inner ring and an outer ring with a knife-edge, and further includes an elastic gasket. The elastic gasket is disposed adjacent to the knife-edge.

In an alternative embodiment, two ends of the opening of the outer ring of the annular handlepiece are respectively provided with a first fixing seat and a second fixing seat. The first fixing seat is provided with a screw. The second fixing seat is provided with a through hole. The screw passes through the through hole to be fastened with the nut. The screw is integrally formed with the first fixing seat. The inner wall of the through hole has an inclined groove. The nut has a protrusion that extends obliquely outward. The incline direction of the protrusion is the same as that of the groove. The direction of close rotation of the nut is opposite to the incline direction of the protrusion.

In an alternative embodiment, the outer ring of the annular handlepiece is provided with an opening. Two ends of the opening of the outer ring are respectively provided with a first fixing seat and a second fixing seat. A screw passes through the through holes of the first fixing seat and the second fixing seat, sequentially. The screw has threaded interface. The screw is fixed on the first fixing seat through a check fixing sleeve.

In an alternative embodiment, the annular handlepice includes a fastening device and a glans ferrule. The fastening device has an opening. Two ends of the opening are respectively provided with a knife-edge connecting point of the upper half part and a knife-edge connecting point of the lower half part that correspond to each other. The open ends of the fastening device are connected by a locking device. The locking device has a ring wall and a knife-edge. The inner end of the knife-edge is connected to a buffer gasket.

In an alternative embodiment, the annular handlepiece includes an inner ring and an outer ring. The outer ring has a knife-edge. The side surfaces of the inner ring and the outer ring have inclined structures.

In an alternative embodiment, the annular handlepiece includes an inner ring and an outer ring matched with the inner ring. The outer ring has a side wall. The side wall is connected to the knife-edge. The width of the section of the inner ring is less than or equal to the width of the side wall of the outer ring. The width of the section of the inner ring is greater than the width of the knife-edge.

In an alternative embodiment, the annular handlepiece consists of an upper stapler, a lower stapler and a rivet fastening-adjusting component. The upper stapler is provided with an outer blade, an inner blade anti-slip groove, an anti-slip protrusion, a frenum protector and a plurality of rivet circle holes that have the same size. The cutting surface where the frenum protector is located and the cutting surface of the main body are not in the same horizontal plane. The frenum protector and the structural surface of the main body are provided with elliptical or triangular arcs that face outwardly, downwardly, backwardly, inwardly. The lower stapler is provided with a lower stapler inner blade, a lower stapler outer blade anti-slip groove, a rivet hole, a rivet fastening post, an anti-slip protrusion and a frenum protector. The cutting surface where the frenum protector is located and the cutting surface of the main body are not in the same horizontal plane. The frenum protector and the structural surface of the main body are provided with elliptical or triangular arcs that face outwardly, downwardly, backwardly, inwardly. The arcs correspond to the frenum protector of the upper stapler. The rivet fastening-adjusting component includes a rivet, a rivet protrusion, a rivet screw rod part, a rivet cap and a rivet nut part. The rivet passes through the upper stapler rivet hole, the lower stapler rivet hole, the lower stapler fastening post and a buckle ring device to integrally connect the upper stapler and the lower stapler. The outer blade of the upper stapler snapped with the lower staple outer blade anti-slip groove. The inner blade of the lower stapler snapped with the upper stapler inner blade anti-slip groove. With the fixation of the anti-slip protrusion, the upper stapler and the lower stapler are tightly connected to snapping cut the foreskin.

In an alternative embodiment, the annular handlepiece includes an inner ring and an outer ring that is used in combination with the inner ring. The outer ring is a single shaped structure. The open parts of the shaped structure are connected by a connecting device. The connecting device is provided with a check mechanism. One end of the check mechanism corresponds to the other end. The connecting device has a pre-lock condition which is lockable and a locking condition which is unlockable. In the locking condition which is unlockable, the two ends of the connecting device only can gradually close to each other.

In an alternative embodiment, the annular handlepiece includes an outer ring and an inner ring. The outer ring consists of two semi-circular open rings. The two semi-circular open rings form a full circle. The two open rings are axially located at the middle part and each has a sheet-shaped semi-circular knife-edge. The middle part of the outer side of the inner ring is a groove. The diameter of the groove is matched with the inner diameter of the knife-edge of the outer ring. Two handles are symmetrically disposed at one end of the inner ring. A V-shaped gap is formed at the other end of the inner ring.

In an alternative embodiment, the annular handlepiece includes an inner ring and an outer ring. One end of the inner ring surface of the outer ring is provided with a stepped groove. One end of the inner ring is disposed in the stepped groove of the outer ring. The inner ring and the outer ring form an annular sleeve that has same diameter. A part of the outer ring surface of the inner ring that matched with the stepped groove of the outer ring is uniformly provided with a plurality of hemispherical protrusions. Four inner ring fixing handles are disposed on the outer ring surface of the inner ring. Four outer ring fixing handles are disposed on the outer ring surface of the outer ring. The four inner ring fixing handles correspond to the four outer ring fixing handles one by one. An inner ring U-shaped fixing groove is arranged along the width direction of the inner ring fixing handle. An outer ring U-shaped fixing groove is arranged along the width direction of the outer ring fixing handle. The center of the inner ring U-shaped fixing groove and the center of the outer ring U-shaped fixing groove are on the same vertical centerline.

In an alternative embodiment, the outer ring of the annular handlepiece is provided with an opening. Two ends of the opening of the outer ring are respectively provided with a first fixing seat and a second fixing seat. A screw passes through the through holes of the first fixing seat and the second fixing seat, sequentially. The screw has threaded interface. The screw is fixed on the first fixing seat through a check fixing sleeve.

In an alternative embodiment, two ends of the opening of the outer ring of the annular handlepiece are respectively provided with a first fixing seat and a second fixing seat. The first fixing seat is provided with a screw. The second fixing seat is provided with a through hole. The screw passes through the through hole to be fastened with the nut. The screw is integrally formed with the first fixing seat. The inner wall of the through hole has an inclined groove. The nut has a protrusion that extends obliquely outward. The incline direction of the protrusion is the same as that of the groove. The direction of close rotation of the nut is opposite to the incline direction of the protrusion.

In an alternative embodiment, the annular handlepiece includes a handle. The handle is provided with an outer fixing ring. An inner fixing ring is arranged inside the outer fixing ring. One side of the bottom end of the inner fixing ring and the outer fixing ring are connected through a connector.

In an alternative embodiment, the annular handlepiece includes an inner ring and an outer ring matched with the inner ring. The outer ring has a side wall. The side wall is connected to the knife-edge. The width of the section of the inner ring is less than or equal to the width of the side wall of the outer ring. The width of the section of the inner ring is greater than the width of the knife-edge.

In an alternative embodiment, the annular handlepiece includes an inner ring and an outer ring that is used in combination with the inner ring. The outer ring is a single shaped structure. The open parts of the shaped structure are connected by a connecting device. The connecting device is provided with a check mechanism. One end of the check mechanism corresponds to the other end. The connecting device has a pre-lock condition which is lockable and a locking condition which is unlockable. In the locking condition which is unlockable, the two ends of the connecting device only can gradually close to each other.

In an alternative embodiment, the annular handlepiece includes an outer ring and an inner ring. Both the outer ring and the inner ring are tubular. The outer ring consists of two semi-circular open rings. The two open rings each has an end connected to each other through a pivot and the other ends are open ends. The two open rings are axially located at the middle part and each has a sheet-shaped semi-circular knife-edge. The middle part of the outer side of the inner ring is a groove. The diameter of the groove is matched with the inner diameter of the knife-edge of the outer ring. Two handles are symmetrically disposed at one end of the inner ring. A V-shaped gap is formed at the other end of the inner ring.

In an alternative embodiment, the annular handlepiece includes a medical silicone collar and a clamp ring sleeved outside the collar. Two ends of the clamp ring are each provided with a guide sleeve. One guide sleeve is fixed with an anti-slip convex rib. The other guide sleeve is provided with a snapping sleeve for accommodating the anti-slip convex rib. The snapping sleeve is provided with a push rod.

In an alternative embodiment, the annular handlepiece is formed by connecting the upper stapler, the lower stapler and the fastening adjusting component through a connecting device. The upper stapler is provided with an outer blade, an inner blade, a foreskin cutting buffer groove, a connecting device and a foreskin cutting adjusting device. The inner blade is provided with a foreskin cutting groove. The outer blade and the inner blade is each provided with a frenum protector. The cutting surface where the frenum protector is located and the cutting surface of the main body are not in the same horizontal plane. The cutting surface where the frenum protector is located is in triangle-arc shape.

In an alternative embodiment, the annular handlepiece is formed by connecting the upper stapler, the lower stapler and the fastening adjusting component through a connecting device. The upper stapler is provided with a single-piece foreskin cutting knife and the foreskin anti-slip protrusion. The cutting blade is provided with a foreskin cutting groove and a frenum protector. The cutting surface where the frenum protector is located and the cutting surface of the main body are not in the same horizontal plane. The frenum protector of the upper stapler and the main body structure are provided with elliptical or triangular arcs that face outwardly, downwardly, backwardly, inwardly. The upper stapler is parallel with the lower stapler.

In an alternative embodiment, the annular handlepiece includes an upper stapler frenum protector and a lower stapler frenum protector. The upper stapler frenum protector is formed by connecting a left semi-circular ring and a right semi-circular ring through a connector. The upper stapler frenum protector and the lower stapler frenum protector are integrally connected by a fastening adjusting component to cut the foreskin. The foreskin cutting single blade or dual blade of the upper stapler is provided with the frenum protector. V-shaped protrusions with triangular arc that face outwardly, downwardly or forwardly are disposed in the same horizontal plane of the cutting surface where the frenum protector is located and the main body cutting surface along the direction of the frenum. V-shaped protrusions with triangular arc that face outwardly, downwardly or backwardly are disposed in the different horizontal plane of the cutting surface where the frenum protector is located and the main body cutting surface along the direction of the frenum. The frenum protector is parallel to the lower stapler.

In an alternative embodiment, the annular handlepiece consists of an outer ring and an inner ring. The inner ring is a closed ring. The outer ring consists of two semi-circular rings. The two semi-circular rings each has an end rotatably connected to each other. The inner edge of the other end of one semi-circular ring is provided with an inner edge tooth structure. The outer edge of the other end of the other semi-circular ring is provided with an outer edge tooth structure. The inner tooth structure and the outer edge tooth structure may be engaged with each other or disengaged. After the inner tooth structure and the outer edge tooth structure are engaged with each other, the inner ring is fixed inside a formed circular ring. The outer side edge of the outer edge tooth structure is provided with a leaning structure. After the inner tooth structure and the outer edge tooth structure are engaged with each other, the leaning structure is covered inside the inner edge tooth structure to prevent the outer ring from opening without control. The leaning structure is covered inside the inner edge tooth structure with a gap for the insertion of the medical forceps left.

In an alternative embodiment, the adjusting component of the annular handlepiece consists of a rivet, an adjusting spring, a foreskin adjusting mastoid, a foreskin cutting mastoid, a rivet channel, a spring channel, a spring seat, a rivet mastoid seat, an adjusting component wall and a rivet expanding incision. The upper stapler consists of two irregular semi-circular rings, wherein the end having a frenum of the upper stapler of two semi-circle rings is connected by a connector, and the other end is connected by the adjusting component under the function of the rivet and the adjusting spring. The adjusting component is arranged on the back of the outside of the two semi-circular rings of the upper stapler, i.e., at the two sides of the opening end. The adjusting component is provided with the adjusting component wall, the rivet channel, the spring channel, the spring seat, the rivet mastoid seat, the rivet expanding incision.

In an alternative embodiment, the locking device of the annular handlepiece consists of a supporting handle, a supporting handle, a plug, an elastomer and a locking core. The supporting handle and the supporting handle are respectively integrally formed with an annular anastomosis piece and an annular anastomosis piece. The elastomer is fixed inside the inner hole of the supporting handle through the plug.

In an alternative embodiment, the annular handlepiece comprises an inner ring and an outer ring, a groove is arranged on the outer surface of the inner ring, an annular knife-edge is arranged on the inner side of the outer ring to match with the groove. The foreskin is tied between the knife-edge and the groove. The knife-edge of the outer ring is a segmented structure, the knife-edge is provided with the drainage gap intervally.

In an alternative embodiment, the annular handlepiece includes an inner magnet ring and an outer magnet ring, the inner magnet ring and the outer magnet ring are coaxial and magnetically attracted, and both the inner magnet ring and the outer magnet ring are provided with an adjusting ring coaxially. After the inner magnet ring and the outer magnet ring are attracted together, the inner magnet ring and the outer magnet ring can be adjusted by pulling the adjusting rings of the inner magnetic ring and the outer magnetic ring reversely.

In an alternative embodiment, the annular handlepiece includes a glans loop and a fastening device for holding the glans loop. The fastening device has an opening, the two ends of the opening are provided with mutually corresponding joints, and a matching ligation wire is further included. The fastening device comprises a body, the width of the body is less than that of the glans loop, so as to form a space on one side of the circumcision device for insertion of the ligation wire, thereby forming a ligation pad which is convenient to ligature at the same side also the outer surface of the glans loop.

In an alternative embodiment, the annular handlepiece is formed by connecting the upper stapler, the lower stapler and the fastening adjusting part through the connecting device. The upper stapler is provided with an outer blade, an inner blade, a foreskin cutting buffer groove, a connecting device and a foreskin cutting adjusting device. The inner blade is provided with a foreskin cutting groove. The outer blade and the inner blade is each provided with a frenum protector. The cutting surface where the frenum protector is located and the cutting surface of the main body are not in the same horizontal plane. The cutting surface where the frenum protector is located is in triangle-arc shape.

In an alternative embodiment, the annular handlepiece is formed by connecting the upper stapler, the lower stapler and the fastening adjusting component through a connecting device. The upper stapler is provided with a single-piece foreskin cutting knife and the foreskin anti-slip protrusion. The cutting blade is provided with a foreskin cutting groove and a frenum protector. The cutting surface where the frenum protector is located and the cutting surface of the main body are not in the same horizontal plane. The frenum protector of the upper stapler and the main body structure are provided with elliptical or triangular arcs that face outwardly, downwardly, backwardly, inwardly. The upper stapler is parallel with the lower stapler.

In an alternative embodiment, the annular handlepiece is formed by connecting an upper stapler, a lower stapler and a fixing adjusting component through a connecting device. The lower stapler is a circular ring. An outer wall of the lower stapler of the circular ring is provided with a foreskin cutting groove. A latex pad is disposed inside the foreskin cutting groove. An outer wall of the lower stapler of the circular ring is provided with a foreskin anti-slip protrusion. A lower edge of the outer wall of the lower stapler of the circular ring is provided with a foreskin anti-slip belt. A frenulum protector is provided at one end of the edge of the outer wall of the lower stapler of the circular ring. A frenulum positioning protrusion is provided at the edge of the outer wall of the lower stapler corresponding to the frenulum protector. The cutting surface of the frenulum protector and cutting surface of the main body are not in the same horizontal plane.

In an alternative embodiment, the annular handlepiece includes an upper stapler frenum protector and a lower stapler frenum protector. The upper stapler frenum protector is formed by connecting a left semi-circular ring and a right semi-circular ring through a connector. The upper stapler frenum protector and the lower stapler frenum protector are integrally connected by a fastening adjusting component to cut the foreskin. The foreskin cutting single blade or dual blade of the upper stapler is provided with the frenum protector. V-shaped protrusions with triangular arc that face outwardly, downwardly or forwardly are disposed in the same horizontal plane of the cutting surface where the frenum protector is located and the main body cutting surface along the direction of the frenum. V-shaped protrusions with triangular arc that face outwardly, downwardly or backwardly are disposed in the different horizontal plane of the cutting surface where the frenum protector is located and the main body cutting surface along the direction of the frenum. The frenum protector is parallel to the lower stapler.

In an alternative embodiment, the adjusting component of the annular handlepiece consists of a rivet, an adjusting spring, a foreskin adjusting mastoid, a foreskin cutting mastoid, a rivet channel, a spring channel, a spring seat, a rivet mastoid seat, an adjusting component wall and a rivet expanding incision. The upper stapler consists of two irregular semi-circular rings, wherein the end having a frenum of the upper stapler of two semi-circle rings is connected by a connector, and the other end is connected by the adjusting component under the function of the rivet and the adjusting spring. The adjusting component is arranged on the back of the outside of the two semi-circular rings of the upper stapler, i.e., at the two sides of the opening end. The adjusting component is provided with the adjusting component wall, the rivet channel, the spring channel, the spring seat, the rivet mastoid seat, the rivet expanding incision.

In an alternative embodiment, the annular handlepiece is provided with a locking device, wherein the locking device consists of a supporting handle, a supporting handle, a plug, an elastomer, and a lock cylinder. The supporting handle and the supporting handle are respectively integrally formed with an annular anastomosis piece and an annular anastomosis piece. The elastomer is fixed inside the inner hole of the supporting handle by the plug.

In an alternative embodiment, the annular handlepiece consists of an inner loop fixed collar, a fasten string and a pliers body. The inner loop fixed collar is an inclined elliptical ring, wherein a groove is provided in the middle part of the inner loop fixed collar. The fasten string is sleeved a flexible tube. The clamping ring of the pliers body is a inclined elliptical ring, which is corresponding to the shape of the inner loop fixed collar.

In an alternative embodiment, the annular handlepiece comprises an outer ring, the outer ring has an opening, the opening is provided with a locking mechanism, the opening of the outer ring is closed by the locking mechanism; the outer ring comprises a ring wall, the outer side of the ring wall of one side of the opening is provided with a first rack, the first rack is arranged parallel to the ring wall, the ring wall of the other side of the opening is provided with a second rack, the second rack is matched with the first rack. The first rack is provided with a plurality of teeth, and the teeth are disposed at the inner side of the first rack.

In an alternative embodiment, circumcision stapler comprises an inner ring and an outer ring matched with the inner ring, the inner ring is connected with the vice-inner ring and match the outer ring and the vice-outer ring respectively during the operation, so as to assist the cutting ring, the outer ring is connected with the protection ring.

In an alternative embodiment, the annular handlepiece comprises an inner ring and an outer ring, a groove is arranged on the outer surface of the inner ring, an annular knife-edge is arranged on the inner side of the outer ring to match with the groove. The foreskin is tied between the knife-edge and the groove. The knife-edge of the outer ring is a segmented structure, the knife-edge is provided with the drainage gap intervally.

In an alternative embodiment, the annular handlepiece includes an outer ring and inner ring, the outer ring includes a left semi-ring and a right semi-ring, and further includes a connecting ring, the left semi-ring, the right semi-ring and the connecting ring each having a central angle less than 180°; the lower ends of the left semi-ring and the right semi-ring are respectively hinged with the two ends of the connecting ring.

In an alternative embodiment, the annular handlepiece includes an inner magnet ring and an outer magnet ring, the inner magnet ring and the outer magnet ring are coaxial and magnetically attracted, and both the inner magnet ring and the outer magnet ring are provided with an adjusting ring coaxially. After the inner magnet ring and the outer magnet ring are attracted together, the inner magnet ring and the outer magnet ring can be adjusted by pulling the adjusting rings of the inner magnetic ring and the outer magnetic ring reversely.

In an alternative embodiment, the annular handlepiece is composed of an annular stapler and a nesting device which can be snapped into the annular stapler. The annular stapler is composed of a ring body and a holding handle connected to the ring body. The ring body is composed of two semi-circular rings which are movably connected and form a ring after closuring around the movable connecting point. And the semi-circular ring is formed by a thicker outer semi-ring and a thinner inner semi-ring which is connected with the inner circle of the outer semi-ring. One end of each of the two outer semi-rings are provided with dislocated movable connecting points, and the outer edge of the other end of each of the two outer semi-rings are provided with interoperable dislocated connecting bayonets. Two ends of the two inner semi-rings are provided with interoperable dislocated positioning-snapping-bars. The holding handle is connected with the outer edge of the serrated connection bayonet, the nesting device is composed of a cylinder, a bobbin and a handle which are respectively connected with the two ends of the cylinder; a rubber sleeve is sleeved on the bobbin, and the connection point between the handle and the cylinder is arc-shaped.

In an alternative embodiment, the annular handlepiece includes an inner ring, an outer ring, a wire and a clip, the wire is encircled around the inner ring, the outer ring is clamped on the outer side of the inner ring by the clip, one side of the inner ring turned up towards the outer edge, a number of grooves are arranged uniformly on the other side.

In an alternative embodiment, the annular handlepiece includes a glans loop and a fastening device for holding the glans loop. The fastening device has an opening, the two ends of the opening are provided with mutually corresponding joints, and a matching ligation wire is further included. The fastening device comprises a body, the width of the body is less than that of the glans loop, so as to form a space on one side of the circumcision device for insertion of the ligation wire, thereby forming a ligation pad which is convenient to ligature at the same side also the outer surface of the glans loop.

In an alternative embodiment, the annular handlepiece includes an inner ring and an outer ring. The inner ring is an oval ring body, the outer cambered surface of the inner ring is provided with an embedded cambered surface matching with the outer ring. The outer ring arranged as an elliptical annular cylinder with a diameter larger than the inner ring. The inner ring is provided with an inner cambered surface corresponding to the glans, and the lower part of the inner cambered surface is provided with a tapered protrusion.

In an alternative embodiment, the annular handlepiece comprises an outer ring, an inner ring and a silicone sleeve. Wherein the outer ring is formed by two arc-shaped parts hinged with each other. The inner ring is provided with an annular groove, the silicone sleeve is sleeved on the annular groove. One end of two arc-shape parts of the outer ring are hinged with each other, the other end of an arc-shape part among them is provided with a screw, the other end of the other arc-shape part is provided with a screw hole matched with the screw. Both sides of the inner ring are provided with annular chamfered sections, and the internal surface of the inner ring is a cambered surface.

In an alternative embodiment, the annular handlepiece includes an outer ring and an inner ring, the outer ring has an opening and the opening is closed by the fixing device. Two ends of the outer ring opening is provided with the knife-edge connecting point of the upper half part and the knife-edge connecting point of the lower half part that match with each other. A least one knife-edge arranged at the inner side of the outer ring, the knife-edge consists of the knife flank and the blade. At least a circle of groove is arranged in the inner ring, and a buffer layer is connected to the blade of the knife-edge, and the blade has a plurality of protrusions.

In an alternative embodiment, the annular handlepiece comprises an outer ring and an inner ring. The outer ring has an opening, the opening is closed by the fixing device. At least one circle of knife-edge is arranged in the inside of the outer ring which is divided into the knife flank and the blade. Two ends of the outer ring opening is provided with the knife-edge connecting point of the upper half part and the knife-edge connecting point of the lower half part that match with each other. At least one circle of groove is arranged in the inner ring, the fixing device comprises a first fixed seat and a second fixed seat arranged at both ends of the opening and a screw. The second fixed seat is provided with a perforation, the inner wall of the perforation has an inclined dent, the screw has an elastic part obliquely extending outwards, the elastic part is inclined in the same direction as the dent, and the rotation closing direction of the screw is opposite to the inclined direction of the elastic portion. The connecting part of the first fixed seat and the second fixed seat to the outer ring is the broken part.

In an alternative embodiment, the annular handlepiece includes an outer ring, wherein the outer ring has an opening end. The opening end can be closed by the fixing device. The fixing device includes left and right fixing blocks disposed on both sides of the opening end. The left and right fixing blocks are tightly closed, the left and right fixing blocks are provided with perforations, and the perforation of the left fixing block are provided with threads. The fixing device further includes a screw which penetrates through the perforation and is screwed with the threads of the left fixing block. The screw is provided with a first fastening structure at the end, the right fixing block is provided with a second fastening structure, and the first fastening structure is matched locking with the second fastening structure.

In an alternative embodiment, the annular handlepiece includes an outer ring and an inner ring. The outer ring has an opening and the opening is closed by the fixing device. Two ends of the outer ring opening is provided with the knife-edge connecting point of the upper half part and the knife-edge connecting point of the lower half part that match with each other. At least one circle of groove is arranged in the inner ring. After the outer ring and the inner ring are closed, the circumferential pressure between the knife-edge and the outer side groove of the inner ring is 0.1-3.5 N/mm.

In an alternative embodiment, a composite structure of the annular handlepiece and the pusher, wherein comprises a disposable circumcision anastomat and a pusher used cooperatively. The disposable circumcision anastomat includes an inner ring, the pusher is provided with a fixing sleeve which is used to sleeve the inner ring. The inner ring is sleeved in the fixing sleeve. The inner ring is provided with a first marking structure, and the pusher is provided with a second marking structure. The first marking structure matches the second marking structure, to ensure the correct relative position of inner ring and pusher.

In an alternative embodiment, the annular handlepiece includes a positioning ring and a clamping ring, and both the positioning ring and the clamping ring are magnetic rings. And the positioning ring and the clamping ring can be coaxially matched to each other as well as clamped and adsorbed to each other. The arc of the annular end surface of the positioning ring with the degree thereof corresponding to the central angle not greater than 180 is provided with a lace pillow.

In an alternative embodiment, the annular handlepiece includes an outer ring and an inner ring, and the inner edge of the outer ring is provided with a circle of non-continuous clamping structure.

In an alternative embodiment, the annular handlepiece includes an outer ring and an inner ring, and a protection sleeve is further provided, the cylindrical outer surface of which is detachably matched to the radial inner edge surface of the inner ring.

In an alternative embodiment, the annular handlepiece includes an inner ring and an outer loop matched therewith. The outer ring has an outer ring opening, the connecting point of the outer ring opening has mutually corresponding closed structures, the corresponding closed structures overlap to form a smooth closure. The outer ring is hinged by a plurality of arc-shaped structures, the arc-shaped structure has arc-shaped side walls, the arc-shaped side walls are connected with arc-shaped knife-edge, the plurality of arc-shaped knife-edge form an circular knife-edge, the blade of the circular knife-edge is inward. The arc-shaped side wall has repeatedly arranged protrusion structures extending toward the center of the ring. And the width of the protrusion structure is not greater than the width of the arc-shaped knife-edge. The arc-shaped knife-edge and the protrusion structure form an accommodating space.

In an alternative embodiment, the annular handlepiece includes an outer ring and an inner ring. The outer ring has an opening and the opening is closed by the fixing device. Two ends of the outer ring opening is provided with the knife-edge connecting point of the upper half part and the knife-edge connecting point of the lower half part that match with each other. A least one circle of knife-edge arranged at the inner side of the outer ring, the knife-edge consists of the knife flank and the blade. At least one circle of groove is arranged in the inner ring, and a buffer layer is connected to the blade of the knife-edge, and the blade has a plurality of protrusions.

In an alternative embodiment, the annular handlepiece comprises an outer ring and an inner ring. The outer ring has an opening, the opening is closed by the fixing device. At least one circle of knife-edge is arranged in the inside of the outer ring which is divided into the knife flank and the blade. T Two ends of the outer ring opening is provided with the knife-edge connecting point of the upper half part and the knife-edge connecting point of the lower half part that match with each other. At least one circle of groove is arranged in the inner loop, the fixing device comprises a first fixed seat and a second fixed seat arranged at both end of the opening and a screw. The second fixed seat is provided with a perforation, the inner wall of the perforation has an inclined dent, the screw has an elastic part obliquely extending outwards, the elastic part is inclined in the same direction as the dent, and the rotation closing direction of the screw is opposite to the inclined direction of the elastic portion. The connecting part of the first fixed seat and the second fixed seat to the outer ring is the broken part.

In an alternative embodiment, the annular handlepiece includes an outer ring, wherein the outer ring has an opening end. The opening end can be closed by the fixing device. The fixing device includes left and right fixing blocks disposed on both sides of the opening end. The left and right fixing blocks are tightly closed, the left and right fixing blocks are provided with perforations, and the perforation of the left fixing block are provided with threads. The fixing device further includes a screw which penetrates through the perforation and is screwed with the threads of the left fixing block. The screw is provided with a first fastening structure at the end, the right fixing block is provided with a second fastening structure, and the first fastening structure is matched locking with the second fastening structure. In an alternative embodiment, the annular handlepiece includes an outer ring and an inner ring. The outer ring has an opening and the opening is closed by the fixing device. Two ends of the outer ring opening is provided with the knife-edge connecting point of the upper half part and the knife-edge connecting point of the lower half part that match with each other. At least one circle of groove is arranged in the inner ring. After the outer ring and the inner ring are closed, the circumferential pressure between the knife-edge and the outer side groove of the inner ring is 0.1-3.5 N/mm.

In an alternative embodiment, the annular handlepiece includes an inner ring, an outer ring. The inner ring is a closed ring. The outer ring is composed of two semi-rings, the left outer ring and the right outer ring, the left outer ring and the right outer ring can be closed to form a complete circle, and two protection covers and a screw bolt are further provided. Both the left outer ring and the right outer ring include a circumferential arranged knife-edge part and an outer loop integrally connected to each other. The outer loop is located outside the knife-edge part, the outer loops of the left outer ring and the right outer ring are respectively a left outer loop and a right outer loop. The left outer loop and the right outer loop are respectively connected with a left protruding part and a right protruding part at an upper end thereof. The lower ends of the left outer ring and the right outer ring are also respectively connected with a left protruding part and a right protruding part. The left protruding part or the right protruding part is transversely provided with a through hole, and the corresponding right protruding part or left protruding part is transversely provided with a threaded hole, the bolt penetrates through the through hole and is in threaded connection with the threaded hole. The protection cover is internally hollow. The lower part of the protection cover is provided with an opening. After the upper end and the lower end of the left outer loop and the right loop are connected, the protection cover is sheathed on the bolt, the left protruding part and the right protruding part. The inner shape of the protection cover is matched with the shape of the bolt, the right protruding part and the left protruding part that are connected. The protection cover is made of flexible material.

In an alternative embodiment, the annular handlepiece includes an inner ring, an outer ring axis and an outer ring. The inner ring is a closed circle. The outer ring is composed of two semi-circles rotating relatively. Two semi-circles are the left outer ring and the right outer ring. The left outer ring and the right outer ring can be closed to form a complete circle, the lower part of the left outer ring and the right outer ring are rotationally connected through the outer ring axis, and two protection covers and a screw bolt are further provided. Both the left outer ring and the right outer ring include a circumferential arranged knife-edge part and an outer loop integrally connected to each other. The outer loop is located outside the knife-edge part, the outer loops of the left outer ring and the right outer ring are respectively a left outer loop and a right outer loop. The left outer loop and the right outer loop are respectively connected with a left protruding part and a right protruding part at an upper end thereof. The lower ends of the left outer ring and the right outer ring are also respectively connected with a left protruding part and a right protruding part. The left protruding part or the right protruding part is transversely provided with a through hole, and the corresponding right protruding part or left protruding part is transversely provided with a threaded hole, the bolt penetrates through the through hole and is in threaded connection with the threaded hole. The protection cover is internally hollow. The lower part of the protection cover is provided with an opening. After the upper end and the lower end of the left outer loop and the right loop are connected, the protection cover is sheathed on the bolt, the left protruding part and the right protruding part. The inner shape of the protection cover is matched with the shape of the bolt, the right protruding part and the left protruding part that are connected. The protection cover is made of flexible material.

In an alternative embodiment, the annular handlepiece comprises an inner ring, an outer ring. The outer ring is formed by connecting each end of two semi-rings through a hinge part and snapping the other ends through a snapping part. The middle part of the outer wall of the inner ring is provided with an annular recess for placing the gasket. The inner wall of the outer ring is provided with a first side wall, a second side wall. The inner wall of the outer ring, the first side wall and the second side wall are sequentially connected to form a medication chamber which has openings at both ends. A knife-edge is formed at an intersection of the first side wall and the second side wall, and drug exuding holes are respectively arranged on the first side wall and the second side wall.

In an alternative embodiment, the annular handlepiece comprises a disposable circumcision anastomat and a pusher used cooperatively. The disposable circumcision anastomat includes an inner ring, the pusher is provided with a fixing sleeve which is used to sleeve the inner ring. The inner ring is sleeved in the fixing sleeve. The inner ring is provided with a first marking structure, and the pusher is provided with a second marking structure. The first marking structure matches the second marking structure, to ensure the correct relative position of inner ring and pusher.

In an alternative embodiment, the annular handlepiece comprises an inner ring, an outer ring, a hinge assembly, a latching assembly, a gasket, an annular recess, a sidewall, a sidewall, a medication chamber, a knife-edge, drug exuding holes, a notch, an inclined plane, a medicine filling cap and male-female buckle. The outer ring includes a left loop and a right loop, the left ring loop and the right loop are both provided with a medicine filling cap on the outer surface, the left loop and the right loop are connected by the hinge assembly at the rear end, and the front end are connected by the latching assembly. Wherein the hinge assembly comprises a left connection strap, a right connection strap and a connecting rod. The left connection strap is mounted on the left loop, the right connection strap is mounted on the right loop, and the left connection strap and the right connection strap are connected by the connecting rod. The latching assembly comprises a latching block, a latching block and latching tooth, wherein one latching block is fixed on the left loop, the other latching block is fixed on the right loop. Both of the latching blocks are provided with latching tooth for gearing. Two ends of the latching assembly are provided with notches. The inner wall of the outer ring is provided with a side wall and a side wall. The inner wall, the side wall and the side wall of the outer ring are sequentially connected to form a medication chamber with two openings at the ends. A knife-edge is formed at the intersection of two side walls, both of the side walls are provided with drug exuding holes. The drug exuding hole is in a cylindrical shape. The male-female buckle comprises a plunger and a groove, wherein both the plunger and groove are arranged at two ends of the medication chamber. The middle part of the outer wall of the inner ring is provided with an annular recess, the gasket is arranged in the annular recess.

In an alternative embodiment, the annular handlepiece comprises an outer semi-ring and an inner semi-ring. The left end of the outer semi-ring and the left end of the inner semi-ring are connected by a connecting part. The outer side wall of the inner semi-ring is fixedly provided with a elastic pad. The inner side of the outer semi-ring is provided with an inward blade part, which is pressed on the outer wall of the elastic pad. The right end of the inner semi-ring and the right end of the outer semi-ring are fixedly connected by a locking device.

In an alternative embodiment, the annular handlepiece includes a positioning ring and a clamping ring, and both the positioning ring and the clamping ring are magnetic rings. And the positioning ring and the clamping ring can be coaxially matched to each other as well as clamped and adsorbed to each other. The arc of the annular end surface of the positioning ring with the degree thereof corresponding to the central angle not greater than 180 is provided with a lace pillow.

In an alternative embodiment, the annular handlepiece includes an outer ring and an inner ring, and the inner edge of the outer ring is provided with a circle of non-continuous clamping structure.

In an alternative embodiment, the annular handlepiece includes an outer ring and an inner ring, and a protection sleeve is provided. The cylindrical outer surface of the protection sleeve is detachably matched to the radial inner edge surface of the inner ring.

In an alternative embodiment, the annular handlepiece includes an inner ring and an outer loop matched therewith. The outer ring has an outer ring opening, the connecting point of the outer ring opening has mutually corresponding closed structures, the corresponding closed structures overlap to form a smooth closure. The outer ring is hinged by a plurality of arc-shaped structures, the arc-shaped structure has arc-shaped side walls, the arc-shaped side walls are connected with arc-shaped knife-edge, the plurality of arc-shaped knife-edge form an circular knife-edge, the blade of the circular knife-edge is inward. The arc-shaped side wall has repeatedly arranged protrusion structures extending toward the center of the ring. And the width of the protrusion structure is not greater than the width of the arc-shaped knife-edge. The arc-shaped knife-edge and the protrusion structure form an accommodating space.

In an alternative embodiment, the annular handlepiece comprises a cylindrical inner ring, a clamping tool made of titanium-nickel alloy memory material. The clamping tool is in a ring-shape, and the diameter of which is matched to that of the inner ring. The outer wall of the inner ring is wrapped with a silicone gasket.

In an alternative embodiment, the annular handlepiece comprises an outer ring, an inner ring, a blade, a connecting device, an adjusting device and a pin. The outer ring is formed by two ring-arms two-type structure whose notches are against to each other, the connecting device at the one end of the two-type structure ring-arms and the adjusting device at the other end of the two-type structure ring-arm. The connecting device adopts rivets or pins to connect one end of the two-type structure ring-arm fixedly. The adjusting device is arranged at the other end of the two-type structure ring-arm. Thereby forming the opening of the whole outer ring, the outer side of the one end of the opening is provided with an adjusting pipe with an internal thread, and the outer side of the other end is provided with a pin with an externally-threaded.

In an alternative embodiment, the annular handlepiece includes a lower magnet ring part and an upper magnet ring part. The lower magnet ring part includes a lower magnet annular shell which contains a cavity, the lower magnet ring is embedded in the cavity of the lower magnet annular shell. The upper magnet ring part comprises an upper magnet ring shell which contains a cavity, an upper magnet ring is embedded in the cavity of the upper magnet ring shell. After the upper magnet ring shell is matched with the lower magnet ring shell, the upper magnet shell is arranged on the lower magnet ring shell. The upper magnet ring shell and the lower magnet ring shell are attracted together by the upper magnet ring and the lower magnet ring, besides, they can be latching fixed through the latching structure.

In an alternative embodiment, the annular handlepiece includes an anastomosing part which comprising an upper anastomosing part and a lower anastomosing part. The upper anastomosing part and the lower anastomosing part are matching semicircular anastomosing parts. The first end surfaces of the upper anastomosing part and the lower anastomosing part are connected to each other, and the connecting point is connected by a rotating shaft. At least two fixed supports extending inwardly are located at the side of the inner side wall of the anastomosing part. At the inward end surface of the fixed support is provided with a fixing ring whose circular diameter is smaller than that of the anastomosing part. The cavity formed by the fixed support, the fixing ring, the upper anastomosing part and the lower anastomosing part is provided with a plurality of sterilized cotton fabric stacked from outside to inside.

In an alternative embodiment, the annular handlepiece includes an anastomosing part which comprising an upper anastomosing part and a lower anastomosing part. The upper anastomosing part and the lower anastomosing part are matching semicircular anastomosing parts. The first end surfaces of the upper anastomosing part and the lower anastomosing part are connected to each other, and the connecting point is connected by a rotating shaft. At least two fixed supports extending inwardly are respectively located at the sides of the inner side walls of the anastomosing part. At the inward end surface of the fixed support is provided with a fixing ring whose circular diameter is smaller than that of the anastomosing part. The cavity formed by the fixing ring, the two sides of the inner surface of the anastomosing part and the fixed support is provided with a warming cushion.

In an alternative embodiment, the annular handlepiece includes an anastomosing part which comprising an upper anastomosing part and a lower anastomosing part. The upper anastomosing part and the lower anastomosing part are matching semicircular anastomosing parts. The first end surfaces of the upper anastomosing part and the lower anastomosing part are connected to each other, and the connecting point of the first end surface is connected by a rotating shaft. The width of the second end surface of the upper anastomosing part is smaller than that of the second end surface of the lower anastomosing part. The second end surface of the lower anastomosing part recesses inwardly to form a groove and is matched to the second end surface of the upper anastomosing part.

In an alternative embodiment, the annular handlepiece includes an anastomosing part. The anastomosing part includes an outer ring and an inner ring, roller wheels are disposed between the outer ring and the inner ring so that the outer ring can slide around the inner ring. At least three rotating shafts are disposed on the inner surface of the outer ring. Each rotating shaft is provided with a pressing rod which is fixedly connected with the rotating shaft. The pressing rod passes through the matched through-hole in the inner ring. The end which is away from the rotating shafts of the pressing rod is provided with a connecting rod which is perpendicular to the pressing rod and also parallel to the inner surface of the inner ring. The end of the connecting rod which is far away from the connecting point of the pressing rod is provided with a fan-shaped blocking surface.

In an alternative embodiment, the annular handlepiece includes an anastomosing part which comprising an upper anastomosing part and a lower anastomosing part. The upper anastomosing part and the lower anastomosing part are matching semicircular anastomosing parts. The first end surfaces of the upper anastomosing part and the lower anastomosing part are connected to each other, and the connecting point of the first end surface is connected by a rotating shaft. The second end surface of the upper anastomosing part which is far away from the end of the first end surface is provided with a screw hole, the second end surface of the lower anastomosing part is provided with a fastening screw bolt matched to the screw hole. The upper anastomosing part and the lower anastomosing part both include the roll cutting belt set inside. The roll cutting belt is provided with protrusion in the head passing through the cutting hole.

In an alternative embodiment, the annular handlepiece comprises an outer ring, an inner ring and a knife. The inner ring is installed in the outer ring, a knife slot is arranged on the outer side of the inner ring, the outer ring is in a broken shape. Wherein the outer sides of two ends of the broken point are provided with the fastening holes respectively. Two fastening holes are fastening connected with each other through the fastening bolt. A knife is arranged in the knife slot, a handle is disposed on the knife.

In an alternative embodiment, the annular handlepiece comprises a cylindrical inner ring, a clamping tool made of titanium-nickel alloy memory material. The clamping tool is in a ring-shape, and the diameter of which is adapted to the diameter of the inner ring. The outer wall of the inner ring wrapped with a silicone gasket.

In an alternative embodiment, the annular handlepiece comprises an outer ring, an inner ring, a cutter edge, a connecting device, an adjusting device and a pin. The outer ring is formed by two ring-arms two-type structure whose notches are against to each other, the connecting device at the one end of the two-type structure ring-arms and the adjusting device at the other end of the two-type structure ring-arm. The connecting device adopts rivets or pins to connect one end of the two-type structure ring-arm fixedly. The adjusting device is arranged at the other end of the two-type structure ring-arm. Thereby forming the opening of the whole outer ring, the outer side of one end of the opening is provided with an adjusting pipe with an internal thread, and the outer side of the other end is provided with a pin with an externally-threaded.

In an alternative embodiment, the annular handlepiece includes an inner side ring and an outer side ring, both of the inner side ring and the outer side ring has multipolar magnetic fields therein. The axial projections of the inner side ring and the outer side ring are the same. The inner side ring and the outer side ring can be axially overlapped and absorbed to each other as well as be clamped to each other. Wherein the number of magnetic fields of the multipolar magnetic field in the inner side ring and the outer side ring are the same. The multipolar magnetic field of the inner side ring and the multipolar magnetic field of the outer side ring can be attracted in pairs by the opposite magnetic poles thereof. The protrusion shaped as a circular array revolving around the central axis on one or two axial end faces of the inner side ring and the outer side ring is provided with a plurality of antiskid tooth.

In an alternative embodiment, the annular handlepiece includes an outer ring and a matched inner ring. The outer ring has a retractable opening. The outer ring is sleeved outside the outer circumference of the inner ring through the opening. The outer loop of the inner ring has a circle of groove matched with the inner loop of the outer ring, which is used for clamping the foreskin. The groove is internally provided with a rubber ring which fits the circumferential surface of the groove to prevent the inner layer of the foreskin from slipping. The side end surface of the inner ring is provided with a handle that is convenient for doctors to operate.

In a preferred solution, an ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or healing of a wound, wherein the positioning device is integrally connected to the transmission device.

The positioning device includes: a positioning cylinder, into which the glans are partially inserted; a flange, which is formed by protruding outwards along radial direction at a distal end of the positioning cylinder; and a first annular contact surface, which is formed on the surface towards the near-end of the flange, the foreskin to be cut crosses the flange to be supported upon the first annular contact surface; the transmission device is integrally connected to the positioning cylinder, and transmit the ultrasonic waves to the first annular contact surface.

The actuating device comprises: a body frame, the positioning device is mounted in the body frame; and a cutting device, which is mounted on the body frame, and further includes an circular second annular contact surface; a driving device mounted on the body frame, which is configured to drive the second annular contact of the cutting device to move towards the first annular contact, thus compressing, cutting, hemostasis and healing for the foreskin supported on the first annular contact surface.

An ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or healing of a wound, wherein the actuating device is integrally connected to the transmission device.

The positioning device includes: a positioning cylinder, into which the glans are partially inserted; a flange, which is formed by protruding outwards along radial direction at a distal end of the positioning cylinder; and a first annular contact surface, which is formed on the surface towards the near-end of the flange, the foreskin to be cut crosses the flange to be supported upon the first annular contact surface.

The actuating device includes: a body frame, the positioning device is mounted in the body frame; a cutting device, which is mounted on the body frame, and further includes a circular second annular contact surface; the transmission device is integrally connected to the cutting device, and transmit the ultrasonic waves to the second annular contact surface; and a driving device mounted on the body frame which is configured to drive the second annular contact surface of the cutting device to move towards the first annular contact surface, thus compressing, cutting, hemostasis and healing for the foreskin supported on the first annular contact surface.

An ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or heal of a wound, wherein the actuating device is integrally connected to the transmission device.

The positioning device includes: a positioning cylinder, configured such that the glans are partially inserted into the positioning cylinder; a flange, formed by protruding radially outward at a distal end of the positioning cylinder; and a first annular contact surface, formed on the surface towards the near-end of the flange, after the cut foreskin cross the flange to be supported upon the first annular contact surface; the transmission device is integrally connected to positioning cylinder, and transmit the ultrasonic waves to the first annular contact surface.

The actuating device includes: a body frame, the positioning device is mounted in the body frame; a cutting device, which is mounted on the body frame, and further includes a circular second annular contact surface; the transmission device is integrally connected to the cutting device, and transmit the ultrasonic waves to the second annular contact surface; and a driving device mounted on the body frame which is configured to drive the second annular contact surface of the cutting device to move towards the first annular contact surface, thus compressing, cutting, hemostasis and healing for the foreskin supported on the first annular contact surface.

An ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or healing of a wound, wherein the positioning device is integrally connected to the transmission device.

The positioning device comprises: a positioning cylinder configured to sleeve on the glans; a circular first annular contact surface used for supporting the foreskin on the positioning cylinder is arranged at the near end of the positioning cylinder.

The actuating device comprises: a body frame, the positioning device is mounted in the body frame; and a cutting device, which is mounted on the body frame, and further includes an circular second annular contact surface; a driving device mounted on the body frame, which is configured to drive the second annular contact of the cutting device to move towards the first annular contact, thus compressing, cutting, hemostasis and healing for the foreskin supported on the first annular contact surface.

An ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or healing of a wound, wherein the actuating device is integrally connected to the transmission device.

The positioning device comprises: a positioning cylinder configured to sleeve on the glans; a circular first annular contact surface used for supporting the foreskin on the positioning cylinder is arranged at the near end of the positioning cylinder.

The actuating device includes: a body frame, the positioning device is mounted in the body frame; a cutting device, which is mounted on the body frame, and further includes a circular second annular contact surface; the transmission device is integrally connected to the cutting device, and transmit the ultrasonic waves to the second annular contact surface; and a driving device mounted on the body frame which is configured to drive the second annular contact surface of the cutting device to move towards the first annular contact surface, thus compressing, cutting, hemostasis and healing for the foreskin supported on the first annular contact surface.

An ultrasound subassembly for foreskin compressing, cutting, hemostasis and healing. The ultrasound is applied to the foreskin compressing, cutting, hemostasis and healing at a junction of an internal and an external tissue of a tip of human; wherein the ultrasound subassembly comprises an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; wherein the circumcision device includes a positioning device and a actuating device, which is used to compress and/or cut the foreskin, and/or, for hemostasis and/or healing of a wound, wherein the actuating device is integrally connected to the transmission device.

The positioning device comprises: a positioning cylinder configured to sleeve on the glans; a circular first annular contact surface used for supporting the foreskin on the positioning cylinder is arranged at the near end of the positioning cylinder; the transmission device is integrally connected to the positioning cylinder, and transmit the ultrasonic waves to the first annular contact surface.

The actuating device includes: a body frame, the positioning device is mounted in the body frame; a cutting device, which is mounted on the body frame, and further includes a circular second annular contact surface; the transmission device is integrally connected to the cutting device, and transmit the ultrasonic waves to the second annular contact surface; and a driving device mounted on the body frame which is configured to drive the second annular contact surface of the cutting device to move towards the first annular contact surface, thus compressing, cutting, hemostasis and healing for the foreskin supported on the first annular contact surface.

The positioning cylinder includes at least a ventilation channel.

The ventilation channel is a groove extending in the axial direction outside the positioning cylinder and/or a through hole penetrating through the wall thickness of the positioning cylinder.

The positioning cylinder further includes a clamping band, the clamping band is disposed at the periphery of the positioning cylinder, to clamp the foreskin crossing the first surface to the outside of the positioning cylinder.

The clamping band is provided with a plurality of ratchets that allow the clamping band to be a one-way clamping.

The portion of the first annular contact surface and/or the second annular contact surface that contacts the foreskin tissue is coated with Teflon™ material The angle between the first annular contact surface and the axis of the positioning cylinder is an acute angle.

The acute angle ranges from 30 degrees to 60 degrees.

A water mist generator is further included, which is used for spraying water mist to the circumcision device and/or the circumcision part before the circumcision, during the circumcision and/or after the circumcision.

The water mist generator is separately disposed with respect to the ultrasonic generating device, the transmission device and the circumcision device; or the water mist generator is integrally disposed on the ultrasonic generating device, the transmission device or the circumcision device.

The water mist generator includes an atomizing chamber; wherein the ultrasonic generating device is connected to the atomizing chamber and is used to send ultrasonic waves to atomize the stored water, and/or, further includes a second ultrasonic generating device, the second ultrasonic generating device is connected to the atomizing chamber and is used to send ultrasonic waves to atomize the stored water.

A protection device is further included, which is used for protecting the glans and/or the foreskin that needs to be preserved before the circumcision, during the circumcision and/or after the circumcision The protection device is an annular structure with an reducible aperture and is configured to fasten the foreskin at a position near a front part of the glans. And/or, the protection device may be a baffle arranged inside the foreskin and in the front part of the glans. And/or, the protection device may be an ultrasonic insulation structure and/or a vibration-damping energy-dissipation structure arranged at the inner periphery of the inner ring. Preferably, the protection device and the circumcision device are connected or not connected. Preferably, the protection device and the circumcision device are connected through the ultrasonic insulation structure and/or the vibration-damping energy-dissipation structure.

Referring to FIG. 18-25, the ultrasonic vibration device h (transducer in practical application) is connected to the vibration annular knife j, the adjustable annular knife g and the vibration annular knife j together form the outer annular handlepiece. The adjustable annular knife holder f is connected to the outer annular handlepiece through the pin b, also connected to the fixed annular knife holder c through the spring a and make the annular handlepiece openable or closable operably. The inner edge of the outer annular handlepiece is provided with an inner ring bracket d and an inner ring pad e for cooperating with the inner annular handlepiece. Preferably, a mist generator i is arranged on the fixed annular knife holder c.

Referring to FIG. 29-34, the first ultrasonic vibrator q and the second ultrasonic vibrator r are respectively connected to the first annular knife o and the second annular knife p and transmit the ultrasonic vibration thereto respectively. The first annular knife o and the second annular knife p together form the outer annular handlepiece, the inner edge of the outer annular handlepiece is provided with an inner ring bracket m and an inner ring pad n for cooperating with the inner annular handlepiece. The first scissor annular knife supportor k and second scissor annular knife supportor I support the first annular knife o and the second annular knife p respectively.

Referring to FIG. 35-44, the adjustable scissors annular knife s and the ultrasonic vibrated scissor annular knife t together form the outer annular handlepiece, the inner edge of the outer annular handlepiece is provided with the inner ring bracket u and the inner ring pad v for cooperating with the inner annular handlepiece.

Referring to FIG. 45-55, the ultrasonic vibration device F (or its transducer) is connected to the ultrasonic vibrated generating device-annular knife buckle thread compound fixedly connector E through the transmission rod, the fixedly connector E is connected to the outer annular handlepiece which is constituted by the first outer ring A and the second outer ring B. The inner edge of the outer annular handlepiece is provided with the inner ring frame C and the inner wall D for cooperating with the inner annular handlepiece. Preferably, the mist generator G is arranged in the fixed annular knife holder or the transducer, the outer annular handlepiece is provided with a protection device—restraint protection strap H.

Referring to FIG. 58-68, the ultrasonic vibration device M is connected to the outer annular handlepiece formed by a first part of outer ring I and a second part of outer ring J, the inner edge of the outer annular handlepiece is provided with the inner ring bracket K and the inner ring pad L for cooperating with the inner annular handlepiece, the mist generator N is arranged on the ultrasonic vibration device M.

Referring to FIG. 69-76, the ultrasonic vibration device h (the transducer part of the ultrasonic vibration device in practical applications) is connected to the vibration annular knife j (in practical applications, it may be a semi-ring, a quarter-ring, an arc or an end) and can transmit the ultrasonic waves to the vibration annular knife j. An adjustable annular knife g (in practical applications, it can be a semi-ring, a quarter-ring, an arc or an end) can be arranged as well, which constitutes the outer annular handlepiece together with the vibration annular knife j. The adjustable annular knife holder f is connected to the outer annular handlepiece through the pin b, also connected to the fixed annular knife holder c through the spring a and make the outer annular handlepiece openable or closable operably. The inner edge of the outer annular handlepiece is provided with the inner ring bracket d and the inner ring pad e for cooperating with the inner annular handlepiece. Preferably, the mist generator i is arranged on the fixed annular knife holder c.

Referring to FIG. 77-82, the first ultrasonic vibrator q and the second ultrasonic vibrator r are respectively connected to the first annular knife o (in practical applications, it can be a semi-ring, a quarter-ring, an arc or an end) and the second annular knife p (in practical applications, it can be a semi-ring, a quarter-ring, an arc or an end) and transmit ultrasonic vibration thereto respectively. The first annular knife o and the second annular knife p together form an outer annular handlepiece. The inner edge of the outer annular handlepiece is provided with the inner ring bracket m and the inner ring pad n for cooperating with the inner annular handlepiece. The first scissor annular knife supportor k and the second scissor annular knife supportor I support the first annular knife o and the second annular knife p respectively.

Referring to the FIG. 83-91, the adjustable scissors annular knife s (in practical applications, it can be a semi-ring, a quarter-ring, an arc or an end) and ultrasonic vibrated scissor annular knife t (in practical applications, it can be a semi-ring, a quarter-ring, an arc or an end) form the outer annular handlepiece (or the ultrasonic vibrated scissor annular knife t can be chosen to set only). The inner edge of the outer annular handlepiece is provided with the inner ring bracket u and the inner ring pad v for cooperating with the inner annular handlepiece.

Referring to the FIG. 92-97, the ultrasonic vibration device F (or its transducer) is connected to an outer annular handlepiece consists of the first outer ring (fixed outer annular knife) A and the second outer ring (adjustable outer annular knife) B. Preferably, the mist generator G is disposed on the fixed annular knife holder or the transducer. The inner edge of the outer annular handlepiece is provided with an inner ring bracket K and the first inner ring pad/the second inner ring pad L-1/L-2 for cooperating with the inner annular handlepiece. The inner annular handlepiece is a double inner ring structure, comprising a first inner annular handlepiece part and a second inner annular handlepiece part, wherein the first inner annular handlepiece part cooperates with the outer annular handlepiece. The second inner annular handlepiece part cooperates with the restraint protection strap H for the overall positioning.

According to another embodiment of the present invention, an introverted ultrasound subassembly for foreskin compressing, cutting, hemostasis and healing is provided, comprising an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; the circumcision device is used to compress and/or cut the foreskin, and/or, for hemostasis and/or healing of a wound.

In order to facilitate understanding, in this embodiment, the end that is close to the human body of the circumcision device and its various components (e.g. the right end of FIG. 14) during the circumcision is referred to as the distal end, and the end of the circumcision device and its various components that is far away from the human body or the end close to the place where the surgical staff is operating is referred to as the near end.

Figure 101:
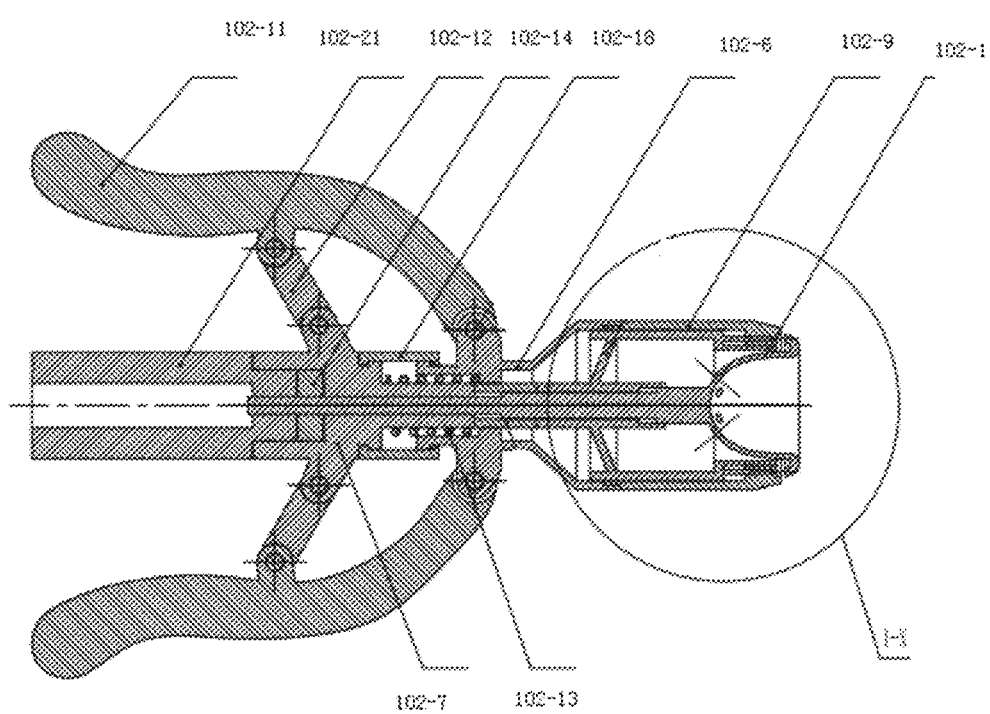
FIG. 101 is an F-F sectional view of the FIG. 100.
Figure 102:
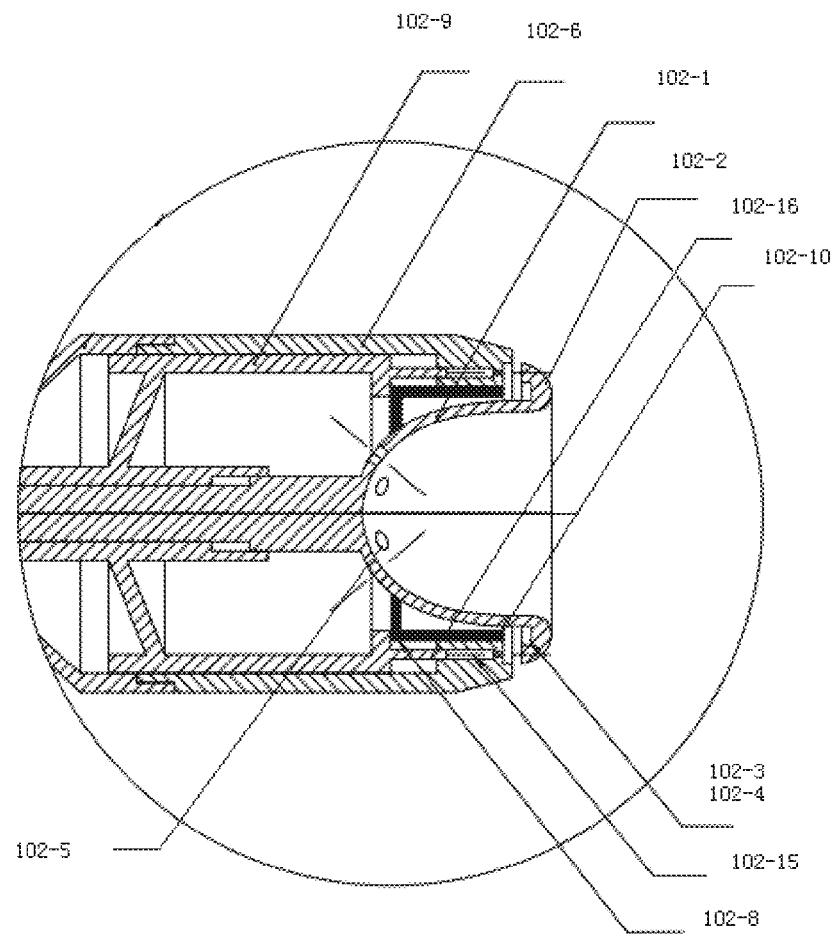
FIG. 102 is a partial enlarged view of the FIG. 100.
Figure 103:
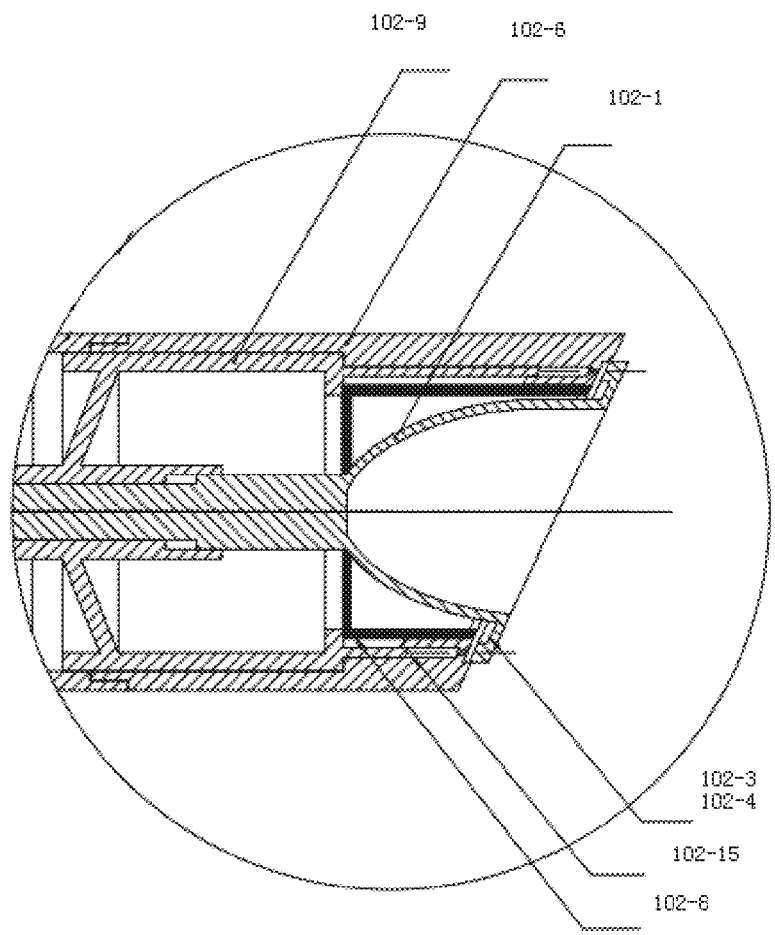
FIG. 103 is another partial enlarged view of the circumcision device of the introverted ultrasound subassembly for compressing, cutting, hemostasis and healing of foreskin of the present invention.

Referring to FIG. 98-104, the circumcision device in the present embodiment includes: the positioning cylinder 102-1, into which the glans are partially inserted; protruding outwards along the radial direction at the distal end of the positioning cylinder radially to form the flange 102-2; the first annular contact surface 102-3 is formed on the surface facing the near-end of the flange. The first annular contact surface 102-3 is covered with the first protection film 102-4 in an annular shape, the longer foreskin crosses the flange 102-2 to be supported on the first protection film 102-4 of the first annular contact surface 102-3. The structure which forms the positioning cylinder whose distal end is located between the foreskin inner plate and the penis is referred to as an introverted structure. In the above positioning cylinder, the angle between the first annular contact surface 102-3 and the axis of the positioning cylinder 102-1 may be a right angle or an acute angle. With reference to FIG. 103, the acute angle may range from 30 degrees to 60 degrees, so as to match the shape of the coronary sulcus of the glans, therewith to facilitate more accurate positioning. At least one ventilation channel 102-5 may be disposed in the positioning cylinder, and the ventilation channel 102-5 is a plurality of through holes formed in the positioning cylinder and penetrating through the wall thickness of the positioning cylinder. Referring to FIG. 101-102, for example, it can be circles, ovals, triangles, quadrangle, and other geometries or irregularities.

The circumcision device in this embodiment further includes a body frame. Referring to FIG. 101, the body frame includes a front support sleeve 102-6, a rear support sleeve 102-7 and a transition sleeve 102-18. The positioning cylinder 102-1 is mounted in the rear support sleeve 102-7 of the body frame by a tightening piece 102-21; and a cutting device, the cutting device comprises an annular knife 102-8 and an annular knife holder 102-9, the second annular contact surface 102-10 is formed by the end surfaces of the annular knife. The annular knife 102-8 is fixedly connected with the annular knife holder 102-9 and is installed outside the positioning cylinder and inside the front support sleeve 102-6 of the body frame. The cutting device is configured to be driven by the driving device to move toward the positioning cylinder 102-1 until the second annular contact surface 102-10 is in contact with the annular first protection film 102-4 on the first annular contact surface 102-3, thus compressing, cutting, hemostasis, and healing the foreskins therein. The driving device comprises a compressing rod 102-11 arranged on the body frame, one end of the compressing rod is movably connected with the front support sleeve 102-6 through a pin, the middle part of the compressing rod is connected with one end of the connecting rod 102-12 through a pin, the other end of the connecting rod 102-12 is movably connected with the rear support sleeve 102-7 through a pin. The compressing rod is pressed down by external force to push the cutting device to move within the body frame against the elastic force of the spring 102-13, and resets by the rebounding force of the spring 102-13 after the operation is completed.

In the present embodiment, the ultrasonic generating device transmits the ultrasonic waves generated by the ultrasonic generator to the circumcision device through the transmission device. The front portion of the transmission device can be connected to the positioning cylinder 102-1 and/or the annular knife 102-8 of the circumcision device through the transducer 102-14, so as to transmit ultrasonic waves to the first annular contact surface 102-3 and/or the second annular contact surface 102-10.

In order to avoid the generation of smoke and odor during the circumcision that uses the ultrasonic, which affects the visual field and the surgical environment, the circumcision device of the present invention is further provided with a water mist generator. Referring to FIG. 101-103, the water mist generator may include an annular storing device 102-15 disposed on the front support sleeve 102-6 and located on an outer periphery of the annular knife 102-8, and an export 102-17 (not shown in the figure) is disposed on a side facing the first annular contact surface 102-3 of the storing device, the storing device can store liquids such as water, alcohol, disinfectant etc. At the same time, an actuating device is also formed on the annular knife holder 102-9, such as an annular compression device 102-16, which is configured to contact the annular storing device 102-15 and compress the annular storing device to spray the stored water, alcohol or disinfectant through the export 102-17 to form water mist before the second annular contact surface 102-10 on the annular knife contacts the annular first protection film 102-4 on the first annular contact surface 102-3 while pushing the cutting device by pressing down the compression rod 102-11 using an external force to move toward the positioning cylinder within the body frame.

According to another embodiment of the present invention, an inverted ultrasound subassembly for foreskin compressing, cutting, hemostasis and healing is provided, comprising an ultrasonic generating device, a transmission device and a circumcision device; wherein the ultrasonic generating device is used to generate a plurality of ultrasonic waves, the ultrasonic generating device is connected to the transmission device and capable of transmitting the plurality of ultrasonic waves to the transmission device; wherein the transmission device is connected to the circumcision device and capable of transmitting the plurality of ultrasonic waves to the circumcision device; the circumcision device is used to compress and/or cut the foreskin, and/or, for hemostasis and/or healing of a wound.

In order to facilitate understanding, in this embodiment, the end that is close to the human body of the circumcision device and its various components (e.g. the right end in FIG. 104) during the circumcision is referred to as the distal end, and the end of the circumcision device and its various components that is far away from the human body or the end close to the place where the surgical staff is operating is referred to as the near end.

Referring to the accompany drawings 101, 103, and 104, the circumcision device in this embodiment includes: a positioning cylinder 102-1, configured to sleeve on the glans, and a first annular contact surface 102-3 disposed at near end of the positioning cylinder, the first annular contact surface 102-3 is covered with a annular first protection film 102-4, used for inverting the longer foreskin and supporting it at the near end of the positioning cylinder after the glans penetrate through the positioning cylinder from the distal end to the near end. The structure which forms the positioning cylinder whose overall body is located outside the foreskin outer plate is referred to as the inverted structure. In the above positioning cylinder, the angle between the first annular contact surface and the axis of the positioning cylinder may be a right angle or an acute angle. The acute angle may range from 30 degrees to 60 degrees. Thereby matches the shape of the coronary sulcus of the glans to facilitate more accurate positioning.

In the above circumcision device, the protection sleeve 102-19 is further provided, into which the glans are partially inserted, so as to positioning and protect the glans. In the protection sleeve, the angle between the end surface that the remaining glans contact and the axis of the protection sleeve can be a right angle or an acute angle. The acute angle may range from 30 degrees to 60 degrees. Thereby matches the shape of the coronary sulcus of the glans to facilitate more accurate positioning. At least one ventilation channel 102-5 may be provided in the protection sleeve 102-19, and the ventilation channel 102-5 is a plurality of through holes formed on the positioning cylinder by penetrating through the wall thickness of the positioning cylinder. Referring to FIG. 101-102, for example, it can be circles, ovals, triangles, quadrangles, and other geometrics or irregularities.

The circumcision device in this embodiment further includes: a body frame, a positioning cylinder is mounted in the body frame; and a cutting device mounted on the body frame; and a second annular contact surface 102-10 is further included. The cutting device may be driven by the driving device to move toward the positioning cylinder until the second annular contact surface and the first annular contact surface perform compression, cutting, hemostasis and healing to the foreskin therein. The driving device may be a compressible handle disposed on the body frame, and the compressible handle can be pressed down by an external force to push the cutting device to move within the body frame and reset by the rebounding force of the spring after the operation is completed.

Figure 104:
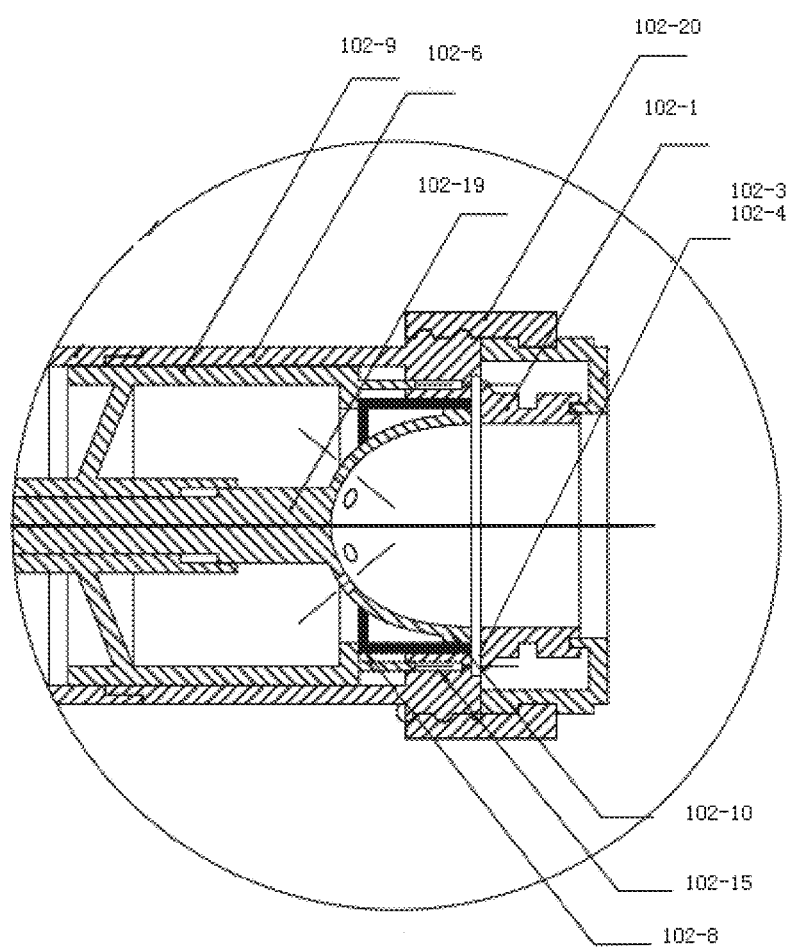
FIG. 104 is a partial enlarged view of the circumcision device of the inverted ultrasound subassembly for compressing, cutting, hemostasis and healing of foreskin of the present invention.

Referring to FIGS. 101 and 104, the positioning cylinder in the present embodiment can be fixed together with the connecting sleeve 102-20 through the front support sleeve 102-6. The outer side of the near end of the positioning cylinder is provided with an external thread, the outer side of the distal end of the front support sleeve is also provided with an external thread, and the inner side of the connecting sleeve is provided with an internal thread, all the three above are fixed by a threaded connection.

The body frame of the circumcision device in this embodiment, refers to FIG. 101, includes a front support sleeve 102-6, a rear support sleeve 102-7 and a transition sleeve 102-18. The positioning cylinder 102-1 is mounted in the rear support sleeve 102-7 of the body frame; and a cutting device, the cutting device comprises an annular knife 102-8 and an annular knife holder 102-9, a second annular contact surface 102-10 formed by the end surface of the annular knife. The annular knife and the annular knife holder are fixedly connected and are installed outside the positioning cylinder and inside the front support sleeve 102-6 of the body frame. The cutting device is configured to be driven by the driving device to move toward the positioning cylinder 102-1 until the second annular contact surface 102-10 is in contact with the annular first protection film 102-4 on the first annular contact surface 102-3, and perform compression, cutting, hemostasis and healing to the foreskin therein. The driving device comprises a compression rod 102-11 arranged on the body frame. One end of the compression rod is movably connected with the front support sleeve 102-6 through a pin, the middle part of the compression rod is connected with one end of the connecting rod 102-12 through a pin, and the other end of the compression rod is movably connected with the rear support sleeve 102-7 through a pin. The compression rod can be pressed down by an external force to push the cutting device to move within the body frame against the elastic force of the spring 102-13 and reset by the rebounding force of the spring after the operation is completed.

In the present embodiment, the ultrasonic generating device transmits the ultrasonic waves generated by the ultrasonic generator to the circumcision device through the transmission device. The front portion of the transmission device can be connected to the positioning cylinder 102-1 and/or annular knife 102-8 of the circumcision device through the transducer 102-14, so as to transmit ultrasonic waves to the first annular contact surface 102-3 and/or the second annular contact surface 102-10.

In order to avoid the generation of smoke and odor during the circumcision that uses the ultrasonic, which affects the visual field and the surgical environment, the circumcision device of the present invention is further provided with a water mist generator. Referring to FIGS. 101 and 104, the water mist generator device may include an annular storing device 102-15 disposed on the front support sleeve 102-6 and located on an outer periphery of the annular knife 102-8, and an export 102-17 (not shown in the figure) is disposed on a side facing the first annular contact surface 102-3 of the storing device, the storing device can store liquids such as water, alcohol, disinfectant etc. At the same time, an actuating device is also formed on the annular knife holder 102-9, such as the annular compression device 102-16, which is configured to contact the annular storing device and compress the annular storing device to spray the stored water, alcohol or disinfectant through the export to form water mist before the second annular contact surface 102-10 on the annular knife contacts the annular first protection film 102-4 on the first annular contact surface 102-3 while pushing the cutting device by pressing down the compression rod 102-11 using an external force to move toward the positioning cylinder within the body frame.

The frequency transmitted by the ultrasonic generating device or delivered to the handlepiece can range from 20 khz to 166.5 khz. About the technical terms: circumcision device (It can be a foreskin-cutting stapler, or a foreskin-cutting healer, or a circumcision assembly), cutting device (i.e. a resection device), positioning cylinder (i.e. a foreskin fixing end), inner ring (i.e. a foreskin fixing end or a positioning cylinder), outer ring (i.e. a cutting device).

An exemplary description of the invention is described above with reference to the accompanying drawings. It is obvious that the specific implementation of the present invention is not limited by the above modes. Various improvements made using the conception and technical solutions of the present invention or directly applied to other situations without any improvements, all of which are within the protection scope of the present invention.

What is claimed is:

1. A prepuce extruding, cutting, hemostasis, and healing assembly, comprising an ultrasonic wave generating device, a transmission device, a circumcision device, a handle, a water mist generator; wherein the ultrasonic wave generating device is configured to generate a plurality of ultrasonic waves, and the ultrasonic wave generating device is connected to the transmission device and is configured to transmit the plurality of ultrasonic waves to the transmission device;

the transmission device is connected to the circumcision device and is configured to transmit the plurality of ultrasonic waves to the circumcision device;

the circumcision device is configured to compress and cut foreskin, and for hemostasis and healing of a wound, the circumcision device comprises an outer ring and an inner ring, and the outer ring comprises a vibration annular knife and an adjustable annular knife; and the water mist generator is configured to apply liquid, mist, or powder onto the circumcision device and an action site of a circumcision prior to the circumcision, during the circumcision and after the circumcision; and the ultrasonic wave generating device comprises a first ultrasonic vibrator connected to the vibration annular knife and a second ultrasonic vibrator connected to the adjustable annular knife, the handle comprises a first scissor annular knife supportor supporting the vibration annular knife and a second scissor annular knife supportor supporting the adjustable annular knife;

wherein the circumcision device comprises a first end and a second end, the first end is a foreskin fixing end, and the second end is a compressing, cutting, hemostasis or healing end; the foreskin fixing end comprises a first annular contact surface; the compressing, cutting, hemostasis or healing end comprises a second annular contact surface; and an angle between the first annular contact surface and an axis of a positioning cylinder of the circumcision device is an acute angle from 30 to 60 degrees.

2. The prepuce extruding, cutting, hemostasis, and healing assembly of claim 1, wherein the foreskin fixing end is configured to cooperate with the compressing, cutting, hemostasis or healing end to compress and/or cut the foreskin, and/or, for hemostasis and/or healing of the wound.

3. The prepuce extruding, cutting, hemostasis, and healing assembly of claim 2, wherein a coordination mode of the foreskin fixing end and the compressing, cutting, hemostasis or healing end is that the foreskin fixing end is configured to be placed on an inner plate or an outer plate of the foreskin, and the compressing, cutting, hemostasis or healing end is configured to be placed on a position of the inner plate or the outer plate of the foreskin corresponding to the foreskin fixing end.

4. The prepuce extruding, cutting, hemostasis, and healing assembly of claim 3, wherein the foreskin fixing end and the compressing, cutting, hemostasis or healing end are configured to be positioned on the inner plate and the outer plate of the foreskin respectively to cooperate to clamp the foreskin, and used to compress and/or cut the foreskin, and/or, for hemostasis and/or healing of the wound.

5. The prepuce extruding, cutting, hemostasis, and healing assembly of claim 2, wherein the first annular contact surface is configured to cooperate with the second annular contact surface to make the foreskin placed between the first contact surface and the second contact surface.

6. The prepuce extruding, cutting, hemostasis, and healing assembly of claim 5, wherein both the first annular contact surface and the second annular contact surface are closed circular contact surfaces.

7. The prepuce extruding, cutting, hemostasis, and healing assembly of claim 5, wherein the foreskin fixing end is a first ring and the compressing, cutting, hemostasis or healing end is a second ring.

8. The prepuce extruding, cutting, hemostasis, and healing assembly of claim 7, wherein the first ring and the second ring are configured to be disposed corresponding to an inside and an outside of the foreskin, or the second ring and the first ring are configured to be disposed corresponding to the inside and the outside of the foreskin.

9. The prepuce extruding, cutting, hemostasis, and healing assembly of claim 8, wherein the first ring is configured to be the inner ring disposed inside the foreskin, the second ring is configured to be the outer ring disposed outside the foreskin; the inner ring and the outer ring cooperate to fasten the foreskin.

10. The prepuce extruding, cutting, hemostasis, and healing assembly of claim 9, wherein the inner ring is a closed circular ring, the outer ring comprises an opening, and the opening is configured for being closed by a bolt, screw hole, or buckle.

11. The prepuce extruding, cutting, hemostasis, and healing assembly of claim 1, wherein, the water mist generator is disposed separately with respect to the ultrasonic wave generating device, the transmission device and the circumcision device; or, the water mist generator is partly or entirely integrated on the ultrasonic wave generating device, the transmission device and/or the circumcision device.

12. The prepuce extruding, cutting, hemostasis, and healing assembly of claim 1, wherein the water mist generator comprises a storage device and a spraying device; wherein the storage device is arranged on the transmission device for storing liquid and/or powder; the spraying device is openable and closable, the spraying device is disposed on an end of the storage device proximate to the circumcision device and is configured for applying liquid and/or powder stored in the storage device to the circumcision device and/or the action site of the circumcision.

13. The prepuce extruding, cutting, hemostasis, and healing assembly of claim 12, wherein the storage device is an annular storage device disposed on a periphery of the transmission device; and the spraying device is a plurality of outlets arranged along an annular end face of the end of the storage device proximate to the circumcision device.

14. The prepuce extruding, cutting, hemostasis, and healing assembly of claim 1, wherein the inner ring and the outer ring cooperate with each other;

the inner ring is integrally connected to the transmission device, and a plane of an annulus of the outer ring is in a same plane as an extending direction of the transmission device, or, there is an angle between a plane of an annulus of the inner ring and the extending direction of the transmission device.

15. The prepuce extruding, cutting, hemostasis, and healing assembly of claim 14, wherein the vibration annular knife is connected to an ultrasonic vibration, and the adjustable annular knife is connected to an adjustable annular knife holder through a pin, and the adjustable annular knife holder is connected to a fixed annular knife holder through a spring and is configured to make an annular handlepiece openable or closable operably.

16. The prepuce extruding, cutting, hemostasis, and healing assembly of claim 1, wherein the circumcision device comprises the inner ring and the outer ring; the inner ring and the outer ring cooperate with each other; and the transmission device is connected to the inner ring and the outer ring, respectively.

17. The prepuce extruding, cutting, hemostasis, and healing assembly of claim 16, wherein the transmission device comprises a first transmission device and a second transmission device; the first transmission device is connected to the outer ring, and the second transmission device is connected to the inner ring.

18. The prepuce extruding, cutting, hemostasis, and healing assembly of claim 17, wherein the ultrasonic wave generating device is connected to the first transmission device and the second transmission device, respectively;

or,
the ultrasonic wave generating device comprises a first ultrasonic wave generating device and a second ultrasonic wave generating device; the first ultrasonic wave generating device is connected to the first transmission device, and the second ultrasonic wave generating device is connected to the second transmission device.

19. The prepuce extruding, cutting, hemostasis, and healing assembly of claim 1, further comprising an operation unit; wherein
the operation unit is connected to the circumcision device and used to operate the circumcision device;
or,
the circumcision device comprises the operation unit, and the operation unit is used to operate a remaining part of the circumcision device.

\* \* \* \* \*